(12) United States Patent
Sevillano et al.

(10) Patent No.: US 7,414,036 B2
(45) Date of Patent: Aug. 19, 2008

(54) COMPOUNDS USEFUL AS $A_3$ ADENOSINE RECEPTOR AGONISTS

(75) Inventors: Luis Garcia Sevillano, Toro (ES); Christopher McGuigan, Cardiff (GB); Robin Havard Davies, Cardiff (GB)

(73) Assignee: Muscagen Limited, Cardiff (GB)

( * ) Notice: Subject to any disclaimer, the term of this patent is extended or adjusted under 35 U.S.C. 154(b) by 351 days.

(21) Appl. No.: 10/899,625

(22) Filed: Jul. 26, 2004

(65) Prior Publication Data

US 2005/0101551 A1 May 12, 2005

Related U.S. Application Data

(63) Continuation-in-part of application No. PCT/GB03/00304, filed on Jan. 27, 2003.

(30) Foreign Application Priority Data

| Jan. 25, 2002 | (GB) | ................. | 0201849.7 |
| Jan. 28, 2002 | (GB) | ................. | 0201919.8 |
| May 29, 2002 | (GB) | ................. | 0212438.6 |

(51) Int. Cl.
| A61K 31/70 | (2006.01) |
| C07H 19/16 | (2006.01) |
| C07H 19/167 | (2006.01) |

(52) U.S. Cl. .................... 514/46; 536/27.23; 536/27.62
(58) Field of Classification Search .................. 514/46; 536/27.23, 27.62
See application file for complete search history.

(56) References Cited

U.S. PATENT DOCUMENTS

| 5,506,347 A | 4/1996 | Erion et al. |
| 5,573,772 A | 11/1996 | Downey et al. |
| 5,646,128 A | 7/1997 | Firestein et al. |
| 5,658,889 A | 8/1997 | Gruber et al. |
| 5,674,998 A | 10/1997 | Boyer et al. |
| 5,864,033 A | 1/1999 | Browne et al. |
| 6,048,865 A | 4/2000 | Baraldi et al. |
| 2005/0101551 A1 * | 5/2005 | Sevillano et al. ............... 514/45 |

FOREIGN PATENT DOCUMENTS

| EP | 0 277 917 A2 | 8/1988 |
| EP | 0 704 215 A2 | 4/1996 |

(Continued)

(Continued)

OTHER PUBLICATIONS

V et al., *Chinese Journal of Medicinal Chemistry* 8(2):116-121, 1998.
Muller, *Current Medical Chemistry* 7(12):1269-1288, 2000.

*Primary Examiner*—L. E. Crane
(74) *Attorney, Agent, or Firm*—Klarquist Sparkman, LLP

(57) ABSTRACT

Adenosine analogue-type A3 receptor agonists having the formula wherein
D is N or CH;
E is O;
$X^1$ is a group of the formula —$CR^{20}R^{21}$-CYCLE, where $R^{20}$ and $R^{21}$ are the same or different and are H, F or $CH_3$; CYCLE is

V where G is N, CH, CF, $CCH_3$ or $CCF_3$,
M is H,
Y is —O— or N=, and
Z is —N= when Y is O, or is O when Y is —N=;
$R^5$ is H, $CH^3$, I, Br, Cl, $CF_3$, OH or $NH_2$; and
$R^8$ is —$NR^9R^{10}$, —$CHR^9R^{10}$ or —$N=CR^9R^{10}$, where $R^9$ and $R^{10}$ are the same and are $C_1$-$C_4$ alkyl, $C_1$-$C_4$ alkenyl or $C_1$-$C_4$ alkoxyalkyl
$X^2$ is mono-N— or di-N,N—($C_1$-$C_4$)alkylaminocarbonyl, mono-N—or di-N,N—($C_3$-$C_5$)cycloalkyl-aminocarbonyl or N-($C_1$-$C_4$)alkyl-N-($C_3$-$C_5$)cycloalkylamino-carbonyl;
$X^3$ is OH or NH2;
$X^4$ is OH;
$X^5$ is H , halogen, ($C_1$-$C_{10}$)alkyl , ($C_2$-$C_{10}$)alkenyl , ($C_2$-$C_{10}$)alkynyl , or either of the latter two groups where terminally substituted by an aryl or heteroaryl group and, when having a terminal methyl group, optionally further terminally substituted by hydroxyl. The compounds may be used alone or with a pharmaceutically acceptable carrier or diluent to stimulate adenosine $A_3$ receptors.

27 Claims, 10 Drawing Sheets

FOREIGN PATENT DOCUMENTS

| | | |
|---|---|---|
| EP | 1 186 304 A2 | 3/2002 |
| EP | 1 241 176 A1 | 9/2002 |
| WO | WO 86/00310 | 1/1986 |
| WO | WO 92/05177 | 4/1992 |
| WO | WO 93/23418 | 11/1993 |
| WO | WO 95/02604 | 1/1995 |
| WO | WO 95/07921 | 3/1995 |
| WO | WO 95/28160 | 10/1995 |
| WO | WO 96/12496 | 5/1996 |
| WO | WO 96/14060 | 5/1996 |
| WO | WO 98/16539 | 4/1998 |
| WO | WO 98/50047 | 11/1998 |
| WO | WO 99/02143 | 1/1999 |
| WO | WO 99/13721 | 3/1999 |
| WO | WO 99/20284 | 4/1999 |
| WO | WO 00/23447 | 4/2000 |
| WO | WO 00/25758 | 5/2000 |
| WO | WO 01/19360 A2 | 3/2001 |
| WO | WO 01/23399 A1 | 4/2001 |
| WO | WO 01/60835 A1 | 8/2001 |
| WO | WO 01/77075 A2 | 10/2001 |
| WO | WO 02/055085 A2 | 7/2002 |
| WO | WO 02/055521 A1 | 7/2002 |
| WO | WO 02/066020 A2 | 8/2002 |
| WO | WO 02/083152 A1 | 10/2002 |
| WO | WO 02/089807 A1 | 11/2002 |

* cited by examiner

Figure 1 Reaction scheme for the synthesis of the 2-picolyl reactant.

Figure 2  Reaction scheme for the synthesis of the 2-alkenyl substituted compounds of the invention.

Figure 3  Reaction scheme for synthesis of the benzoxazole reactant.

Figure 4     Reaction scheme for the synthesis of compounds in accordance with the second embodiment of the invention.

Figure 5  Reaction scheme for synthesis of 2-alkynyl substituted compounds of the invention.

Figure 6  Graph of percentage relaxation of guinea pig atria (precontracted with carbachol) against $\log_{10}$ of concentration (M) of compound 6 (diamond) and IB-NECA (square) agonists.

Figure 7  Graph of percentage relaxation of guinea pig trachea (precontracted with carbachol) against $\log_{10}$ of concentration (M) of compound 6 (diamond) and IB-NECA (square) agonists.

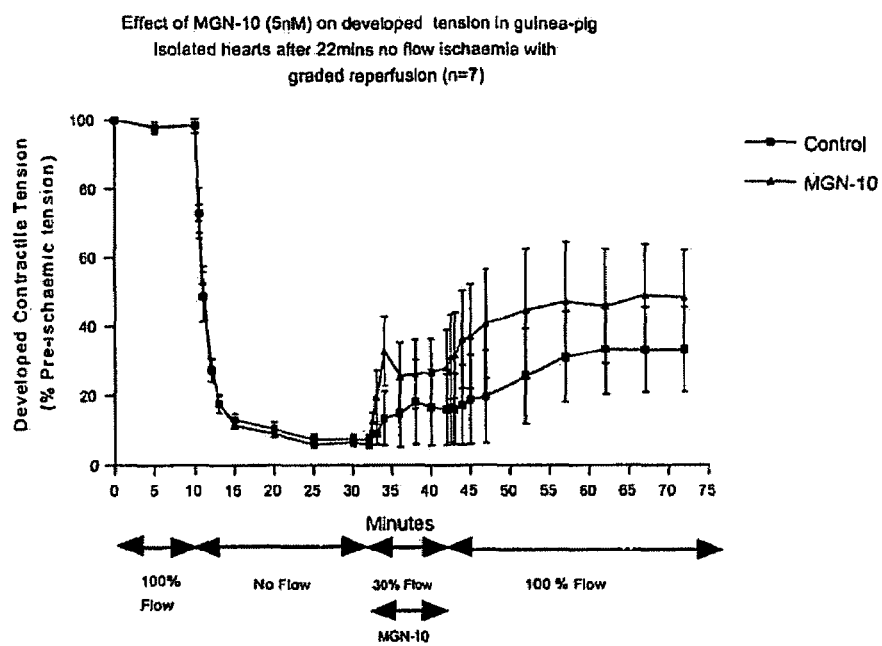
Figure 9 Developed tension in guinea-pig isolated hearts after 22 minutes no flow ischaemia with graded reperfusion, with 5nM MGN-10

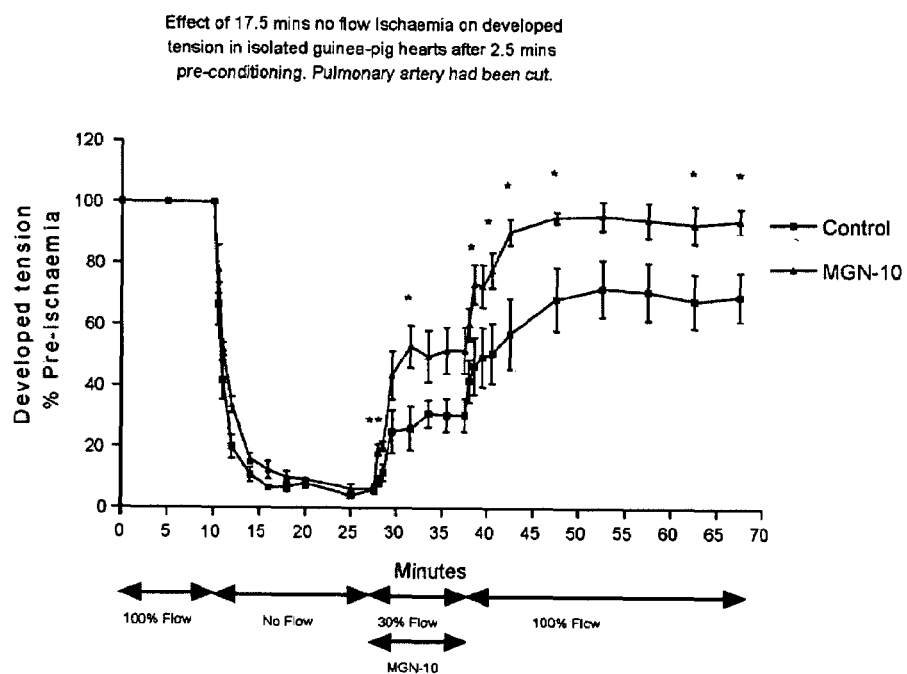
Figure 10 Developed tension in guinea-pig isolated hearts after 17.5 minutes no flow ischaemia after 2.5 minutes preconditioning, with 5nM MGN-10. The Pulmonary artery had been cut out

COMPOUNDS USEFUL AS A₃ ADENOSINE RECEPTOR AGONISTS

PRIORITY CLAIM

This application is a continuation-in-part of International Application No. PCT/GB03/00304, with an international filing date of Jan. 27, 2003, which was published in English under PCT Article 21(2), which in turn claims the benefit of Great Britain Patent Application No. 0201849.7, filed Jan. 25, 2002, Great Britain Patent Application No. 0201919.8, filed Jan. 28, 2002, and Great Britain Patent Application No. 0212438.6, filed May 29, 2002, all of which are incorporated by reference herein in their entireties.

FIELD OF THE INVENTION

This invention relates to compounds useful as $A_3$ adenosine receptor agonists and methods of selectively activating an $A_3$ adenosine receptor in a mammal, particularly a human. The present invention also relates to methods of treating various medical disorders with $A_3$ receptor agonists, in particular post-infarct patients, patients with severe angina and related cardiovascular disorders.

BACKGROUND OF THE INVENTION

Adenosine, an endogenous purine nucleoside, is ubiquitous in mammalian cell types. Adenosine present in the plasma and other extracellular fluids mediates many of its physiological effects via cell surface receptors and is an important regulatory species. Adenosine has the formula:

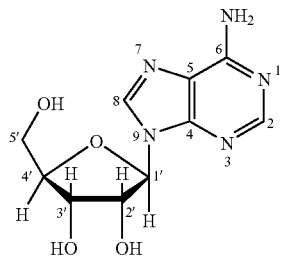

Adenosine receptors are generally divided into three major subclasses, A1, A2 and A3, on the basis of the differential affinities of a number of adenosine receptor agonists and antagonists for the receptors, their primary structures and the secondary messenger systems to which they couple.

Various adenosine A3 receptor agonists and uses therefor are taught in the prior art.

WO 95/02604 (the contents of which are incorporated herein by reference) discloses $A_3$ adenosine receptor agonists and their use as locomotor depressants, hypotensive agents, anxiolytic agents, cerebroprotectants and antiseizure agents.

U.S. Pat. No. 5,573,772 and related U.S. Pat. No. 5,443,836 claim the use of adenosine A3 agonists for applications where ischaemic preconditioning is beneficial, for example cardioprotection.

WO 98/50047 and WO 99/20284 also relate to ischaemic protection. WO 98/50047 claims methods of administering a compound having A3 agonist activity and a compound (whether the same compound or a different one) having A1 agonist activity or A2 antagonist activity. WO 99/20284 claims a method for preventing or reducing ischaemic heart damage by administration of at least two cardioprotectants, of which one may be an A3 agonist.

WO 01/19360 claims the use of A3 receptor agonists to achieve the following effect:

induce G-CSF secretion induce proliferation or differentiation of bone marrow or white blood cells prevent or treat leukopenia prevent or treat toxic side effects of a drug (e.g. drug-induce leukopenia or weight loss)

inhibiting abnormal cell growth treating cancer.

WO 01/083152 relates to the use of adenosine A3 receptor agonists to activate natural killer (NK) cells whilst WO 02/055085 teaches their use to inhibit viral replication.

WO 02/066020 proposes the use of adenosine A3 receptor agonists to modulate the activity of glycogen synthase kinase 3β.

Adenosine receptor ligands are described in the following documents:

U.S. Pat. No. 6,048,865 (A1 ligands)
WO 01/60835 (A2 antagonists)
WO 00/23447 (A1 and A2 ligands)
WO 92/05177 (A1/A2 agonists)
WO 92/05177 (A1/A2 agonists)
WO 95/28160 (A1/A2 agonists)
EP 277917 (A2 ligands)
WO 86/00310 (A2 ligands)
EP 1241176 (A3 agonists)
WO 01/23399 (A3 agonists)
WO 02/055521 (A2a antagonists)
WO 93/23418 (A1/A2 antagonists)
WO 95/07921 (A1 agonists)
WO 98/16539 (A1 ligands)
WO 02/055085 (A3 agonists)
WO 96/12496 (A1 agonist).

The article "Adenosine Receptor Ligands-Recent Developments Part I. Agonists", C. E. Muller, Current Medicinal Chemistry 2000, 7, 1269-1288 reports on the developments in the field of adenosine receptor agonists, including $A_3$ receptor agonists.

The above publications are all included herein by reference. The art therefore includes adenosine receptor agonists which are adenosine analogues characterised by specific variations which make the compounds capable of binding to and acting on one or more adenosine receptors. More particularly, the skilled person knows that there exists a class of adenosine analogue-type A3 receptor agonists.

Adenosine analogue-type A3 receptor agonists are familiar to the skilled reader and will require no further explanation to the skilled reader. Nonetheless, it may be of assistance to describe that adenosine analogue-type A3 receptor agonists may have an N6 nitrogen which may be identified with the N6 nitrogen of adenosine and is usually substituted by at least one substituent. Such agonists include without limitation compounds of the formula:

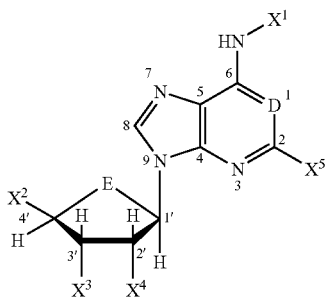

wherein

D is N or CH;

E is O, S or $CH_2$;

$X^1$ is an N6 substituent;

$X^2$ (the 4' substituent) is hydroxymethyl, $(C_1-C_3)$alkoxymethyl, $(C_3-C_5)$cycloalkoxy methyl, carboxy, $(C_1-C_3)$ alkoxycarbonyl, $(C_3-C_5)$cycloalkoxycarbonyl, 1,1-aminoiminomethyl, 1,1-(mono-N- or di-N,N—$(C_1-C_4)$ alkylamino)iminomethyl, 1, 1-(mono-N—or di-N,N—$(C_3-C_5)$cycloalkylamino)iminomethyl, carbamoyl, mono-N— or di-N,N—$(C_1-C_4)$alkylaminocarbonyl, mono-N— or di-N,N-$(C_3-C_5)$cycloalkylaminocarbonyl or N—$(C_1-C_4)$alkyl-N—$(C_3-C_5)$cycloalkylaminocarbonyl;

$X^3$ and $X^4$ are each independently hydrogen, alkyl, hydroxyalkyl, alkoxyalkyl, $OR^a$ $NR^aR^b$, where $R^a$ and $R^b$ are independently hydrogen (most preferably $X^3$ and $X^4$ are OH), alkyl, aralkyl, carbamoyl, alkyl carbamoyl, dialkylcarbamoyl, acyl, alkoxycarbonyl, aralkoxycarbonyl, aryloxycarbonyl, or, when $X^3$ and $X^4$ are both $OR^a$, the two $R^a$ groups together may form

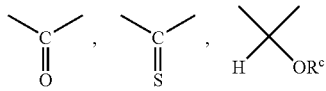

where $R^c$ is hydrogen or alkyl,

where $R^d$ and $R^e$ are independently hydrogen, alkyl, or together with the carbon atom to which they are attached may form a 1,1-cycloalkyl group;

$X^5$ is H, halogen, $(C_1-C_{10})$alkyl, fluorinated $(C_1-C_{10})$ alkyl (e.g. trifluoromethyl), $(C_1-C_{10})$ alkoxyalkyl, $(C_1-C_{10})$ alkoxy, $(C_1-C_{10})$alkylether, $(C_1-C_{10})$thioalkoxy, $(C_1-C_{10})$ alkylthio, amino, $(C_1-C_{10})$alkylamino, —$COX^6R^{25}$ where $X^6$ is O or NH and $R^{25}$ is $(C_1-C_4)$alkyl optionally terminally substituted by an aryl or a heteroaryl group [for example phenyl or a 5- or 6-membered heteroaryl group] and additionally or alternatively terminally substituted by hydroxy, $(C_2-C_{10})$alkenyl, $(C_2-C_{10})$alkynyl, or is $(C_2-C_{10})$ alkenyl or $(C_2-C_{10})$alkynyl in either case terminally substituted by an aryl or heteroaryl group [for example phenyl or a 5- or 6-membered heteroaryl group] and, when having a terminal methylic carbon atom, optionally further terminally substituted by hydroxy. Alkyl groups comprised in $X^5$ substituents are preferably linear.

Preferred values for the above-defined symbols are as follows:

D is N;

E is O;

$X^2$ is mono-N— or di-N,N(($C_1-C_4$) alkylaminocarbonyl, mono-N— or di-, N—$(C_3-C_5)$ cycloalkylaminocarbonyl or N—$(C_1-C_4)$ alkyl-N—$(C_3-C_5)$ cycloalkylaminocarbonyl and especially mono-N—$(C_1-C_4)$ alkylaminocarbonyl;

$X^3$ is OH or $NH_2$;

$X^4$ is OH;

$X^5$ is H, halogen, (($C_1-C_{10}$) alkyl and especially $(C_1-C_4)$ alkyl, trifluoromethyl, $(C_2-C_{10})$ alkenyl, $(C_2-C_{10})$ alkynyl, or either of the latter two groups where terminally substituted as described above, $X^5$ more preferably being H, chloro, bromo, iodo, $(C_1-C_4)$ alkyl and especially methyl, or trifluoromethyl.

It will be appreciated that any one or more of D, E, $X^2$, $X^3$, $X^4$ and $X^5$ may be one of the preferred species listed above; most desirably all are preferred.

BRIEF DESCRIPTIONS OF THE INVENTION

The present invention provides an adenosine analogue-type A3 receptor agonist having an N6 nitrogen substituted by a group of the formula —$CR^{20}R^{21}$-CYCLE where $R^{20}$ and $R^{21}$ are the same or different and H, F or $CH_3$; CYCLE is:

(I) a 2-pyridyl, or an analogue thereof in which the C3 and/or C5 carbon atoms are replaced by nitrogen, optionally substituted at the 4-position with $CH_3$, I, Br, Cl, $CF_3$, OH or $NH_2$ and/or at the 6-position by $OR^{11}$, $CO_2R^{11}$, $COR^{11}$ or $CONR^{11}$ where $R^{11}$ is $C_2-C_4$ alkyl; or (II) A bicyclic (fused) heteroaromatic ring of the formula

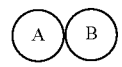

wherein ring A is a 5- or 6-membered ring characterised by the following features (in which ring positions are numbered relative to the linkage to —$CR^{20}R^{21}$—):

i. a carbon atom at the 1-position;

ii. carbon atom as CH or a nitrogen atom at position 2;

iii. it is 3, 4 fused to ring B;

iv. the 5-position ring atom is substituted by a moiety $R^5$ which is H, $CH_3$, I, Br, Cl, $CF_3$ or less preferably OH or $NH_2$;

v. if a 6-membered ring, it has at the 6-position a nitrogen, or —CM— where M is H, $CH_3$ or F;

ring B is a 5 or 6 membered ring characterised by the following features:

(a) an in-ring heteroatom including O, N or S joined to the 4-position of ring A;

(b) said in-ring heteroatom is joined within the ring secondly to a carbon which is substituted by a moiety $R^8$ which is H or another moiety wherein the number of atoms which are not hydrogen or halogen is no more than 10;

(c) an in-ring atom joined to the 3-position of ring A which is N, O, or less preferably S or C, said C being in the form of a CH or CO group;

(d) in the case of a 6-membered ring, the remaining ring member is nitrogen or carbon in the form of CH.

As discussed below, the products of the invention include any compound capable of resulting in the delivery of such agonists to adenosine A3 receptors in vivo and include, therefore, salts and prodrugs of such agonists as well as the salts of such prodrugs. In this application the term "product of the invention" is to be understood accordingly.

The invention includes but is not limited to adenosine-5'-uronamides which are N6-monosubstituted by $-CR^{20}R^{21}-$CYCLE. The uronamides may be ethyl or methyl uronamides. The adenosine-5'-uronamides may, for example, be 2-substituted by, amongst others, a small substituent such as Cl, Br, I, $CH_3$ or $CF_3$.

Two classes of compounds of the invention are of the formula I or II:

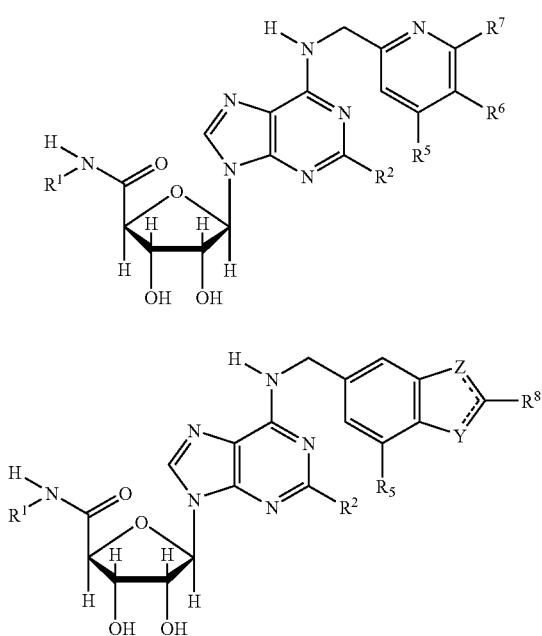

wherein:

$R^1$ is $C_1$-$C_4$ alkyl;

$R^2$ is selected from hydrogen, halo (e.g. fluoro, chloro, bromo or iodo), $CH_3$, $CF_3$, an alkynyl radical of the formula

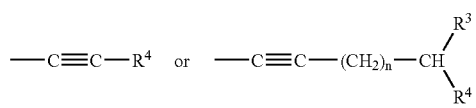

or an alkenyl radical of the formula

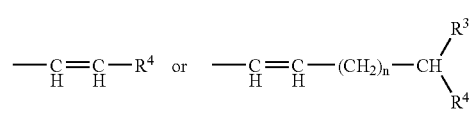

where n is 0 or an integer of from 1 to 4, $R^3$ is hydrogen or hydroxy, and $R^4$ is selected from methyl, a substituted or unsubstituted phenyl, a substituted or unsubstituted naphthyl or Het where Het is a 5 or 6 membered heterocyclic aromatic or non-aromatic ring, optionally benzocondensed, containing 1 to 3 heteroatoms selected from oxygen, sulfur and nitrogen linked through a carbon atom or through a nitrogen atom;

$R^5$ is selected from hydrogen, halo, methyl and $CF_3$; and $R^6$ is selected from hydrogen or amino;

$R^7$ is selected from hydrogen, $-OR^{11}$, $-CO^2R^{11}$, $-COR^{11}$ and $-CONR^{11}$ where $R^{11}$ is $C_{1-4}$ alkyl;

or $R^6$ and $R^7$, when taken together with the carbon atoms to which they are attached, form an oxazole ring in which the carbon between the oxygen and the nitrogen of the oxazole may optionally be substituted by an amine group having the formula $-NR^9R^{10}$ where each of $R^9$ and $R^{10}$ which may be the same or different is hydrogen, a $C_1$-$C_4$ alkyl radical or a $C_1$-$C_4$ alkenyl;

$R^8$ is H or $-NR^9R^{10}$ in which $R^9$ and $R^{10}$ which may be the same or, less preferably, different, are selected from hydrogen, a $C_1$-$C_4$ alkyl radical, a $C_1$-$C_4$ alkenyl radical or a $C_1$-$C_4$ alkoxyalkyl radical, $R^8$ is $-CHR^9R^{10}$ or $-N=CR^9R^{10}$ wherein $R^9$ and $R^{10}$ are as previously defined $OR^{11}$ or $SR^{11}$ wherein $R^{11}$ is as previously defined;

one of Y and Z is nitrogen and the other of Y and Z is oxygen; and

where Z is nitrogen and Y is oxygen and

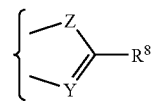

where Z is oxygen and Y is nitrogen.

Preferably $R^9$ and $R^{10}$ are the same.

Of the formula I and formula II compounds, most preferred are the oxazole compounds of formula I and the compounds of formula II.

The present invention also provides a pharmaceutical composition comprising a pharmaceutically acceptable carrier and an effective amount, e.g. a therapeutically effective amount, including a prophylactically effective amount, of one or more products of the invention.

In addition, the present invention provides a method of selectively activating $A_3$ adenosine receptors in a mammal, which method comprises acutely or chronically administering to a mammal in need of selective activation of its $A_3$ adenosine receptors a therapeutically effective amount, including a prophylactically effective amount, of one or more products of the invention.

BRIEF DESCRIPTION OF THE DRAWINGS

FIG. 9 is a graph showing the developed tension in guinea-pig isolated hearts after 22 minutes no flow ischaemia with graded reperfusion, with 5nM MGN-10.

FIG. 10 is a graph showing the developed tension of guinea-pig isolated hearts after 17.5 minutes no flow ischaemia after 2.5 minutes preconditioning, with 5nM MGN-10. The pulmonary artery has been cut out.

DETAILED DESCRIPTION OF THE INVENTION

Figure 1:
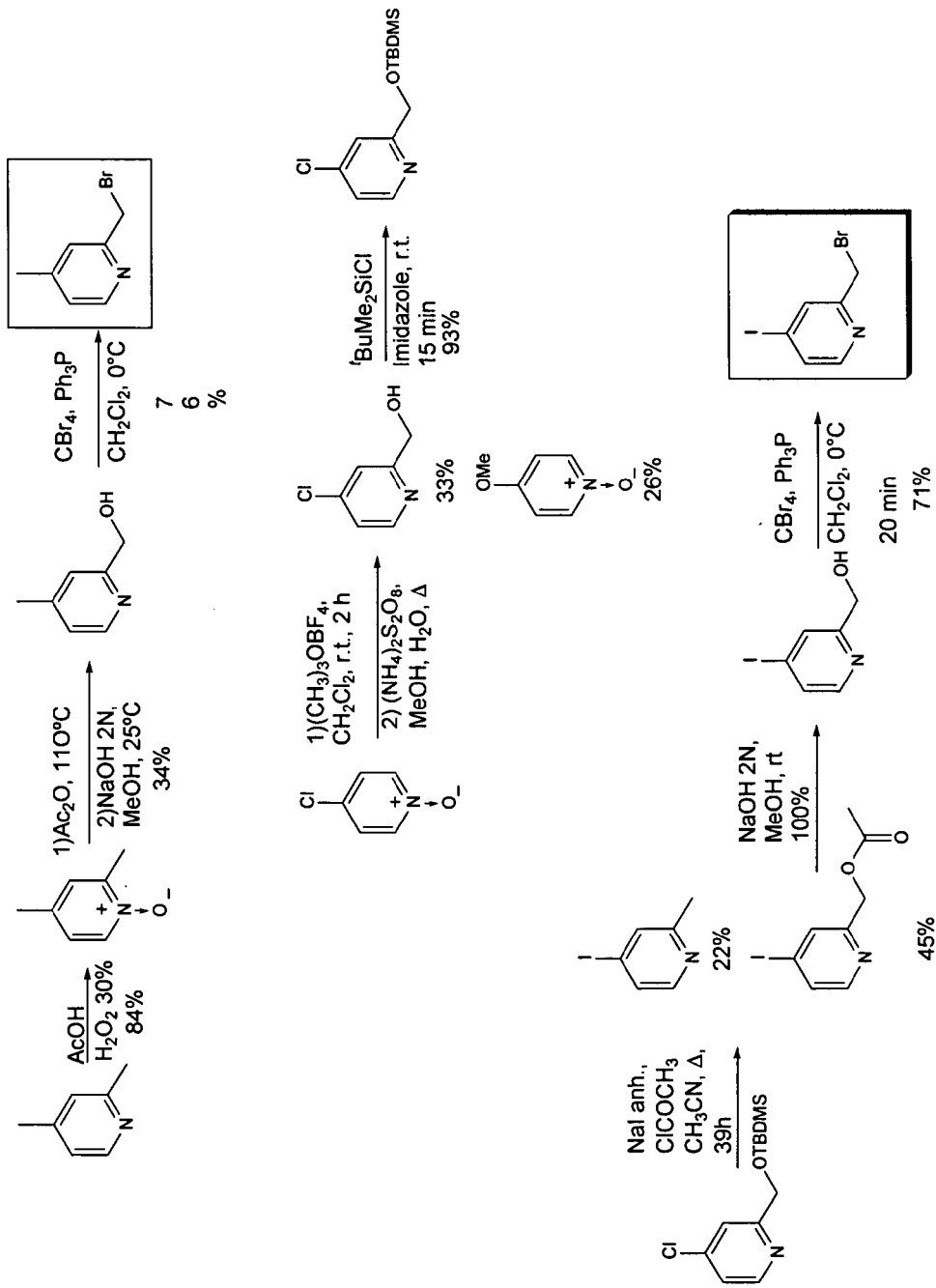
FIG. 1 is a reaction scheme for the synthesis of the 2-picolyl reactant.

The present invention provides in one aspect adenosine A3 receptor agonists having a normally mono-substituted N6 nitrogen wherein the substituent is —$CR^{20}R^{21}$-CYCLE where $R^{20}$ and $R^{21}$ are the same or different and H, F and $CH_3$;

and CYCLE is:

(I) a 2-pyridyl, or an analogue thereof in which the C3 and/or C5 carbon atoms are replaced by nitrogen, optionally substituted at the 4-position with $CH_3$, I, Br, Cl, $CF_3$, OH or $NH_2$ and/or at the 6-position by $OR^{11}$ 1, $CO_2R^{11}$, $COR^{11}$ or $CONR^{11}$ where $R^{11}$ is $C_1$-$C_4$ alkyl; or (II) a bicyclic (fused) heteroaromatic ring of the formula

wherein
ring A is a 5- or 6-membered ring characterised by the following features (in which ring positions are numbered relative to the linkage to —$CR^{20}R^{21}$—):

i. a carbon atom at the 1-position;
ii. carbon atom in the form of CH or a nitrogen atom at position 2;
iii. it is 3, 4 fused to ring B;
iv. the 5-position ring atom is substituted by a moiety $R^5$ which is H, $CH_3$, I, Br, Cl, $CF_3$ or less preferably OH or $NH_2$;
v. if a 6-membered ring, it has at the 6-position a nitrogen, or —CM- where M is H, $CH_3$ or F, of which F and especially H are preferred;

ring B is a 5 or 6 membered ring characterised by the following features:

(a) an in-ring heteroatom including O, N or S joined to the 4-position of ring A;
(b) said in-ring heteroatom is joined within the ring secondly to a carbon which is substituted by a moiety $R^8$ which is H or another moiety wherein the number of atoms which are not hydrogen or halogen is no more than 10;
(c) an in-ring atom joined to the 3-position of ring A which is N, O, or less preferably S or C, said C being in the form of a CH or CO group;
(d) in the case of a 6-membered ring, the remaining ring member is nitrogen or carbon in the form of CH. The products of the invention further include variant forms of the agonists as discussed next.

The disclosed compounds can exist in different forms, such as salts and esters, for example, and the invention includes all variant forms of the compounds. In particular, the compounds may be in the form of acid addition salts which, for those compounds for pharmaceutical use, will be pharmaceutically acceptable. Exemplary acids include HBr, HCl and $HSO_2CH_3$.

Certain compounds of the invention exist in different tautomeric forms and the invention includes all such tautomers. Compounds in which ring B contains an imidazole ring are tautomeric and, in the case of such compounds, it is highly desirable that more than 50% of the molecule is in the form of the isomer in which the nitrogen atom on the same side of CYCLE as $R^5$ (the nitrogen atom joined to the 4-position of ring A should be in the unprotonated form —N=. More desirably, at least 75%, e.g. at least 90% of the compound is in this form.

The invention includes prodrugs for the active pharmaceutical species of the invention, for example in which one or more functional groups are protected or derivatised but can be converted in vivo to the functional group, as in the case of esterified hydroxy groups, for example. The term "prodrug," as used herein, represents compounds which are transformed in vivo to the parent compound, for example, by hydrolysis in blood. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and Judkins, et al. Synthetic Communications, 26(23), 4351-4367 (1996), each of which is incorporated herein by reference. The term "prodrug" is to be widely interpreted and includes, inter alia, salts of covalent prodrug molecules.

The use of protecting groups is fully described in 'Protective Groups in Organic Chemistry', edited by J W F McOmie, Plenum Press (1973), and 'Protective Groups in Organic Synthesis', 2nd edition, T W Greene & P G M Wutz, Wiley-Interscience (1991).

Thus, it will be appreciated by those skilled in the art that, although protected derivatives of compounds of the invention may not possess pharmacological activity as such, they may be administered, for example parenterally or orally, and thereafter metabolised in the body to form compounds of the invention which are pharmacologically active. Such derivatives and their salts are therefore examples of "prodrugs". All prodrugs of the described compounds are included within the scope of the invention.

The pharmaceutically acceptable salts of the present invention can be synthesized from the parent compound (active compound or prodrug) which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., US, 1985, p. 1418, the disclosure of which is hereby incorporated by reference.

The invention thus includes pharmaceutically-acceptable salts of the disclosed compounds and their covalent prodrug molecules wherein the parent compound is modified by making acid or base salts thereof, for example the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The phrase "pharmaceutically acceptable" is employed herein to refer to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio.

Geometric isomers may exist in the products of the present invention. The present invention contemplates the various geometric isomers and mixtures thereof resulting from the arrangement of substituents around a carbon—carbon double bond and designates such isomers as of the Z or E configuration, wherein the term "Z" represents substituents on the same side of the carbon—carbon double bond and the term "E" represents substituents on opposite sides of the carbon—carbon double bond.

The invention therefore includes all variant forms of the defined compounds, for example any substance which, upon administration, is capable of providing directly or indirectly a compound as defined above or providing a species which is capable of existing in equilibrium with such a compound.

The term "heteroaromatic ring" refers to a ring system which has at least one (e.g. 1, 2 or 3) in-ring heteroatoms and has a conjugated in-ring double bond system. The term "heteroatom" includes oxygen, sulfur and nitrogen, of which sulfur is less preferred. Examples of such heteroaromatic rings can be seen in CYCLE moieties 1) to 10) below. Such rings are substantially planar.

The term "alkyl" in this specification includes linear and branched alkyl groups, for example methyl, ethyl, n-propyl, iso-propyl, tert-butyl, n-pentyl and n-hexyl. Similarly, the term "alkoxy" includes groups of which the alkyl part may be linear or branched, for example one of those groups listed in the preceding sentence; alkylene groups may likewise be linear or branched and may, for example, correspond to one of those alkyl groups listed in the preceding sentence. The alkyl groups may be (but preferably are not) interrupted by one or more ether linkages.

The term "halogen" herein includes reference to F, Cl, Br and I, of which Cl is often preferred.

It will be understood that the invention specifically includes variants of preferred or exemplary compounds in which one or more moieties (e.g. substituents) have been replaced by alternatives described in this application.

Throughout the description and claims of this specification, the words "comprise" and "contain" and variations of the words, for example "comprising" and "comprises", means "including but not limited to", and is not intended to (and does not) exclude other moieties, additives, components, integers or steps.

Reverting now to the adenosine A3 receptor agonists having an N6 substituent —$CR^{20}R^{21}$-CYCLE, preferred substituents have one or more (and desirably all of) the following features:

$R^{20}$ and $R^{21}$ are both the same and/or are H or F (usually both are H)

A is a 6-membered ring and B is a 5-membered ring $R^5$ is preferably not H and is more usually —$CH_3$, I or Br or less preferably —$CF_3$ or Cl $R^8$ is H, —$R^9$, —$OR^9$, —$SR^9$, —$COR^9$, or more preferably —$NO_2$, —$NR^9R^{10}$—$CHR^9R^{10}$, —$N$=$CR^9R^{10}$ where $R^9$ and $R^{10}$ are the same, or less preferably different, and are $C_1$-$C_4$ alkyl, $C_1$-$C_4$ alkenyl or $C_1$-$C_4$ alkoxyalkyl and most preferably ethyl or especially methyl CYCLE is a bicyclic ring and more usually a structure of formula (V)

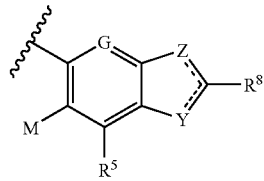

V where

G is N, CH, CF, $CCH_3$ or less preferably $CCF_3$;

M is preferably but not necessarily H;

Y is O, =N— or less preferably S, when Y is O, S, Z is =N— or less preferably =CH— when Y is =N—, Z is O, NH, or less preferably S.

The most preferred $R^8$ groups are —$CHR^9R^{10}$, —$N$=$CR^9R^{10}$ and most especially —$NR^9R^{10}$.

Preferably the 5-membered ring is an oxazole and more preferably Y is O and Z is =N—.

As examples of CYCLE moieties may be mentioned:

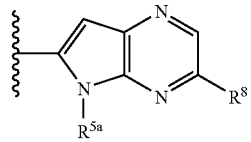

1)

-continued

2)
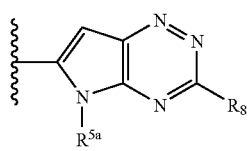

3)
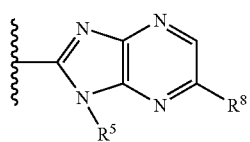

4)
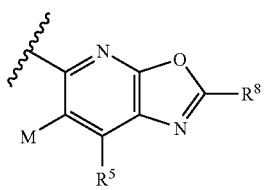

5)
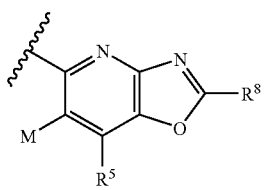

6)
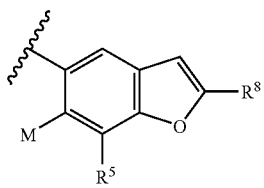

7)
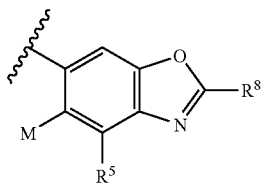

8)
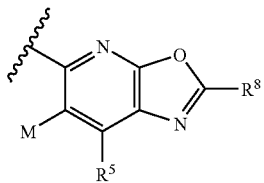

9)
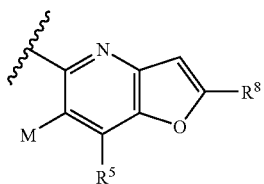

-continued

10)
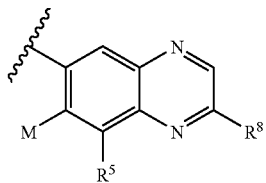

In the above structures $R^{5a}$ is $CH_3$ or less preferably $CF_3$.

In principle, any ring A shown above may be fused with any ring B shown above (e.g. ring A of structure 5 may be fused with ring B of structures 2, 6 or 10), e.g. to form a 5/6 (ring A is 5-membered, ring B 6-membered), 6/6 or 6/5 fused ring. Structures 7 and 8 are particularly preferred CYCLE moieties.

In some adenosine A3 receptor agonists of the invention, CYCLE is as shown in Formula (I) or Formula (II) (see above, under the heading "Brief Description of the Invention"). In all the agonists of the invention —$CR^{20}R^{21}$ is preferably —$CH_2$—.

A preferred class of compounds of the invention have a 4' substituent of the formula:

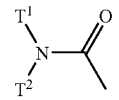

where $T^1$ and $T^2$ are each the same or different and are hydrogen or $C_1$-$C_4$ alkyl. Most preferably, $T^1$ is $C_1$, $C_2$, $C_3$ or $C_4$ alkyl and $T^2$ is H. A particularly preferred alkyl group is methyl.

Another preferred class of compounds have a C2 substituent which is H, halogen, —$CH_3$, —$CF_3$, —C≡C—$R^4$, —C≡C—$(CH_2)_n$—$CHR^3R^4$, —CH=CH—$R^4$ or —CH=CH—$(CH_2)_n$—$CHR^3R^4$, where n is from 0 to 4, $R^3$ is hydrogen or hydroxy, and $R^4$ is selected from methyl, a substituted or unsubstituted phenyl, a substituted or unsubstituted naphthyl or Het where Het is a 5 or 6 membered heterocyclic aromatic or non-aromatic ring, optionally benzocondensed, containing 1 to 3 heteroatoms selected from oxygen, sulfur and nitrogen linked through a carbon atom or through a nitrogen atom. The C2 substituent is hydrogen in some preferred compounds. In other preferred compounds the C2 substituent is halogen, —$CH_3$ or —$CF_3$ and especially chloro.

In another aspect, the invention provides compounds of formula (III)

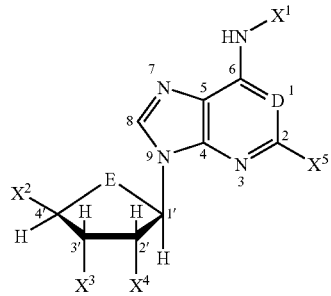

in which:

$X^1$ is —$CR^{20}R^{21}$-CYCLE as described above; and D, E, $X^2$, $X^3$, $X^4$ and $X^5$ are as described previously under the heading "Background of the Invention".

Particularly preferred are compounds of formula (IV)

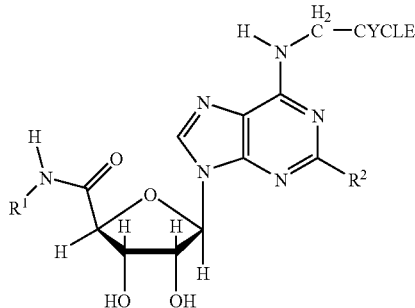

where $R^1$ and $R^2$ are as defined previously under the heading "Brief Description of the Invention" and CYCLE is as previously described and is most desirably a bicyclic ring as defined above. In some proposed formula IV compounds $R^1$ is preferably $C_1$-$C_4$ alkyl (e.g. ethyl or especially methyl), $R^2$ is preferably hydrogen, halo, methyl or trichloromethyl.

Whilst the formula I and II compounds are described above, preferred embodiments of those compounds will now be described by way of non-limiting example.

Thus, in preferred embodiments of the compounds of formulae I and II, $R^1$, $R^2$, $R^4$ and $R^5$ may be as follows:

Radical $R^1$

Preferably $R^1$ is methyl or ethyl, preferably methyl.

Radical $R^2$

Preferably $R^2$ is hydrogen, halogen, notably chloro, $CH_3$ or $CF_3$. Alternatively, $R^2$ may be an alkynyl radical of the formula

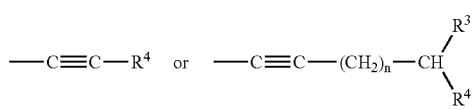

where n, $R^3$ and $R^4$ are as defined above. Preferably $R^3$ is hydrogen. Preferably $R^4$ is selected from methyl, unsubstituted phenyl or a heterocyclic moiety selected from pyridyl, thienyl, furyl, imidazolyl, thiazolyl, pyrazoyl, triazoyl, oxazole and isoxazole. Thienyl is the preferred heterocyclic radical. Examples of alkynyl radicals are —≡—$R^4$ in which $R^4$ is unsubstituted phenyl or thienyl; —≡—$(CH^2)_n$—$CHR^3R^4$ where n is 2, $R^3$ is hydrogen and $R^4$ is methyl or unsubstituted phenyl; and —≡—$(CH_2)_n$—$CHR^3R^4$ where n is O, $R^3$ is hydroxy and $R^4$ is phenyl.

Radical $R^4$

Where $R^4$ is a substituted phenyl or a substituted naphthyl, this may be substituted with from 1 to 3 substituents selected from halo (fluoro, chloro, bromo and iodo), $C_1$-$C_6$ alkyl, $C_1$-$C_6$ haloalkyl, $C_1$-$C_6$ alkoxy, $C_1$-$C_6$ haloalkoxy, $C_2$-$C_6$ alkoxycarbonyl, $C_2$-$C_6$ alkoxyalkyl, $C_1$-$C_6$ alkylthio, thio, CHO, cyanomethyl, nitro, cyano, hydroxy, carboxy, $C_2$-$C_6$ acyl, amino, $C_1$-$C_3$ monoalkylamino, $C_2$-$C_6$ dialkylamino, methylenedioxy; aminocarbonyl. The preferred halo is chloro. The preferred $C_1$-$C_6$ alkyl are methyl or ethyl. The preferred $C_1$-$C_6$ haloalkyl is trifluoromethyl. The preferred $C_1$-$C_6$ alkoxy are methoxy or ethoxy. The preferred $C_1$-$C_6$ haloalkoxy are trifluoromethoxy or difluoromethoxy. Tne preferrd $C_2$-$C_6$ alkoxycarbonyl are methoxycarbonyl or ethoxycarbonyl. The preferred $C_2$-$C_6$ alkoxyalkyl are methoxymethyl, methoxyethyl or ethoxymethyl. The preferred $C_1$-$C_6$ alkylthio is methylthio. The preferred $C_2$-$C_6$ acyl is acetyl. The preferred $C_1$-$C_3$ monoalkylamino are methylamino, ethylamino, isopropylamino. The preferred $C_2$-$C_6$ dialkylamino are dimethylamino, diethylamino, methylethylamino, methylisopropylamino, diisopropylamino.

Radical $R^5$

Preferably $R^5$ is selected from bromo, iodo and methyl. In one class of compounds, $R^5$ iodo or methyl; in first sub-class, $R^5$ is iodo and in a second sub-class $R^5$ is methyl. In another class of compounds $R^5$ is bromo.

Compounds of Formula I

In a first embodiment of compounds of formula I of the invention, $R^6$ and $R^7$ are not joined together to form an oxazole ring. In this embodiment, $R^6$ and $R^7$ may each be hydrogen. In another aspect of this embodiment, $R^6$ is hydrogen and $R^7$ is as defined above, preferably —$COR^{11}$ where $R^{11}$ is $C_{1-4}$ alkyl, for example methyl.

A preferred group of compounds of this embodiment has the formula:

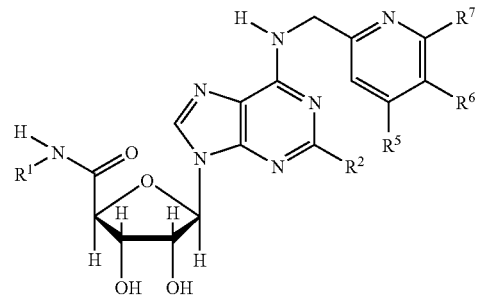

or a pharmaceutically acceptable salt thereof where $R^1$, $R^2$, and $R^5$ are as defined above, $R^6$ is hydrogen or amino, and $R^7$ is selected from hydrogen, —$OR^{11}$, —$CO_2R^{11}$, —$COR^{11}$ and —$CONR^{11}$ where $R^{11}$ is $C_{1-4}$alkyl.

Preferably $R^1$ is methyl or ethyl, more preferably methyl.

Preferably $R^2$ is hydrogen, halogen notably chloro, $CH_3$ or $CF_3$, less peferably $R^2$ is the formula

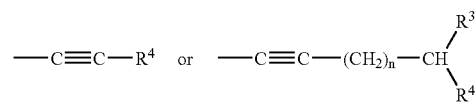

where n, $R^3$ and $R^4$ are as defined above. Preferably $R^3$ is hydrogen. Preferably $R^4$ is selected from methyl, unsubstituted phenyl or a heterocyclic moiety selected from pyridyl, thienyl, furyl, imidazolyl, thiazolyl, pyrazoyl and triazoyl. Thienyl is the preferred heterocyclic radical.

Preferably $R^5$ is selected from bromo, iodo and methyl. In one class of compounds $R^5$ is iodo or methyl; in first subclass, $R^5$ is iodo and in a second sub-class $R^5$ is methyl. In another class of compounds, $R^5$ is bromo.

In this group of compounds, $R^6$ and $R^7$ may each be hydrogen. Alternatively, $R^6$ may be hydrogen and $R^7$ be as defined above, preferably —$COR^{11}$ where $R^{11}$ is $C_{1-4}$ alkyl, for example methyl.

One preferred group of compounds within this aspect of the invention are those in which:

$R^1$ is methyl or ethyl, preferably methyl;

$R^2$ is H or halogen (e.g. chloro), $CH_3$, $CF_3$ or, less preferably, an alkynyl radical of the formula

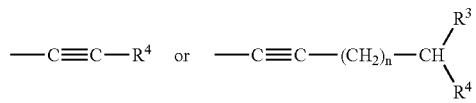

where n, $R^3$ are as defined above and $R^4$ is selected from methyl, unsubstituted phenyl or a heterocyclic moiety selected from pyridyl, thienyl, furyl, imidazolyl, thiazolyl, pyrazoyl and triazoyl.

$R^5$ is iodo or methyl or is bromo;

$R^6$ and $R^7$ are hydrogen.

$R^2$ may be —≡—$R^4$ in which $R^4$ is unsubstituted phenyl or thienyl; —≡—$(CH_2)_n$—$CHR^3R^4$ where n is 2, $R^3$ is hydrogen and $R^4$ is methyl or unsubstituted phenyl; and —≡—$(CH^2)_n$—$CHR^3R^4$ where n is O, $R^3$ is hydroxy and $R^4$ is phenyl.

Compounds of this aspect of the invention include:

$N^6$-(4-iodo-2-picolyl)-adenosine-5'-N-methyluronamide;
$N^6$-(4-methyl-2-picolyl)-adenosine-5'-N-methyluronamide;
$N^6$-(2-picolyl)-adenosine-5'-N-methyluronamide;
$N^6$-(6-acetyl-2-picolyl)-adenosine-5'-N-methyluronamide; and $N^6$-(4-iodo-2-picolyl)-2-(2-phenyl-1-ethynyl)-adenosine-5'-N-methyluronamide In a second and prefered embodiment of the compounds of formula I of the invention, $R^6$ and $R^7$ together with the carbon atoms to which they are attached form an optionally substituted oxazole ring, the compounds of this aspect of the invention have the following formula:

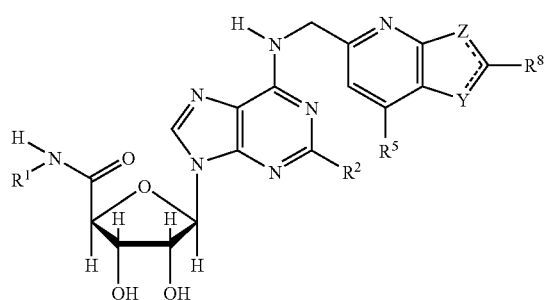

where $R^1$, $R^2$, and $R^5$ are as defined above under the heading "Brief Description of the Invention", one of Y and Z is oxygen and the other of Y and Z is nitrogen, and $R^8$ is as defined above under the heading "Brief Description of the Invention" as defined above and where

 represents 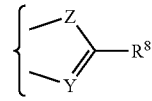

where Z is nitrogen and Y is oxygen and where Y is nitrogen and Z is oxygen.

Preferably $R^1$ is methyl or ethyl, preferably methyl.

Preferably $R^2$ is hydrogen, or halogen, notably chloro, $CH_3$ or $CF_3$. Alternatively, $R^2$ may be an alkynyl radical of the formula

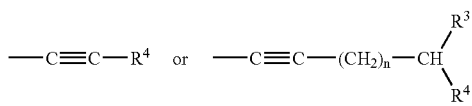

where n, $R^3$ and $R^4$ are as defined above. Preferably $R^3$ is hydrogen. Preferably $R^4$ is selected from methyl, unsubstituted phenyl or a heterocyclic moiety selected from pyridyl, thienyl, furyl, imidazolyl, thiazolyl, pyrazoyl and triazoyl. Thienyl is the preferred heterocyclic radical.

Preferably $R^5$ is selected from bromo, iodo and methyl In one class of compounds $R^5$ is iodo or methyl; in first subclass, $R^5$ is iodo and in a second sub-class $R^5$ is methyl. In another class of compounds $R^5$ is bromo.

Preferably $R^8$ is —$NR^9R^{10}$ where each of $R^9$ and $R^{10}$ is the same and is selected from $C_1$-$C_4$ alkyl, $C_1$-$C_4$ alkenyl or $C_1$-$C_4$ alkoxyalkyl, for example methyl, ethyl or —$CH_2$—$CH$=$CH_2$. In one aspect, Y is oxygen and Z is nitrogen and in another, Y is nitrogen and Z is oxygen. It is presently preferred that Y is O and Z is N.

One preferred group of compounds within this aspect of the invention are those in which:

$R^1$ is methyl or ethyl, preferably methyl;

$R^2$ is H, halogen (e.g. chloro) $CH_3$ or $CF_3$, or less preferably is an alkynyl radical of the formula

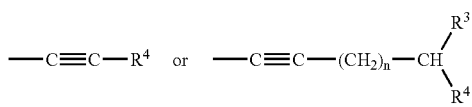

where n, $R^3$ are as defined above and $R^4$ is selected from methyl, unsubstituted phenyl or a heterocyclic moiety selected from pyridyl, thienyl, furyl, imidazolyl, thiazolyl, pyrazoyl and triazoyl (e.g. $R^2$ may be —≡—$R^4$ in which $R^4$ is unsubstituted phenyl or thienyl; —≡—$(CH_2)_n$—$CHR^3R^4$ where n is 2, $R^3$ is hydrogen and $R^4$ is methyl or unsubstituted phenyl; and —≡—$(CH_2)_n$—$CHR^3R^4$ where n is O, $R^3$ is hydroxy and $R^4$ is phenyl).

$R^5$ is iodo, chloro, bromo or methyl;

$R^8$ is —$NR^9R^{10}$ where each of $R^9$ and $R^{10}$ is the same and is selected from methyl, ethyl or —$CH_2$—$CH$=$CH_2$; and Y is O and Z is N.

In one class of compounds $R^5$ is iodo or methyl.

In another class of compounds $R^5$ is bromo.

It is preferred that $R^2$ is H or halo.

Compounds of Formula II

In accordance with a first embodiment of compounds of formula II of the invention, there is provided a group of compounds having the formula:

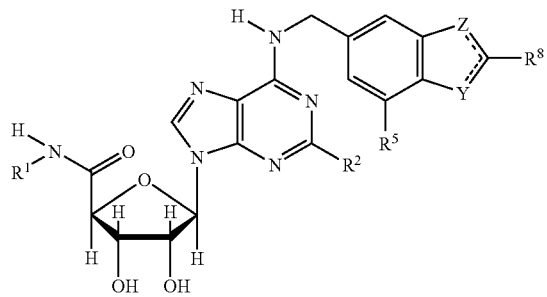

wherein:

$R^1$ is $C_1$-$C_4$ alkyl;

$R^2$ is hydrogen, halo (e.g. chloro, bromo or iodo) $CH_3$ or $CF_3$, or less preferably is an alkynyl radical of the formula

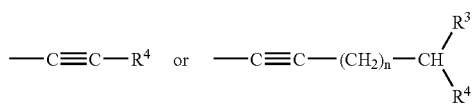

or an alkenyl radical of the formula

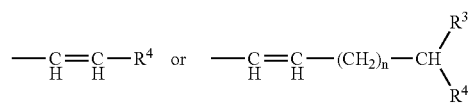

where n is 0 or an integer of from 1 to 4, $R^3$ is hydrogen or hydroxy, and $R^4$ is selected from methyl, a substituted or unsubstituted phenyl, a substituted or unsubstituted naphthyl or Het where Het is a 5 or 6 membered heterocyclic aromatic or non-aromatic ring, optionally benzocondensed, containing 1 to 3 heteroatoms selected from oxygen, sulfur and nitrogen linked through a carbon atom or through a nitrogen atom;

$R^5$ is selected from hydrogen, halo, methyl or less preferably $CF_3$; and $R^8$ is as defined above under the heading "Brief Description of the Invention", e.g. is H or —$NR^9R^{10}$ in which $R^9$ and $R^{10}$ which may be the same or different, are selected from hydrogen, a $C_1$-$C_4$ alkyl radical or a $C_1$-$C_4$ alkenyl radical;

one of Y and Z is nitrogen and the other of Y and Z is oxygen; and

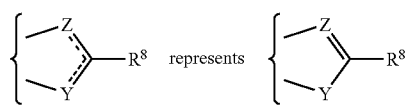

where Z is nitrogen and Y is oxygen and

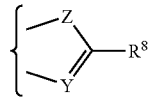

where Y is nitrogen and Z is oxygen.

Where $R^4$ is a substituted phenyl or a substituted naphthyl, this may be with from 1 to 3 substituents selected from halo (fluoro, chloro, bromo and iodo), $C_1$-$C_6$ alkyl, $C_1$-$C_6$ haloalkyl, $C_1$-$C_6$ alkoxy, $C_1$-$C_6$ haloalkoxy, $C_2$-$C_6$ alkoxycarbonyl, $C_2$-$C_6$ alkoxyalkyl, $C_1$-$C_6$ alkylthio, thio, CHO, cyanomethyl, nitro, cyano, hydroxy, carboxy, $C_2$-$C_6$ acyl, amino, $C_1$-$C_3$ monoalkylamino, $C_2$-$C_6$ dialkylamino, methylenedioxy; aminocarbonyl. The preferred halo is chloro. The preferred $C_1$-$C_6$ alkyl are methyl or ethyl. The preferred $C_1$-$C_6$ haloalkyl is trifluoromethyl. The preferred $C_1$-$C_6$ alkoxy are methoxy or ethoxy. The preferred $C_1$-$C_6$ haloalkoxy are trifluoromethoxy or difluoromethoxy. The preferred $C_2$-$C_6$ alkoxycarbonyl are methoxycarbonyl or ethoxycarbonyl. The preferred $C_2$-$C_6$ alkoxyalkyl are methoxymethyl, methoxyethyl or ethoxymethyl. The preferred $C_1$-$C_6$ alkylthio is methylthio. The preferred $C_2$-$C_6$ acyl is acetyl. The preferred $C_1$-$C_3$ monoalkylamino are methylamino, ethylamino, isopropylamino. The preferred $C_2$-$C_6$ dialkylamino are dimethylamino, diethylamino, methylethylamino, methylisopropylamino, diisopropylamino.

Preferably $R^1$ is methyl or ethyl, preferably methyl.

Preferably $R^2$ is hydrogen, halogen, notably chloro, $CH_3$ or $CF_3$. Alternatively, $R^2$ is an alkynyl radical of the formula

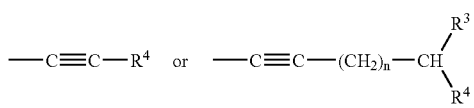

where n, $R^3$ and $R^4$ are as defined above. Preferably $R^3$ is hydrogen. Preferably $R^4$ is selected from methyl, unsubstituted phenyl or a heterocyclic moiety selected from pyridyl, thienyl, furyl, imidazolyl, thiazolyl, pyrazoyl and triazoyl. Thienyl is the preferred heterocyclic radical. Examples of alkynyl radicals are —≡—$R^4$ in which $R^4$ is unsubstituted phenyl or thienyl; —≡—$(CH_2)_n$—$CHR^3R^4$ where n is 2, $R^3$ is hydrogen and $R^4$ is methyl or unsubstituted phenyl; and —≡—$(CH^2)_n$—$CHR^3R^4$ where n is 0, $R^3$ is hydroxy and $R^4$ is phenyl.

Preferably $R^5$ is selected from bromo, iodo and methyl. In one class of compounds, $R^5$ is iodo or methyl; in first subclass, $R^5$ is iodo and in a second sub-class $R^5$ is methyl. In another class of compounds, $R^5$ is bromo.

Preferably $R^8$ is —$NR^9R^{10}$ where each of $R^9$ and $R^{10}$ is the same and is selected from hydrogen, and, more preferably, $C_1$-$C_4$ alkyl, $C_1$-$C_4$ alkenyl or $C_1$-$C_4$ alkoxyalkyl, for example methyl, ethyl or —$CH_2$—CH=$CH_2$. Most preferably, each of $R^9$ and $R^{10}$ is methyl.

In one aspect of this embodiment, Y is oxygen and Z is nitrogen and in another aspect, Y is nitrogen and Z is oxygen. It is presently preferred that Y is O and Z is N.

In one aspect, the invention concerns compounds in which:

$R^1$ is methyl or ethyl, preferably methyl;

$R^2$ is H, halo (e.g. Cl, Br or I), $CH_3$ or $CF_3$, or less preferably is an alkynyl radical of the formula

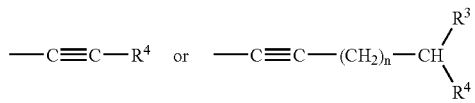

where n, $R^3$ are as defined above and $R^4$ is selected from methyl, unsubstituted phenyl or a heterocyclic moiety selected from pyridyl, thienyl, furyl, imidazolyl, thiazolyl, pyrazoyl and triazoyl (e.g. $R^2$ may be —≡—$R^4$ in which $R^4$ is unsubstituted phenyl or thienyl; —≡—$(CH_2)_n$—$CHR^3R^4$ where n is 2, $R^3$ is hydrogen and $R^4$ is methyl or unsubstituted phenyl; and —≡—$(CH_2)_n$—$CHR^3R^4$ where n is 0, $R^3$ is hydroxy and $R^4$ is phenyl).

$R^5$ is iodo, chloro, bromo or methyl; and $R^8$ is —$NR^9R^{10}$ where each of $R^9$ and $R^{10}$ is the same and is selected from hydrogen, methyl, ethyl or —$CH_2$—$CH=CH_2$.

In this aspect, it is preferred that Y is O and Z is N. It is also preferred that $R^2$ is hydrogen or halo.

In one class of compounds $R^5$ is iodo or methyl; in a first sub-class $R^5$ is iodo and in a second sub-class $R^5$ is methyl. In another class of compounds $R^5$ is bromo.

Compounds of this aspect of the present invention are:

$N^6$-[(2-dimethylamino-7-iodo-1,3-benzoxazol-5-yl)-methyl]-adenosine-5'-N-methyl uronamide;

$N^6$-[(2-Dimethylamino-1,3-benzoxazol-5-yl)-methyl]-adenosine-5'-N-methyluronamide; and $N^6$-[(2-dimethylamino-7-iodo-1,3-benzoxazol-5-yl)-methyl]-2-(2-phenyl-1-ethynyl)-adenosine-5'-N-methyluronamide.

The products of the invention are useful for treating mammals, especially a human (male or female) as described next.

Methods of Use

Another aspect of this invention, therefore, resides in methods of treating a mammal having a disease or condition mediated by an A3 adenosine receptor by administering a therapeutically effective amount of a product of the invention to the mammal.

In addition, the present invention provides a method of selectively activating $A_3$ adenosine receptors in a mammal, which method comprises acutely or chronically administering to a mammal in need of selective activation of its $A_3$ adenosine receptors a therapeutically effective amount, including a prophylactically effective amount, of a compound which binds with the $A_3$ receptor so as to stimulate an $A_3$ receptor-dependent response.

The method of the present invention has particular usefulness in in vivo applications. For example, $A_3$ adenosine receptor agonists can be used in the treatment of any disease, state or condition involving the release of cyclic adenosine monophosphate or the release of inositol-1,4,5-triphosphate (IP3), diacylglycerol (DAG), and free radicals and subsequent arachidonic acid cascades. Thus, high blood pressure, locomotor hyperactivity, hypertension, acute hypoxia, depression, and infertility can be treated in accordance with the present inventive method, wherein one of the above-described compounds is acutely administered, e.g., within about a few minutes to about an hour of the onset or realization of symptoms. The method also has utility in the treatment of chronic disease states and conditions, in particular those conditions and disease states wherein prophylactic or therapeutic administration of one of the above-described compounds will prevent the further onset of symptoms or will reduce recovery time. Examples of disease states and conditions that may be treated in accordance with the present inventive method include inflammatory disorders, such as vascular inflammation and arthritis, allergies, asthma, wound healing, stroke, cardiac infarct, cardiac failure, acute spinal cord injury, acute head injury or trauma, seizure, neonatal hypoxia (cerebral palsy; prophylactic treatment involves chronic exposure through placental circulation), hypoxia and chronic hypoxia due to arteriovenous malformations and occlusive cerebral artery disease, severe neurological disorders related to excitotoxicity, Parkinson's disease, Huntington's chorea, and other diseases of the central nervous system (CNS), cardiac disease, kidney disease, and contraception. Particular disease states which may be treated with the compounds of the invention are cardiac infarct and hypoxia.

Moreover, the above compounds may be used to treat malignant hypotension. For example, the administration of IB-MECA results in a significant increase (e.g., about 10-30%) in basal or systemic blood pressure (e.g., from about 70 mm Hg to about 90 mm Hg).

The above compounds may also be used to treat and/or protect against a variety of disorders, including, for example, seizures, transient ischemic shock, strokes, focal ischemia originating from thrombus or cerebral hemorrhage, global ischemia originating from cardiac arrest, trauma, neonatal palsy, hypovolemic shock, and hyperglycemia and associated neuropathies.

The present inventive method includes the administration to an animal, such as a mammal, particularly a human, in need of the desired $A_3$ receptor-dependent response of an effective amount, e.g., a therapeutically effective amount, of one or more of the aforementioned present inventive compounds or pharmaceutically acceptable salts or derivatives thereof, alone or in combination with one or more other pharmaceutically active compounds.

The compounds of the invention will normally be administered orally, intravenously, subcutaneously, buccally, rectally, dermally, nasally, tracheally, bronchially, by any other parenteral route, as an oral or nasal spray or via inhalation, The compounds may be administered in the form of pharmaceutical preparations comprising prodrug or active compound either as a free compound or, for example, a pharmaceutically acceptable non-toxic organic or inorganic acid or base addition salt, in a pharmaceutically acceptable dosage form. Depending upon the disorder and patient to be treated and the route of administration, the compositions may be administered at varying doses.

The most preferred routes of administration are injection and infusion, especially intravenous administration.

The compounds of the invention may be combined and/or co-administered with any antithrombotic agent, such as the antiplatelet agents acetylsalicylic acid, ticlopidine, clopidogrel, thromboxane receptor and/or synthetase inhibitors, fibrinogen receptor antagonists, prostacyclin mimetics and phosphodiesterase inhibitors and ADP-receptor ($P_2$ T) antagonists.

The compounds of the invention may be combined and/or co-administered with thrombolytics such as tissue plasminogen activator (natural, recombinant or modified), streptokinase, urokinase, prourokinase, anisoylated plasminogenstreptokinase activator complex (APSAC), animal salivary gland plasminogen activators, and the like, in the treatment of thrombotic diseases, in particular myocardial infarction.

Typically, therefore, the pharmaceutical compounds of the invention may be administered orally or parenterally ("parenterally" as used herein, refers to modes of administration which include intravenous, intramuscular, intraperitoneal, intrasternal, subcutaneous and intraarticular injection and infusion of which intavenous is most preferred.) to a host to obtain a desired effect, for example protection against ischaemia or a cardioprotectant effect. In the case of larger animals, such as humans, the compounds may be administered alone or as compositions in combination with pharmaceutically acceptable diluents, excipients or carriers.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

Another aspect of this invention is directed to methods of reducing tissue damage (e.g., substantially preventing tissue damage, inducing tissue protection) resulting from ischemia or hypoxia comprising administering to a mammal in need of such treatment a therapeutically effective amount of a product of the invention.

Preferred ischemic/hypoxic tissues taken individually or as a group are cardiac, brain, liver, kidney, lung, gut, skeletal muscle, spleen, pancreas, nerve, spinal cord, retina tissue, the vasculature, or intestinal tissue, an especially preferred ischemic/hypoxic tissue is cardiac tissue.

It is especially preferred that the products of the invention are administered to prevent perioperative myocardial ischemic injury.

Preferably, the products of this invention are administered prophylactically.

The ischemic/hypoxic damage may occur during organ transplantation.

Preferably, the compounds of this invention are administered prior to, during or shortly after, cardiac surgery or non-cardiac surgery (e.g., a three to four day infusion).

In one aspect of this invention a product of the invention is administered locally.

Another aspect of this invention is directed to methods of reducing myocardial tissue damage (e.g., substantially preventing tissue damage, inducing tissue protection) during surgery (e.g., coronary artery bypass grafting (CABG) surgeries, vascular surgeries, percutaneous transluminal coronary angioplasty (PTCA) or any percutaneous transluminal coronary intervention (PTCI), organ transplantation, or other non-cardiac surgeries) comprising administering to a mammal a therapeutically effective amount of a product of the invention. Another aspect of this invention is directed to methods of reducing myocardial tissue damage (e.g., substantially preventing tissue damage, inducing tissue protection) in patients presenting with ongoing cardiac syndromes (acute coronary syndromes, e.g., myocardial infarction or unstable angina) or cerebral ischemic events (e.g., stroke) comprising administering to a mammal a therapeutically effective amount of a product of the invention.

Another aspect of this invention is directed to chronic methods of reducing myocardial tissue damage (e.g., substantially preventing tissue damage, inducing tissue protection) in a patient with diagnosed coronary heart disease (e.g., previous myocardial infarction or unstable angina) or patients who are at high risk for myocardial infarction (e.g. age >65 and two or more risk factors for coronary heart disease) comprising administering to a mammal a therapeutically effective amount of a product of the invention.

Another aspect of this invention is directed to methods of preventing ischemic/hypoxic damage comprising the chronic oral administration to a mammal in need of such treatment of a therapeutically effective amount of a product of the invention.

Another aspect of this invention is directed to methods for treating cardiovascular diseases comprising administering to a mammal a therapeutically effective amount of a product of the invention.

Another aspect of this invention is directed to methods for treating arteriosclerosis comprising administering to a mammal a therapeutically effective amount of a product of the invention.

Another aspect of this invention is directed to methods for treating arrhythmia comprising administering to a mammal a therapeutically effective amount of a product of the invention.

Another aspect of this invention is directed to methods for treating angina pectoris comprising administering to a mammal a therapeutically effective amount of a product of the invention.

Another aspect of this invention is directed to methods for treating cardiac hypertrophy comprising administering to a mammal a therapeutically effective amount of a product of the invention.

Another aspect of this invention is directed to methods for treating renal diseases comprising administering to a mammal a therapeutically effective amount of a product of the invention.

Another aspect of this invention is directed to methods for treating diabetic complications comprising administering to a mammal a therapeutically effective amount of a product of the invention.

Another aspect of this invention is directed to methods for treating restenosis comprising administering to a mammal a therapeutically effective amount of a product of the invention.

Another aspect of this invention is directed to methods for treating organ hypertrophies or hyperplasias comprising administering to a mammal a therapeutically effective amount of a product of the invention.

Another aspect of this invention is directed to methods for treating septic shock and other inflammatory diseases (septicemia, endotoxcemia) comprising administering to a mammal a therapeutically effective amount of a product of the invention.

Another aspect of this invention is directed to methods for treating cerebro ischemic disorders comprising administering to a mammal a therapeutically effective amount of a product of the invention.

Another aspect of this invention is directed to methods for treating myocardial stunning comprising administering to a mammal a therapeutically effective amount of a product of the invention.

Another aspect of this invention is directed to methods for treating myocardial dysfunction comprising administering to a mammal a therapeutically effective amount of a product of the invention.

Another aspect of this invention is directed to methods for treating cerebrovascular diseases comprising administering to a mammal a therapeutically effective amount of a product of the invention.

Further applications of the products of the invention are described in the prior art documents mentioned under the heading "Background of the Invention".

Pharmaceutical Compositions

The present invention also provides a pharmaceutical composition comprising a pharmaceutically acceptable carrier and an effective amount, e.g., a therapeutically effective amount, including a prophylactically effective amount, of one or more of the aforesaid compounds. The products of the invention may be formulated into pharmaceutical compositions as described in WO 95/02604, the contents of which are incorporated herein by reference.

According to a further aspect of the invention there is thus provided a pharmaceutical composition including a compound of the invention, in admixture with a pharmaceutically acceptable adjuvant, diluent or carrier. Proposed compositions are intavenous formulations. These formulations typically contain a compound of the invention or a salt thereof.

Pharmaceutical compositions of this invention for parenteral injection suitably comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms may be ensured by the inclusion of various antibacterial and antifungal agents, for example, paraben, chlorobutanol or phenol sorbic acid. It may also be desirable to include isotonic agents such as sugars or sodium chloride, for example. Prolonged absorption of the injectable pharmaceutical form may be brought about by the inclusion of agents (for example aluminum monostearate and gelatin) which delay absorption.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are suitably made by forming microencapsule matrices of the drug in biodegradable polymers, for example polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use.

Solid dosage forms for oral administration include capsules, tablets, pills, powders and granules. In such solid dosage forms, the active compound is typically mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Suitably, oral formulations contain a dissolution aid. The dissolution aid is not limited as to its identity so long as it is pharmaceutically acceptable. Examples include nonionic surface active agents, such as sucrose fatty acid esters, glycerol fatty acid esters, sorbitan fatty acid esters (e.g., sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g., chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, and/or in delayed fashion. Examples of embedding compositions which can be used include polymeric substances and waxes.

The products of the invention may also be in micro-encapsulated form, if appropriate, with one or more of the above-mentioned excipients.

The active compound may be in finely divided form, for example it may be micronised.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and the phosphatidyl cholines (lecithins), both natural and synthetic. Methods to form liposomes are known in the art, for example, Prescott, Ed., Methods in Cell Biology, Volume XIV, Academic Press, New York, N.Y. (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants which may be required. Ophthalmic formulations, eye ointments, powders and solutions are also contemplated as being within the scope of this invention.

Advantageously, the compounds of the invention are orally active, have rapid onset of activity and low toxicity.

The compounds of the invention have the advantage that they may be more efficacious, be less toxic, be longer acting, have a broader range of activity, be more potent, produce fewer side effects, be more easily absorbed than, or that they may have other useful pharmacological properties over, compounds known in the prior art.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired. The compounds of the invention may be administered by any suitable means. A preferred method of administration is by IV injection. In proper doses and with suitable administration of certain compounds, the present invention provides for a wide range of selective $A_3$ receptor-dependent responses. Exemplary dosages range from about 0.1 to about 100 mg/kg body weight of the animal being treated/day. Therapeutically effective dosages range from about 0.01 to about 10 mg/kg body weight/day. The invention will now be illustrated by the following non-limiting examples.

This invention is also directed to pharmaceutical compositions which comprise a therapeutically effective amount of a product of the invention and a pharmaceutically acceptable carrier, vehicle or diluent.

This invention is also directed to pharmaceutical compositions for the reduction of tissue damage resulting from ischemia or hypoxia which comprise a therapeutically effective amount of a product of the invention.

This invention is also directed to a kit for use in treating a mammal having or at risk of having a disease or condition resulting from, for example, ischemia or hypoxia which may be ameliorated by an A3 agonist. The kit comprises a) a suitable dosage form, such as, for example, an injectable parenteral solution particularly adapted for intravenous or intramuscular injection, comprising a compound of Formula I; and b) instructions describing a method of using the dosage form to reduce tissue damage resulting from ischemia or hypoxia.

Yet another aspect of this invention is combinations of a product of the invention and one or more other compounds as described below.

This invention is also directed to a pharmaceutical combination composition comprising: a therapeutically effective amount of a composition comprising a first product, said first product being a product of the invention;

a second compound, said second compound being a cardiovascular agent; and, optionally, a pharmaceutical carrier, vehicle or diluent.

Another aspect of this invention are methods of reducing tissue damage (e.g., substantially preventing tissue damage, inducing tissue protection) resulting from or which could result from ischemia or hypoxia comprising administering to a mammal a first product, said first compound being a product of the invention; and a second product, said second product being a cardiovascular agent wherein the amounts of the first and second compounds result in a therapeutic effect.

Another aspect of this invention are kits comprising:

a. a product of the invention and a pharmaceutically-acceptable carrier, vehicle or diluent in a first unit dosage form;

b. a cardiovascular agent and a pharmaceutically acceptable carrier, vehicle or diluent in a second unit dosage form; and c. means for containing said first and second dosage forms wherein the amounts of the first and second compounds result in a therapeutic effect.

The invention therefore includes methods of treatment in which a product of the invention and one or more other therapeutic agents are administered to a mammal. Also included are products including both a product of the invention and one or more other therapeutic agents. Said other therapuetic agent(s) (e.g., agents having a cardiovascular effect) are, for example, β-blockers (e.g., acebutolol, atenolol, bopindolol, labetolol, mepindolol, nadolol, oxprenol, pindolol, propranolol, sotalol), calcium channel blockers (e.g., amlodipine, nifedipine, nisoldipine, nitrendipine, verapamil), potassium channel openers, adenosine, adenosine agonists, sodium-hydrogen exchanger type 1 (NHE-1) inhibitors, ACE inhibitors (e.g., captopril, enalapril), nitrates (e.g., isosorbide dinitrate, isosorbide 5-mononitrate, glyceryl trinitrate), diuretics (e.g., hydrochlorothiazide, indapamide, piretanide, xipamide), glycosides (e.g., digoxin, metildigoxin), thrombolytics as described above, platelet inhibitors (e.g., repro), aspirin, dipyridamol, potassium chloride, clonidine, prazosin, pyruvate dehydrogenase kinase inhibitors (e.g., dichloroacetate), pyruvate dehydrogenase complex activators, biguanides (e.g. metformin) or other 5 adenosine A3 receptor agonists. Other cardiovascular agents include angiotensin II (AII) receptor antagonists, C5a inhibitors, soluble complement receptor type 1 (sCR1) or analogues, partial fatty acid oxidation (PFOX) inhibitors (specifically, ranolazine), acetyl CoA carboxylase activators, malonyl CoA decarboxylase inhibitors, 5' AMP-activated protein kinase (AMPK) inhibitors, adenosine nucleoside inhibitors, antiapoptotic agents (e.g., caspase inhibitors), monophosphoryl lipid A or analogues, nitric oxide synthase activators/inhibitors, protein kinase C activators (specifically, protein kinase E), protein kinase delta inhibitor, poly (ADP ribose) synthetase (PARS, PARR) inhibitors, metformin (gluconeogenesis inhibitors, insulin sensitizers), endothelin converting enzyme (ECE) inhibitors, endothelin ETA receptor antagonists, thrombin activated fibrinolytic inhibitor TAFI inhibitors and Na/Ca exchanger modulators.

In one very preferred method, a patient is administered, in effective amounts, a product of the invention and a thrombolytic. Sometimes, but not always, one of these two active agents is administered more or less immediately after the other.

This invention is also directed to a pharmaceutical combination composition comprising: a therapeutically effective amount of a composition comprising a first product, said first product being a product of the invention;

a second product, said second product being a glycogen phosphorylase inhibitor; and, optionally, a pharmaceutical carrier, vehicle or diluent.

Another aspect of this invention resides in methods of reducing tissue damage (e.g., substantially preventing tissue damage, inducing tissue protection) resulting from or which could result from ischemia or hypoxia comprising administering to a mammal a. first compound, said first compound being a product of the invention said second compound being a glycogen phosphorylase inhibitor wherein the amounts of the first and second compounds result in a therapeutic effect.

Another aspect of this invention are kits comprising:

a. a product of the invention and a pharmaceutically acceptable carrier, vehicle or diluent in a first unit dosage form;

b. a glycogen phosphorylase inhibitor and a pharmaceutically acceptable carrier, vehicle or diluent in a second unit dosage form; and a. means for containing said first and second dosage forms wherein the amounts of the first and second compounds result in a therapeutic effect.

This invention is also directed to a pharmaceutical combination composition comprising: a therapeutically effective amount of a composition comprising a product of the invention;

an aldose reductase inhibitor; and, optionally, a pharmaceutical carrier, vehicle or diluent.

Another aspect of this invention are methods of reducing tissue damage (e.g., substantially preventing tissue damage, inducing tissue protection) resulting from or which could result from ischemia or hypoxia comprising administering to a mammal a. a product of the invention and b. an aldose reductase inhibitor wherein the amounts of said product and said inhibitor result in a therapeutic effect.

Another aspect of this invention are kits comprising:

a. a product of the invention and a pharmaceutically acceptable carrier, vehicle or diluent in a first unit dosage form;

b. an aldose reductase inhibitor and a pharmaceutically acceptable carrier, vehicle or diluent in a second unit dosage form; and c. means for containing said first and second dosage forms wherein the amounts of the first and second compounds result in a therapeutic effect.

In the above combination compositions, combination methods and kits a preferred aldose reductase inhibitor is zopolrestat:, 3,4-dihydro-4-oxo-3-[[5-trifluoromethyl)-2-benzothiazolyl]methyl]-1-phthalazineacetic acid.

In the methods of treatment as applied to the combinations described above the following are preferred administration routes, modes, etc.

Preferred ischemic or hypoxic tissues taken individually or as a group are wherein the ischemic/hypoxic tissue is cardiac, brain, liver, kidney, lung, gut, skeletal muscle, spleen, pancreas, nerve, spinal cord, retina tissue, the vasculature, or intestinal tissue.

An especially preferred ischemic or hypoxic tissue is cardiac tissue.

It is especially preferred that the combinations are administered to prevent perioperative myocardial ischemic injury.

Preferably, the combinations of this invention are administered prophylactically.

The ischemic/hypoxic damage may occur during organ transplantation.

Preferably, the combinations of this invention are administered prior to, during and/or shortly after, cardiac surgery or non-cardiac surgery.

In one aspect of this invention the combinations are administered locally.

In one aspect of this invention myocardial tissue damage is reduced during or after surgery.

In another aspect of this inventor myocardial tissue damage is reduced in patients presenting with ongoing cardiac or cerebral ischemic events.

In yet another aspect of this inventor myocardial tissue damage is reduced by chronic administration of the above combinations in a patient with diagnosed coronary heart disease.

The term "reduction" is intended to include partial prevention or prevention which, although greater than that which would result from taking no compound or from taking a placebo, is less than 100% in addition to substantially total prevention.

The term "damage resulting from ischemia or hypoxia" as employed herein refers to conditions directly associated with reduced blood flow or oxygen delivery to tissue, for example due to a clot or obstruction of blood vessels which supply blood to the subject tissue and which result, inter alia, in lowered oxygen transport to such tissue, impaired tissue performance, tissue dysfunction and/or necrosis and/or apoptosis. Alternatively, where blood flow or organ perfusion may be quantitatively adequate, the oxygen carrying capacity of the blood or organ perfusion medium may be reduced, e.g., in a hypoxic environment, such that oxygen supply to the tissue is lowered, and impaired tissue performance, tissue dysfunction, and/or tissue necrosis and/or apoptosis ensues.

The term "treating", "treat" or "treatment" as used herein includes preventative (e.g., prophylactic) and palliative treatment.

Compound Synthesis

Compounds of the invention may be synthesized by any suitable means. In this respect, synthesis of adenosine analogues is well known in the art and is described in the documents listed above under the heading "Background of the Invention". For example, guidance may be found in the "Compound Synthesis" sections of WO 95/02604 as well as of corresponding U.S. Pat. No. 5,773,423 and U.S. Pat. No. 5,688,774, which sections are included herein by reference. The reader is also referred to reaction schemes A to I and examples of WO 92/05177 and corresponding U.S. Pat. No. 5,561,134 and U.S. Pat. No. 5,736,554, all of which disclosures are incorporated herein by reference. Further assistance may be found in EP 1241176 and corresponding U.S. Ser. No. 60/276,411, including Schemes I, II and III thereof and the related text, all of which disclosures are incorporated herein by reference. The following methods and reactants (intermediates) are novel and part of the invention.

A first method comprises reacting a compound of the formula L-CR$^{20}$R$^{21}$—CYCLE, where L is a leaving group, with a compound H$_2$N-ARA, where the nitrogen of H$_2$N— is the N6 nitrogen of an adenosine A3 receptor agonist and ARA represents the remainder of the adenosine A3 receptor agonist.

A second method comprises reacting a compound of the formula H$_2$N—CR$^{20}$R$^{21}$-CYCLE with a compound of the formula C6-L-ARA, where ARA again represents the residue of an adenosine A3 receptor agonist, excluding the N6 nitrogen, and C6-L represents a leaving group substituted on the C6 carbon of ARA. Especially but not exclusively in this second method, reactive functional groups of ARA (e.g. hydroxy or amino groups constituting X$^3$ and X$^4$ of formula III) may be protected.

Suitable leaving groups include chloro and bromo. Chloro is often convenient for the second method, as in the case of an ARA residue as illustrated by formula IV in which R$^2$ is H and R$^1$ is Me.

One suitable method for synthesising amongst others, the compounds of formula I of the invention in which R$^2$ is hydrogen is as follows.

This method uses as a starting material the known 5'-N-alkylcarboxamidoadenosines such as 5'-N-methylcarboxamidoadenosine, which may be protected as necessary prior to reaction. The 2-picolyl reactant may be made using the reaction scheme of FIG. 1, which may be generalised where necessary.

Figure 2:
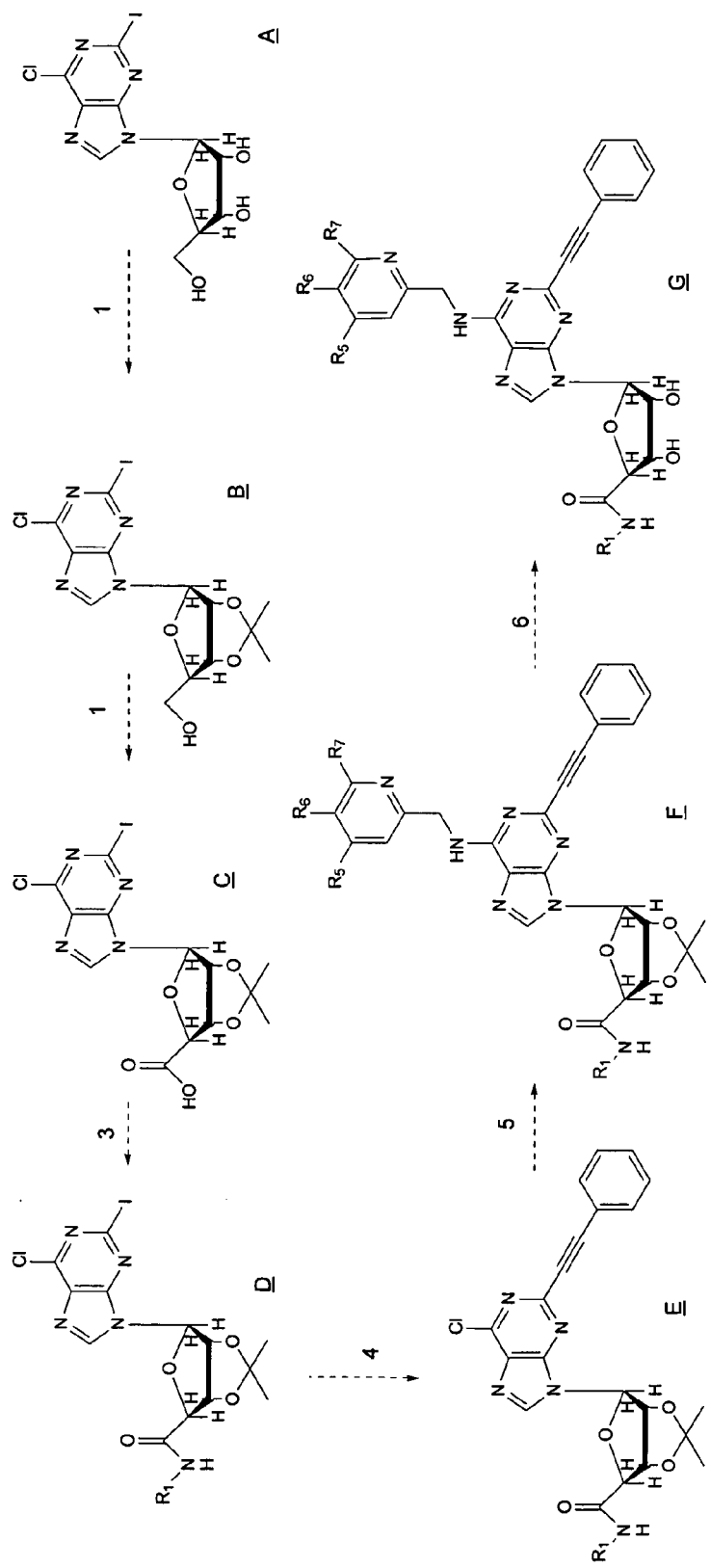
FIG. 2 is a reaction scheme for the synthesis of the 2-alkenyl substituted compounds of the invention.

The 2-alkynyl substituted compounds of the invention may be synthesised using the synthetic reaction scheme illustrated in FIG. 2, which may be generalized where necessary. In this scheme, the 6-chloro-2-iodopurine-9-riboside (Compound A) is already known, J. Med. Chem., 2000, vol43, page 4137. In step 1, this is protected in a manner known per se to yield compound B which is then oxidised to give acid C. Acid C is reacted with the R$^1$ amine (R$^1$NH$_2$) to give uronamide D. The 2 iodo uronamide is then reacted with triethylamine, bis(triphenylphosphine)palladium dichloride and CuI in catalytic amount using as solvent a mixture of acetonitrile/DMF 2:1 and to this mixture is added the terminal alkyne and the reaction takes place under N$_2$ atmosphere at room temperature (ref J. Med. Chem. 1995, vol 38, 1462-1472) to result in compound E. The coupling of the 2-picolylamine with the 6-chloro derivative is then accomplished as described above (compound F), and deprotection with HCl 1N at 70° C. yields the final compound, G. In the example shown, the alkyne used in the phenyl alkyne; other alkynes can be used in analogous manner. The alkynyl compounds may be prepared analogously.

Another method, suited for example for synthesising the compounds of formula II of the invention in which R$^2$ is hydrogen is as follows:

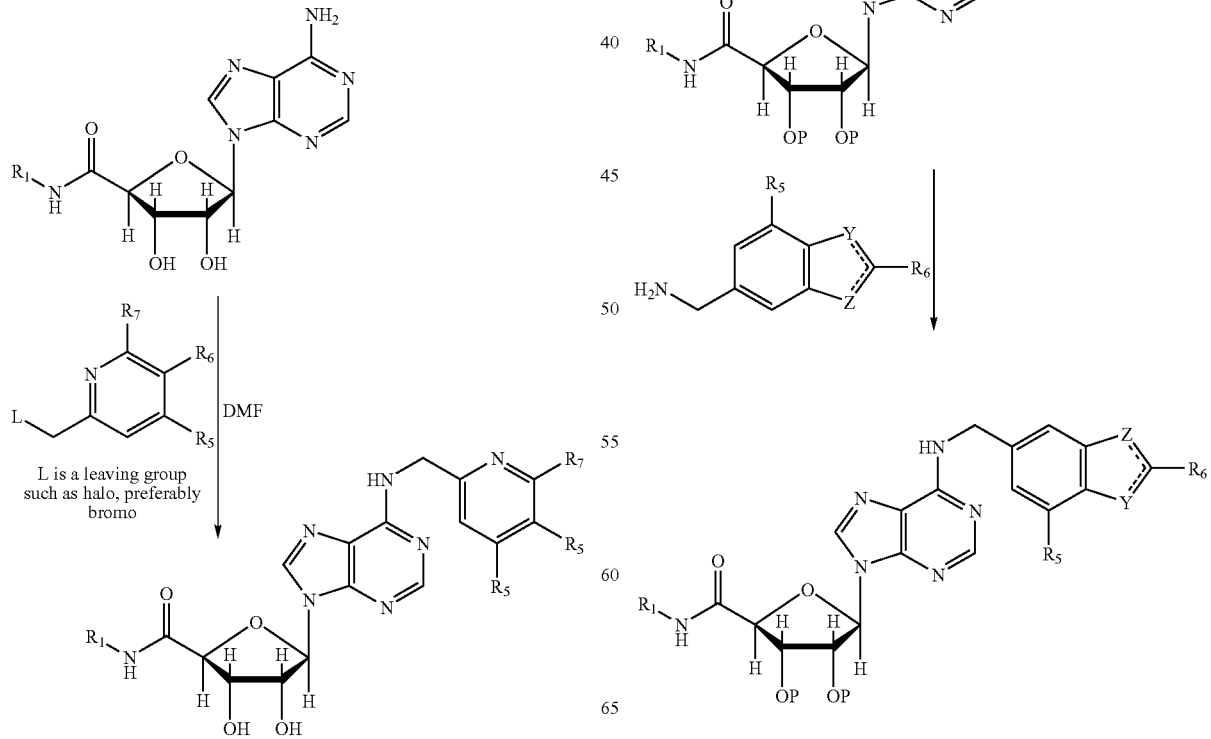

Each P is a protecting group, which may be taken together to represent a bridging protecting group such as an isopropylidene radical. The protecting group may be removed by conventional means, for example by treatment with an acid.

L is a leaving group which may for example be selected from chloro, bromo or iodo or tosylates. Preferably the leaving group is chloro.

Figure 3:
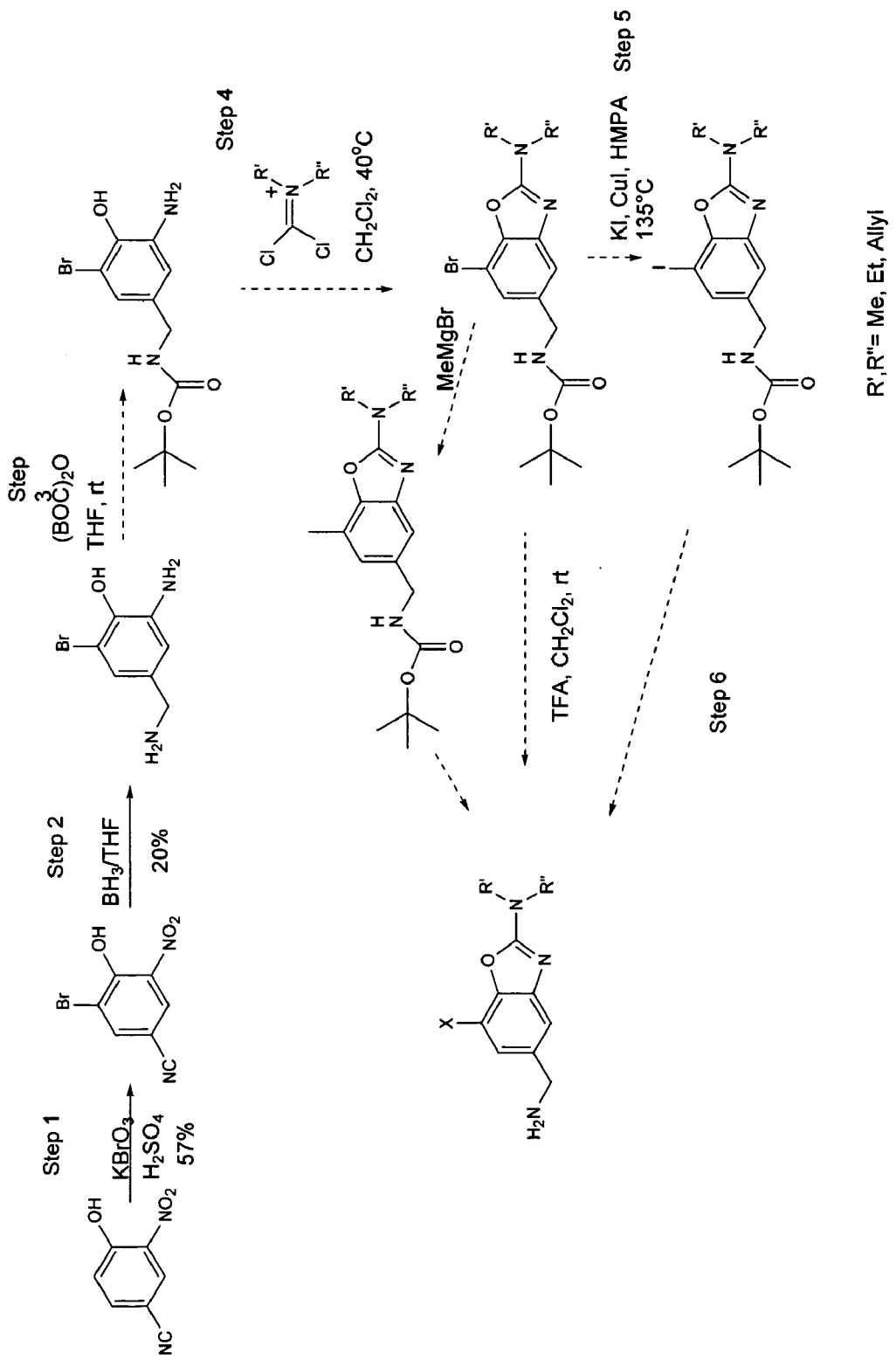
FIG. 3 is a reaction scheme for synthesis of the benzoxazole reactant.
Figure 4:
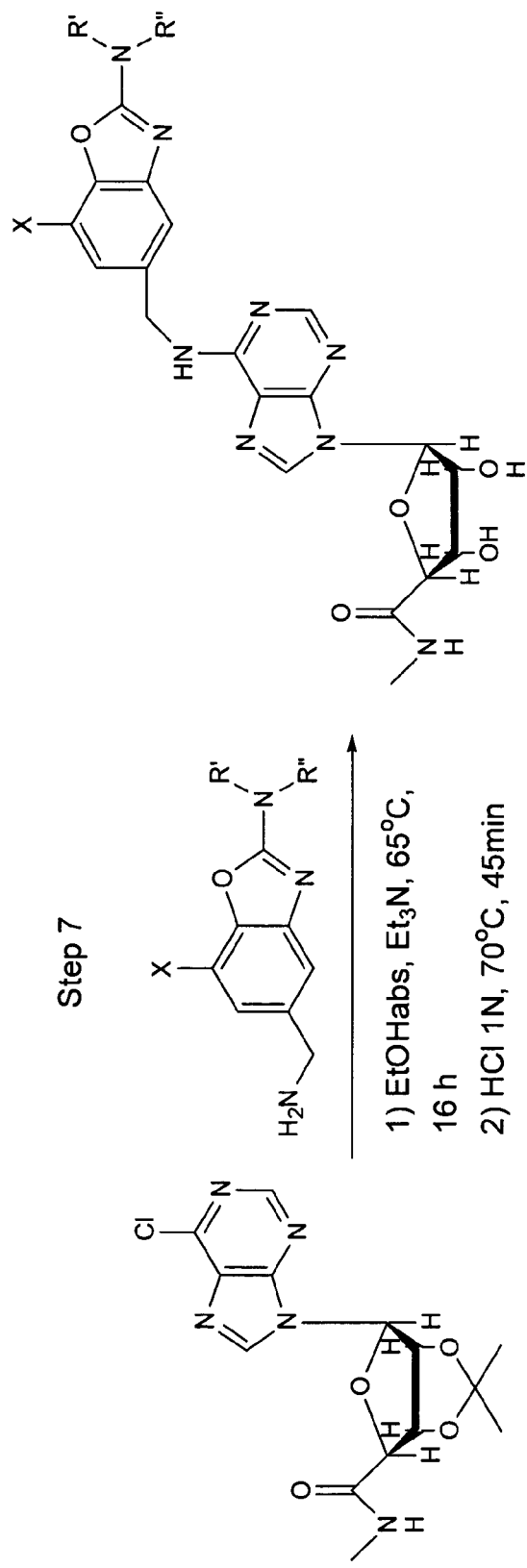
FIG. 4 is a reaction scheme for the synthesis of compounds in accordance with the second embodiment of the invention.

This method thus uses as a starting material the known 2',3'-O-isopropylidene-6-chloropurine-5'-alkyluronamide and equivalents. This reaction step is also shown more specifically in the reaction scheme of FIG. 4. The benzoxazole reactant may be made using the reaction scheme of FIG. 3, which may be generalised where necessary.

Figure 5:
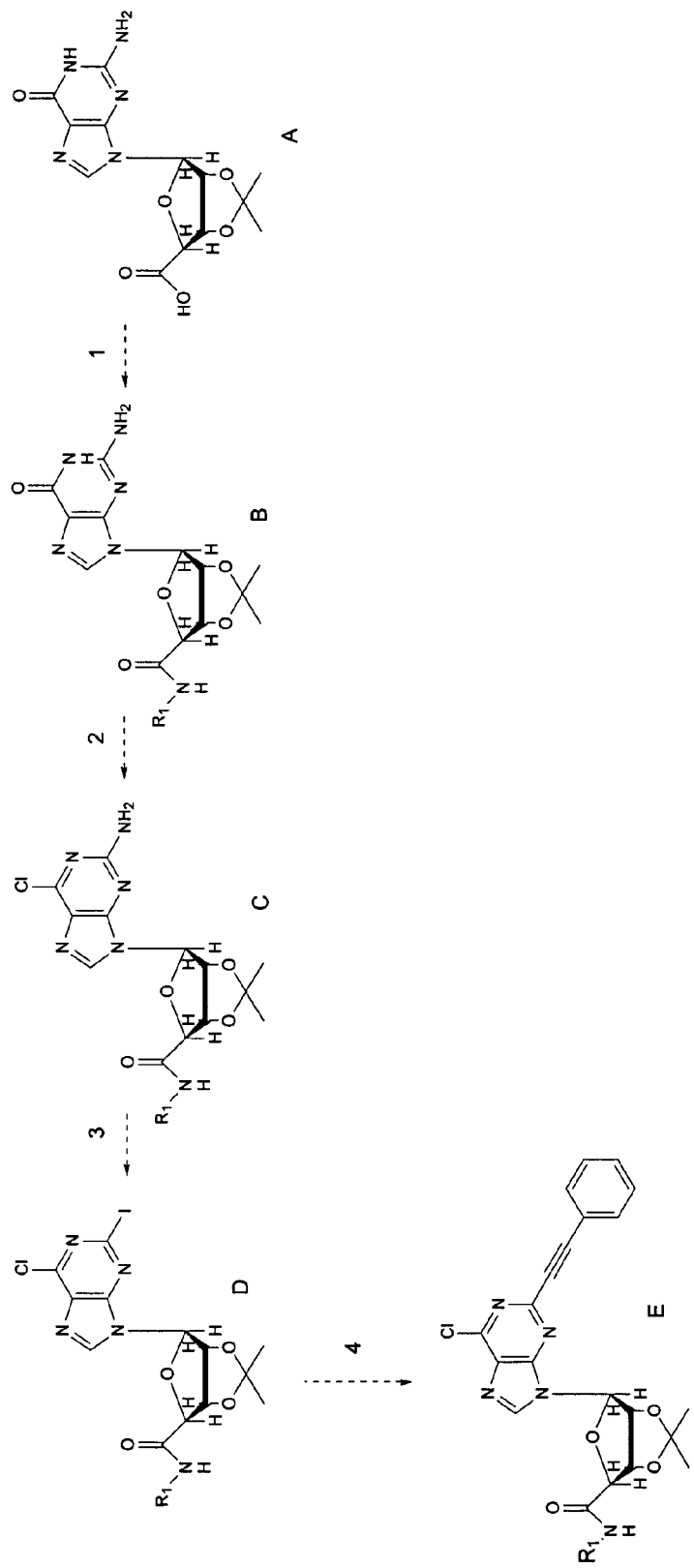
FIG. 5 is a reaction scheme for synthesis of 2-alkynyl substituted compounds of the invention.

The 2-alkynyl substituted compounds of the invention may be synthesised using the synthetic reaction scheme illustrated in FIG. 5 which may be generalized where necessary. 2',3'-O-Isopropylideneguanosine-5'-carboxylic acid A (*J. Org. Chem.* 1999, 64, 293-295) is reacted with triethylamine, isopropenylchloroformate and methylamine at 0° C. yielding compound B. This is reacted with phosphoryl chloride to obtain compound C. C is treated with isoamyl nitrite, CuI, $CH_2I_2$ and $I_2$ to give compound D. The 2 iodo uronamide is then reacted with triethylamine, bis(triphenylphosphine)palladium dichloride and CuI in catalytic amount using as solvent a mixture of acetonitrile/DMF 2:1 and to this mixture is added the terminal alkyne and the reaction takes place under $N_2$ atmosphere at room temperature (ref *J. Med. Chem.* 1995, vol 38, 1462-1472) to result in compound E. The coupling of the benzoxazole reactant with the 6-chloro derivative is then accomplished as described above. In the example shown, the alkyne used in the phenyl alkyne; other alkynes can be used in analogous manner. The alkenyl compounds may be prepared analogously.

EXAMPLES

Example 1

$N^6$-(4-methyl-2-picolyl)-adenosine-5'-N-methyluronamide

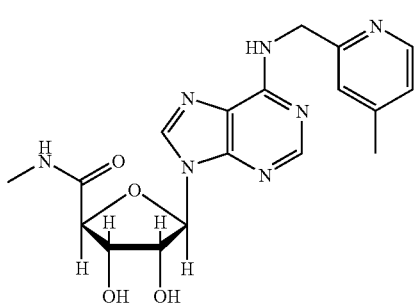

To a solution of 5'-N-methylcarboxamidoadenosine (100 mg, 0.34 mmol) in DMF (1 mL) was added 2-(bromomethyl)-4-methylpyridine (95 mg, 0.51 mmol), and the solution stirred for 3 days at 40° C. The solvent was evaporated and the residue treated with methanol (1.5 mL) and concentrated $NH_4OH$ (3.0 mL). The mixture was warmed in a closed vessel at 90° C. for 2 h with stirring. After evaporating the solvent, the residue was chromatographied (6% MeOH in $CH_2Cl_2$) and 60 mg (44%) of the title compound (a white solid) were obtained. Rf ($CH_2Cl_2$/MeOH 9:1) 0.3; $^1H$ NMR ($CD_3OD$) δ 8.3-8.5 (m, 3H, H-8, H-2, H-$6_{pyridyl}$), 7.31 (s, 1H, H-$3_{pyridyl}$), 7.19 (d, 1H, J=5.0 Hz, H-$5_{pyridyl}$), 6.07 (d, 1H, $J_{1',2'}$=7.8 Hz, H-1'), 4.9 (not observed, 2H, $CH_2$), 4.79 (dd, 1H, $J_{2',1'}$=7.8 Hz, $J_{2',3'}$=4.7 Hz, H-2'), 4.52 (s, 1H, H-4'), 4.35 (d, 1H, $J_{3',2'}$=4.7 Hz, H-3'), 2.91 (s, 3H, 5'-N-methyl), 2.37 (s, 3H, $CH_3$); $^{13}C$ NMR ($CD_3OD$) δ 173.2 (C-5'), 159.6 ($C_{pyridyl}$-2), 156.6 (C-6), 154.3 (C-2), 151.1 (C-4), 149.5 $C_{pyridyl}$-6), ), 143.0 ($C_{pyridyl}$-4), 142.8 (C-8), 125.1 ($C_{pyridyl}$-3), 123.8 ($C_{pyridyl}$-5), 122.2 (C-5), 90.9 (C-1'), 86.9 (C-4'), 75.3, 73.8 (C-3', C-2'), 46.5 ($CH_2$), 26.4 (5'-N-methyl), 21.5 ($CH_3$). High-resolution MS calculated for ($C_{18}H^{21}N_7O_4Na$) 422.1553, found 422.1556.

2-(Bromomethyl)-4-methylpyridine

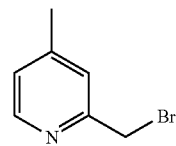

To a mixture of the alcohol 2-(Hydroxymethyl)-4-methylpyridine (560 mg, 4.55 mmol) and $CBR^4$ (2.43 g, 7.33 mmol) in $CH_2Cl_2$ (10.6 mL) was added triphenylphosphine (1.4 g, 5.34 mmol) in several portions at 0° C. The reaction mixture was stirred for 20 min at the same temperature and then directly passed through a short silica gel column using 10% EtOAc in hexane as an eluent to give the title compound as a white solid (640 mg) in 76% yield. $^1H$ NMR ($CDCl_3$) δ 8.34 (d, 1H, J=4.9 Hz, H-6); 7.17 (s, 1H, H-3); 6.94 (d, 1H, J=4.9 Hz, H-5); 4.43 (s, 2H, $CH_2$); 2.26 (s, 3H); $^{13}C$ NMR ($CDCl_3$) δ 156.9 (C-2), 149.8 (C-6), 148.8 (C-4), 124.7 (C-3), 124.4 (C-5), 34.4 ($CH_2$), 21.4 (Me).

2-(Hydroxymethyl)-4-methylpyridine

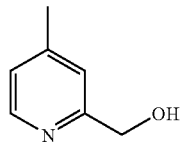

Compound 2,4-Dimethylpyridine N-Oxide (4.47 g, 36.3 mmol) was dissolved in $Ac_2O$ (11 mL) and added dropwise to acetic anhydride (108 mL) heated to 110° C. The resulting solution was stirred at 110° C. for 1 hour and 15 minutes. Excess reagent was evaporated leaving the corresponding 2-[(acetyloxy)-methyl]pyridine which was used without further purification. To a solution of the protected alcohol in MeOH (5 mL) was added NaOH 2N (15 mL) at room temperature. The mixture was stirred at room temperature for 1.5 hours, extracted with EtOAc and washed with water. The solvent was evaporated giving a residue that was purified by column chromatography (4% MeOH in $CH_2Cl_2$) affording 1.54 g (34% overall yield) of colorless oil. $^1H$ NMR ($CD_3OD$) δ 8.29 (d, 1H, J=4.2 Hz, H-6); 7.40 (s, 1H, H-3); 7.11 (d, 1H, J=4.2 Hz, H-5); 5.10 (s, 1H, OH); 4.68 (s, 2H, $CH_2$); 2.38 (s, 3H); $^{13}C$ NMR ($CD_3OD$) δ 162.4 C-2), 151.0 (C-4), 149.4 (C-6), 125.0 (C-3), 123.3 (C-5), 65.8 ($CH_2$), 21.7 (Me).

2,4-Dimethylipyridine N-Oxide

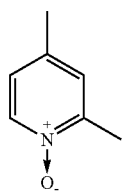

Aqueous $H_2O_2$ (30%, 2.6 mL) was added to 2,4-lutidine (5 mL, 43.2 mmol) in acetic acid (15 mL), and the mixture was stirred for 3 hours at 90° C. The mixture was cooled, and a second portion of aqueous $H_2O_2$ (30%, 1.1 mL) was added, after which the mixture was stirred for another 20 hours at 90° C. The solvent was evaporated (toluene was used to remove remaining traces of acetic acid by means of azeotropic destillation). The pH was adjusted to 10 with NaOH 10 M, $CH_3CN$ was added (10 mL) and precipitated materials were filtered off. The filtrate was evaporated leaving 4.47 g (84%) of the title compound as a white solid. $^1H$ NMR ($CDCl_3$) δ 8.10 (d, 1H, J=6.5 Hz, H-6); 7.04 (s, 1H, H-3); 6.92 (d, 1H, J=6.5 Hz, H-5); 2.45 (s, 3H), 2.28 (s, 3H); $^{13}C$ NMR ($CDCl_3$) δ 148.6 (C-4), 139.1 (C-6), 137.6 (C-2), 127.6 (C-3), 124.8 (C-5), 20.6 ($Me_{C4}$), 18.2 ($Me_{C2}$).

Example 2

$N^6$-(4-iodo-2-picolyl)-adenosine-5'-N-methyluronamide

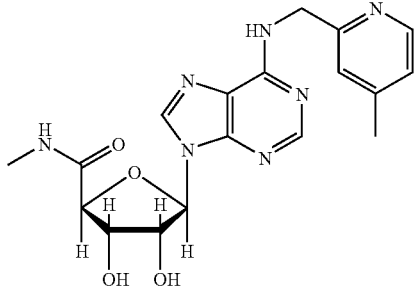

To a solution of 5'-N-methylcarboxamidoadenosine (150 mg, 0.51 mmol) in DMF (1.5 mL) was added 2-(Bromomethyl)-4-iodopyridine (152 mg, 0.51 mmol), and the solution stirred for 3 days at 40° C. The solvent was evaporated and the residue treated with methanol (1.5 mL) and concentrated $NH_4OH$ (3.0 mL). The mixture was warmed in a closed vessel at 90° C. for 2 h with stirring. After evaporating the solvent, the residue was chromatographied (4% MeOH in $CH_2Cl_2$) and 140 mg (54%) of the title compound (a white solid) were obtained. $R_f$($CH_2Cl_2$/MeOH 9:1) 0.37; m.p. (MeOH): 128° C.; $^1H$ NMR ($CD_3OD$) δ 8.40 (s, 1H, H-8), 8.38 (s, 1H, H-2), 8.26 (d, 1H, J=5.2 Hz, $H_{pyridyl}$-6), 7.92 (s, 1H, $H_{pyridyl}$-3), 7.79 (dd, 1H, J=5.2 Hz, J=1.2 Hz, $H_{pyridyl}$-5), 6.13 (d, 1H, $J_{1',2'}$=7.7 Hz, H-1'), 4.97 (s, 2H, $CH_2$), 4.86 (dd, 1H, $J_{2',1'}$=7.7 Hz, $J_{2',3'}$=4.7 Hz, H-2'), 4.59 (s, 1H, H-4'), 4.43 (dd, 1H, $J_{3',2'}$=4.7 Hz, $J_{3',4'}$=1.2 Hz, H-3'), 2.97 (s, 3H, 5'-N-methyl); $^{13}C$ NMR (DMSO-$d_6$) δ 170.2 (C-5'), 160.5 ($C_{pyridyl}$-2), 155.9 (C-6), 152.9 (C-2), 150.0 ($C_{pyridyl}$-6), 148.2 (C-4), 141.3 (C-8), 131.3 ($C_{pyridyl}$-3), 129.9 ($C_{pyridyl}$-5), 120.0 (C-5), 107.3 ($C_{pyridyl}$-4), 88.1 (C-1'), 85.0 (C-4'), 73.4, 72.5 (C-3', C-2'), 48.9 ($CH_2$), 25.7 (5'-N-methyl).

2-(Bromomethyl)-4-iodopyridine

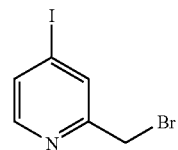

To a mixture of the alcohol (4-Iodo-2-pyridyl)methanol (245 mg, 1.04 mmol) and $CBR^4$ (556 mg, 1.68 mmol) in $CH_2Cl_2$ (4.6 mL) was added triphenylphosphine (320 mg, 1.22 mmol) in several portions at 0° C. The reaction mixture was stirred for 20 min at the same temperature and then directly passed through a short silica gel column using 10% EtOAc in hexane as an eluent to give the title compound as white crystals (220 mg) in 71% yield. M.p.($CH_2Cl_2$) 74-76° C.; $^1H$ NMR ($CDCl_3$) δ 8.29 (d, 1H, J=5.2 Hz, H-6); 7.89 (d, 1H, J=1.5 Hz, H-3); 7.66 (dd, 1H, $J_1$=5.2, $J_2$=1.5 Hz, H-5); 4.52 (s, 2H, $CH_2$); $^{13}C$ NMR ($CDCl_3$) δ 158.1 (C-2), 150.3 (C-6), 133.1 (C-3), 132.7 (C-5), 106.5 (C-4), 33.0 ($CH_2$).

(4-Iodo-2-pyridyl)methanol

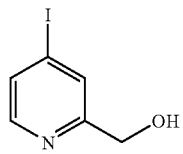

A solution of (4-iodo-2-pyridyl)methylacetate ((4-iodo-2-pyridyl)methylacetate) in 2.0 mL (MeOH/NaOH 2N 1:3) was stirred at room temperature for 40 minutes. The mixture was extracted with EtOAc, washed with NaCl sat., dried and evaporated, affording 245 mg of the title compound (100%) as a colourless oil. $^1H$ NMR ($CDCl_3$) δ 8.18 (d, 1H, J=4.1 Hz, H-6); 7.76 (s, 1H, H-3); 7.59 (d, 1H, J=4.9 Hz, H-5); 4.72 (s, 2H, $CH_2$); 4.45 (bs, 1H, OH); $^{13}C$ NMR ($CDCl_3$) δ 161.2 (C-2), 149.3 (C-6), 132.1 (C-3), 130.5 (C-5), 106.9 (C-4), 64.3 ($CH_2$)

4-Iodo-2-methylpyridine and (4-iodo-2-pyridyl)methylacetate

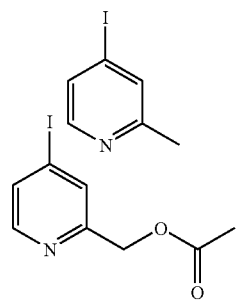

2-(((Tert-butyldimethylsilyl)oxy)methyl)-4-chloropyridine (600 mg, 2.33 mmol), dry sodium iodide (5 g) and freshly distilled acetyl chloride (0.7 mL, 9.78 mmol) in 6 mL of anhydrous acetonitrile were refluxed under nitrogen for 33 hours. Aqueous 10% $K_2CO_3$/5% $NaHSO_3$ was added and the mixture extracted three times with chloroform. After drying ($Na_2SO_4$) and evaporation of the chloroform, flash chromatography (hexane/EtOAc 9:1) yielded 110 mg (22%) of 4-Iodo-2-methylpyridine as a white solid and 290 mg (45%) of (4-iodo-2-pyridyl)methylacetate as a white solid.

4-Iodo-2-methylpyridine: $^1H$ NMR ($CDCl_3$) δ 8.06 (d, 1H, J=5.2 Hz, H-6); 7.48 (d, 1H, J=1.1 Hz, H-3); 7.38 (dd, 1H, $J_1$=5.2, $J_2$=1.4 Hz, H-5); 2.41 (s, 3H, $CH_3$); $^{13}C$ NMR ($CDCl_3$) δ 159.8 (C-2), 149.8 (C-6), 133.0 (C-3), 130.4 (C-5), 106.3 (C-4), 24.5 ($CH_3$).

(4-iodo-2-pyridyl)methylacetate: $^1H$ NMR ($CDCl_3$) δ 8.16 (d, 1H, J=5.2 Hz, H-6); 7.66 (d, 1H, J=1.0 Hz, H-3); 7.54 (dd, 1H, $J_1$=5.2, $J_2$=1.6 Hz, H-5); 5.09 (s, 2H, $CH_2$); 2.11 (s, 3H, $CH_3$); $^{13}C$ NMR ($CDCl_3$) δ 170.9 (CO), 157.1 (C-2), 150.1 (C-6) 132.5 (C-3), 131.3 (C-5), 106.6 (C-4), 66.3 ($CH_2$), 21.3 ($CH_3$).

2-(((Tert-butyldimethylsilyl)oxy)methyl)-4-chloropyridine

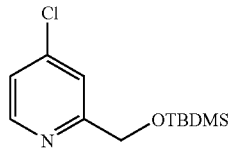

To a mixture of 4-chloro-2-(hydroxymethyl)pyridine (360 mg, 2.51 mmol) and imidazole (684 mg, 10.04 mmol) in DMF (2 mL) was added $^tBuMe_2SiCl$ (452 mg, 3.0 mmol) in several portions at room temperature. The mixture was stirred for 15 min and extracted with ether (50 mL). The extract was washed with water (5 mL×3), dried over $MgSO_4$, and concentrated under reduced pressure. The residue was purified by column chromatography on silica gel eluted with $CH_2Cl_2$ to give the title compound (600 mg, 93%) as a colourless oil. $^1H$ NMR ($CDCl_3$) δ 8.30 (d, 1H, J=5.3 Hz, H-6); 7.44 (d, 1H, J=1.1 Hz, H-3); 7.07 (dd, 1H, $J_1$=5.3, $J_2$=2.0 Hz, H-5); 4.73 (s, 2H, $CH_2$); 0.88 (s, 9H); 0.05 (s, 6H); $^{13}C$ NMR ($CDCl_3$) δ 163.7 (C-2), 150.0 (C-6), 145.3 (C-4), 122.6 (C-3), 120.8 (C-5), 65.9 ($CH_2$), 26.3 (($\underline{CH_3}$)$_3$C), 18.7 (($CH_3$)$_3\underline{C}$), -4.6 (($Me$)$_2Si$).

4-Chloro-2-(hydroxymethyl)pyridine

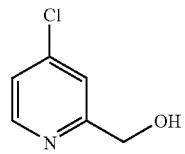

A solution of 4-chloropyridine N-oxide (5 g, 38.6 mmol) and trimethyloxonium tetrafluoroborate (5.94 g, 40.1 mmol) in $CH_2Cl_2$ (115 mL) was stirred for two hours at ambient temperature. The solvent was evaporated and the residue taken up in MeOH (115 mL) and heated to near boiling. Ammonium persulfate (1.76 g, 7.72 mmol) dissolved in $H_2O$ (7.7 mL) was added and the mixture was heated to reflux for 30 min. A second portion of ammonium persulfate (0.88 g) in $H_2O$ (3.9 mL) was added and the mixture was refluxed for another 30 min. The solvent was evaporated and the residue was partitioned between $CH_2Cl_2$ and aqueous $Na_2CO_3$ (10% w/v). The organic layer was washed with $H_2O$, dried over $MgSO_4$, and evaporated leaving 2.4 g (43%) of the title compound. $^1H$ NMR ($CDCl_3$) δ 8.20 (d, 1H, J=5.0 Hz, H-6); 7.31 (s, 1H, H-3); 7.04 (d, 1H, J=5.0 Hz, H-5); 5.46 (s, 1H, OH); 4.61 (s, 2H, $CH_2$).

Example 3

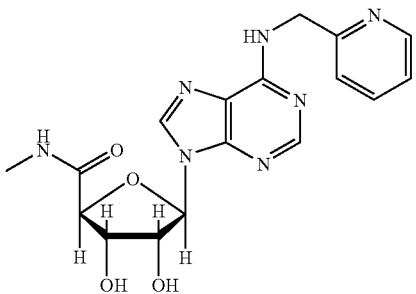

$N^6$-(2-picolyl)adenosine-5'-N-methyluronamide

Procedure A

To a solution of 5'-N-methylcarboxamidoadenosine (64 mg, 0.22 mmol) in DMF (1 mL) was added 2-picolyl chloride hydrochloride (129 mg, 0.79 mmol) and triethylamine (0.11 mL, 0.79 mmol). The solution was stirred for 3 days at 40° C. DMF was removed under vacuum giving a syrup that crystallized when acetone and ether were added. The solvent was removed using a Pasteur pipette. The residue was treated with methanol (1.5 mL), and concentrated $NH_4OH$ (3.0 mL) was added. The mixture was warmed in a closed tube at 90° C. for 2 h with stirring. The solvent was evaporated and the residue purified by column chromatography ($CH_2Cl_2$/MeOH 9:1) yielding 17 mg (20% yield overall) of the title compound as a white foaming solid and 40 mg of starting material.

Procedure B

2',3'-O-Isopropylidene-6-chloropurine-5'-methyluronamide (150 mg, 0.43 mmol), 2-(aminomethyl) pyridine (44 μL, 0.43 mmol), and triethylamine (0.18 mL, 1.26 mmol) were dissolved in absolute ethanol (1.5 mL). The solution was stirred at 65° C. for 16 h in a sealed vessel. The solvent was removed under nitrogen. HCl (1 N) (1.0 mL) was added and the solution stirred at 70° C. for 45 min. After cooling, $NaHCO_3$ was added until pH 7, and a white solid precipitated. The solid was filtered and washed with cold water yielding 94 mg (57% yield overall) of the title compound. Rf ($CH_2Cl_2$MeOH 9:1) 0.3; m.p. 84-86° C.; $^1H$ NMR ($CD_3OD$) δ 8.54 (m, 1H, $H_{pyridyl}$-6), 8.35 (s, 1H, H-8), 8.31 (s, 1H, H-2), 7.81 (dt, 1H, J=7.8 Hz, J=1.8 Hz, $H_{pyridyl}$-4), 7.47 (d, 1H, J=7.8 Hz, $H_{pyridyl}$-3), 7.34 (dd, 1H, J=6.6 Hz, J=5.1 Hz, $H_{pyridyl}$-5), 6.05 (d, 1H, $J_{1',2'}$=7.8 Hz, H-1'), 4.93 (not observed, 2H, $CH_2$), 4.78 (dd, 1H, $J_{1',2'}$=7.8 Hz, $J_{2',3'}$=4.8 Hz, H-2'), 4.52 (d, 1H, $J_{3',4'}$=1.0 Hz, H-4'), 4.35 (dd, 1H, $J_{3',2'}$=4.8 Hz, $J_{3',4'}$=1.0 Hz, H-3'), 2.90 (s, 3H, 5'-N-methyl). $^{13}C$ NMR ($CD_3$ OD) δ 173.2 (C-5'), 160.0 ($C_{pyridyl}$-2), 156.7 (C-6), 154.3 (C-2), 150.2 ($C_{pyridyl}$-6), 142.8 (C-8), 139.2 ($C_{pyridyl}$-

4), 124.2 ($C_{pyridyl}$-3), 123.2 ($C_{pyridyl}$-5), 122.2 (C-5), 90.9 (C-1'), 86.9 (C-4'), 75.3, 73.8 (C-3', C-2'), 46.7 ($CH_2$), 26.4 (5'-N-methyl). High-resolution MS calcd for ($C_{17}H_{19}N_7O_4Na$) 408.1396, found 408.1392. Anal. ($C_{17}H_{19}N_7O_4$) C, H, N.

Example 4

$N^6$-(6-acetyl-2-picolyl)adenosine-5'-N-methyluronamide

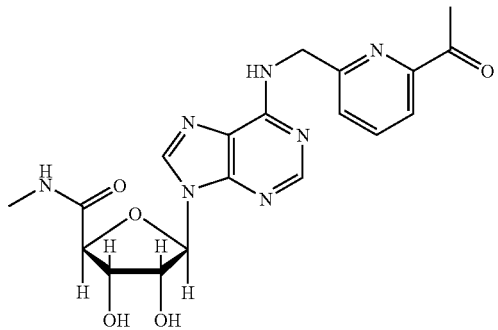

To a solution of 5'-N-methylcarboxamidoadenosine (75 mg, 0.26 mmol) in DMF (1.0 mL) was added 2-(acetyl)-6-bromomethylpyridine (83.5 mg, 0.39 mmol), and the solution stirred for 3 days at 40° C. The solvent was evaporated and the residue treated with methanol (1.0 mL) and concentrated $NH_4OH$ (2.0 mL). The mixture was warmed in a closed vessel at 90° C. for 3 h with stirring. After evaporating the solvent, the residue was chromatographied (4% MeOH in $CH_2Cl_2$) and 63 mg (57%) of the title compound (a white solid) were obtained. Rf ($CH_2Cl_2$/MeOH 9:1) 0.6; m.p.(MeOH): 226-228° C.; $^1$H NMR ($CD_3OD$) δ 8.35 (s, 1H, H-8), 8.32 (s, 1H, H-2), 7.91 (m, 2H, $H_{pyridyl}$-3,5), 7.63 (dd, 1H, J=5.5 Hz, J=3.3 Hz, $H_{pyridyl}$-4), 6.05 (d, 1H, $J_{1',2'}$=7.8 Hz, H-1'), 4.9 (not observed, 2H, $CH_2$), 4.77 (dd, 1H, $J_{2',1'}$=7.8 Hz, $J_{2',3'}$=4.8 Hz, H-2'), 4.50 (s, 1H, H-4'), 4.33 (dd, 1H, $J_{3',2'}$=4.8 Hz, $J_{3',4'}$=1.4 Hz, H-3'), 2.89 (s, 3H, 5'-N-methyl), 2.67 (s, 3H, $CH_3CO$); $^{13}$C NMR (DMSO-$d_6$) δ 199.8 ($\underline{CH_3C}O$), 170.2 (C-5'), 159.3 ($C_{pyridyl}$-2), 155.0 (C-6),152.9 ($C_{pyridyl}$-6), 152.7 (C-2), 148.7 (C-4), 141.3 (C-8), 138.4 ($C_{pyridyl}$-4), 124.8 ($C_{pyridyl}$-3), 120.5 (C-5), 119.7 ($C_{pyridyl}$-5), 88.1 (C-1'), 85.0 (C-4'), 73.4, 72.5 (C-3', C2'),45.4 ($CH_2$), 25.9, 25.7 (5'-N-methyl, $CH_3CO$). High-resolution MS calcd for ($C_{19}H^{21}N_7O_5$ Na) 450.1502, found 450.1503.

2-Acetyl-6-bromomethylpyridine

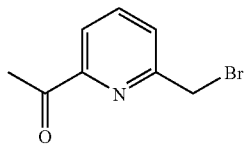

To a mixture of the alcohol 2-Acetyl-6-(hydroxymethyl)pyridine (450 mg, 2.98 mmol) and $CBR^4$ (1.59 g, 4.8 mmol) in $CH_2Cl_2$ (8.5 mL) was added triphenylphosphine (923 mg, 3.5 mmol) in several portions at 0° C. The reaction mixture was stirred for 20 min at the same temperature and then directly passed through a short silica gel column using 10% EtOAc in hexane as an eluent to give the title compound as a transparent oil (300 mg) in 47% yield. Rf (hexane/EtOAc 9:1) 0.44; $^1$H NMR ($CDCl_3$) δ 7.92 (d, 1H, J=7.7 Hz, H-3), 7.82 (t, 1H, J=7.7 Hz, H-4), 7.61 (d, 1H, J=7.7 Hz, H-5), 4.58 (s, 2H, $CH_2Br$), 2.70 (s, 3H, $CH_3CO$); $^{13}$C NMR ($CDCl_3$) δ 200.3 (CO), 156.8 (C-6), 153.6 (C-2), 138.3 (C-4), 127.3 (C-5), 121.1 (C-3), 33.8 ($CH_2Br$), 26.2 ($CH_3$); mass spectrum (ES+): m/e 213.8 ($M^+$+1).

2-Acetyl-6-(hydroxymethyl)pyridine

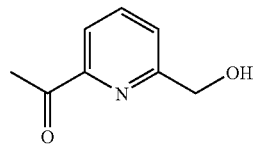

To a THF (10 mL) solution of the silyl ether 2-Acetyl-6-(((tert-butyldimethylsilyl)oxy)methyl)pyridine (0.8 g, 3.0 mmol) was added tetrabutylammonium fluoride hydrate (870 mg, 3.3 mmol) at room temperature, and the mixture was stirred for 40 min. It was extracted with EtOAc (150 mL) and washed with water (6 mL×3) and brine (6 mL). The extract was dried over $MgSO_4$ and evaporated under reduced pressure. The residue was purified by column chromatography on silica gel eluted with hexane/EtOAc 4:1 to give the title compound (450 mg, 99%) as an oil. $^1$H NMR ($CDCl_3$) δ 8.00 (d, 1H, J=7.2 Hz, H-3), 7.88 (m, 1H, H-4), 7.49 (d, 1H, J=7.7 Hz, H-5), 4.88 (d, 2H, J=5.0 Hz, $CH_2$), 3.84 (d, 1H, J=3.2 Hz, OH), 2.78 (s, 3H, $CH_3$); $^{13}$C NMR ($CDCl_3$) δ 200.0 (CO), 159.1 (C-6), 152.7 (C-2), 138.0 (C-4), 124.4 (C-5), 120.8 (C-3), 64.3 ($CH_2$), 26.3 ($CH_3$).

2-Acetyl-6-(((tert-butyldimethylsilyl)oxy)methyl) pyridine

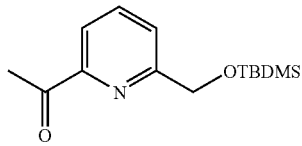

To a stirred solution of 2-Bromo-6-(((tert-butyldimethylsilyl)oxy)methyl)pyridine (1.59 g, 5.26 mmol) in a mixture of ether, hexane and THF (2:1:1, 105 mL) was added n-BuLi (3.29 mL, 5.26 mmol, 1.6 M in hexane solution) dropwise at −78° C. during 5-10 min. To the resulting dark brown solution was dropped anhydrous DMA (0.74 mL, 7.89 mmol) at the same temperature. The reaction mixture was stirred for 30 min and then quenched with water (8 mL) and extracted with EtOAc. The organic layer was washed with water and brine and dried over $MgSO_4$. After purification by column chromatography on silica gel (hexane/EtOAc 98:2) 0.78 g (56%) of the title compound as an oil were obtained. $^1$H NMR ($CDCl_3$) δ 7.95 (d, 1H, J=7.5 Hz, H-3), 7.88 (t, 1H, J=7.6 Hz, H-4), 7.73 (t, 1H, J=7.6 Hz, H-5), 4.93 (s, 2H, $CH_2$), 2.75 (s, 3H, $CH_3$), 1.03 (s, 9H, $(CH_3)_3C$), 0.20 (s, 6H, $(Me)_2Si$); $^{13}$C NMR ($CDCl_3$) δ 200.8 (CO), 161.4 (C-6), 153.0 (C-2), 139.4 (C-4), 124.0 (C-5), 118.0 (C-3), 66.4 ($CH_2$), 26.3 (($\underline{CH_3})_3C$), 18.8 (($CH_3)_3\underline{C}$), -4.96 (($Me)_2Si$).

2-Bromo-6-(((tert-butyldimethylsilyl)oxy)methyl)pyridine

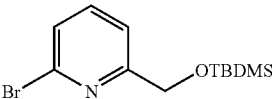

To a mixture of 2-bromo-6-hydroxymethylpyridine (1.03 g, 5.48 mmol) and imidazole (1.49 g, 21.92 mmol) in DMF (5 mL) was added $^t$BuMe$_2$SiCl (991 mg, 6.58 mmol) in several portions at room temperature. The mixture was stirred for 15 min and extracted with ether (50 mL). The extract was washed with water (5 mL×3), dried over MgSO$_4$, and concentrated under reduced pressure. The residue was purified by column chromatography on silica gel eluted with 2.5% of EtOAc in hexane to give the title compound (1.59 g, 96%) as an oil. $^1$H NMR (CDCl$_3$) δ 7.65-7.40 (m, 3H), 4.89 (s, 2H, CH$_2$), 1.04 (s, 9H), 0.20 (s, 6H); $^{13}$C NMR (CDCl$_3$) δ 163.6 (C-6), 141.3 (C-2), 139.4 (C-4), 126.4 (C-3), 119.1 (C-5), 65.9 (CH$_2$), 26.3 ((CH$_3$)$_3$C), 18.8 ((CH$_3$)$_3$C), -5.0 ((Me)$_2$Si).

2-Bromo-6-(methylaminomethylcarbonyl)pyridine and 2-bromo-6-hydroxymethylpyridine

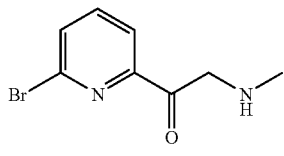

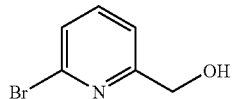

To a stirred solution of 2,6-dibromopyridine (3 g, 12.7 mmol) in a mixture of THF (8 mL), ether (16 mL), and hexane (8 mL) was added n-BuLi (7.94 mL, 12.7 mmol, 1.6 M in hexane) drop-by-drop at −78° C. over 5 min. After the mixture was stirred for 5 min, DMF (2.01 mL, 26.3 mmol) was slowly added dropwise to the mixture over 10 min at the same temperature. The reaction mixture was warmed to −50° C. and quenched with MeOH (15 mL). Then, NaBH$_4$ (487 mg, 12.9 mmol) was added at room temperature. After addition of acetone (1.5 mL), the mixture was diluted with EtOAc (300 mL). The whole was washed with water (6 mL×3) and brine (6 mL) and dried over MgSO$_4$. Solvent was evaporated and the residue was purified by column chromatography on silica gel eluted with 20% EtOAc in hexane to give 380 mg (13%) of 2-Bromo-6-(methylaminomethylcarbonyl)pyridine and 1.11 g (46%) of the oil 2-bromo-6-hydroxymethylpyridine. Bromo-6-(methylaminomethylcarbonyl)pyridine: $^1$H NMR (CDCl$_3$) δ 7.53 (m, 1H, H-4), 7.38 (d, 1H, J=7.9 Hz), 7.28 (d, 1H, J=7.5 Hz), 5.14 (s, 2H, CH$_2$), 2.12 (s,3H, Me); $^{13}$C NMR (CDCl$_3$) δ 170.9 (CO), 157.7 (C-6), 142.1 (C-2), 139.5 (C-4), 127.7 (C-3), 120.9 (C-5), 66.4 (CH$_2$), 21.3 (Me). Mass spectrum (ES+): m/e 230 (M$^+$+1). 2-bromo-6-hydroxymethylpyridine: $^1$H NMR (CDCl$_3$) δ 7.56 (t, 1H, J=7.7 Hz), 7.46 (d, 1H, J=7.7 Hz), 7.37 (d, 1H, J=7.7 Hz), 4.85 (s, 2H, CH$_2$); $^{13}$C NMR (CDCl$_3$) δ 162.0 (C-6), 141.7 (C-2), 139.6 (C-4), 124.8 (C-3), 119.8 (C-5), 64.6 (CH$_2$).

Example 5

N$^6$-(4-iodo-2-picolyl)-2-(2-phenyl-1-ethynyl)-adenosine-5'-N-methyluronamide

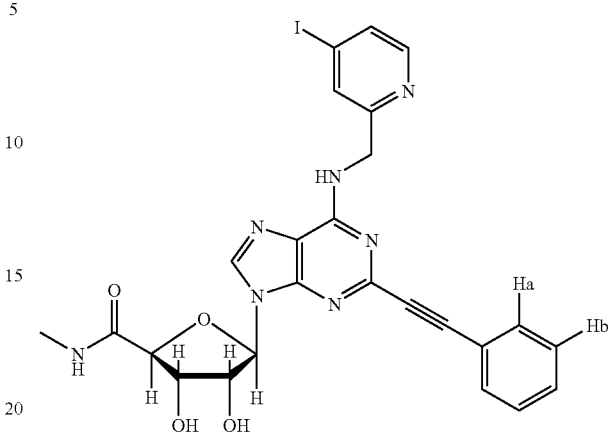

N-Methyl-1'-deoxy-1'-[6-chloro-2-(2-phenyl-1-ethynyl)-9H-purin-9-yl]-2',3'-O-isopropylidene-β-D-ribofuranuronamide (210 mg, 0.47 mmol), (4-iodo-2-pyridyl)methylamine (219 mg, 0.93 mmol), and triethylamine (0.2 mL, 1.41 mmol) were dissolved in absolute ethanol (3.0 mL). The solution was stirred at 65° C. for 16 h in a sealed vessel. The solvent was removed under nitrogen and the 2',3'-O-isopropylidene derivative was purified by column chromatography (2% MeOH in CH$_2$Cl$_2$) yielding 230 mg. HCl (1 N) (3.0 mL) were added and the solution stirred at 70° C. for 45 min. A white precipitate appeared immediately. After cooling, NaHCO$_3$ was added until pH 7, and a white solid precipitated. The solid was filtered and washed with water yielding 138 mg (48% yield overall) of the title compound. $^1$H NMR (DMSO-d$_6$) δ 8.69 (s, 1H, NH), 8.60 (s, 2H, NHCO, H-8), 8.26 (d, 1H, J=5.0 Hz, H-6$_{py}$), 7.87 (s, 1H, H-3$_{py}$), 7.78 (d, 1H, J=5.0 Hz, H-5$_{py}$), 7.62 (2H, m, C$_6$H$_5$), 7.47 (3H, m, C$_6$H$_5$), 6.02 (d, 1H, J=7.5 Hz, H-1'), 4.82 (bs, 2H, CH$_2$—N), 4.63 (dd, 1H, J$_1$=7.5, J$_2$=4.6 Hz, H-2'), 4.35 (s, 1H, H-4'), 4.18 (d, 1H, J=4.1 Hz, H-3'), 2.78 (d, 3H, J=4.5 Hz, 5'-N-methyl). $^{13}$C NMR (DMSO-d$_6$) δ 170.2 (CO), 159.6 C-2$_{py}$), 154.5 (C-6), 149.3 (C-6$_{py}$), 148.9 (C-4), 145.5 (C-2), 142.4 (C-8), 132.2 (C-Ha), 131.7 (C-5$_{py}$) 130.8 (para-C), 130.1 (C-3$_{py}$), 129.3 (C-Hb), 121.2 (ipso-C), 90.0 (□-alkynyl), 88.0 (C-1'), 85.0 (C-4'), 84.1 (□-alkynyl), 73.4 (C-3'), 72.5, (C-2'), 44.4 (CH$_2$), 26.0 (5'-N-methyl). Anal. (C$_{25}$H$_{22}$N$_7$O$_4$I) C, H, N. High-resolution MS calcd for (C$_{25}$H$_{22}$N$_7$O$_4$NaI) 634.0684, found 634.0676.

N-methyl-1'-deoxy-1'-[6-chloro-2-(2-phenyl-1-ethynyl)-9H-purin-9-yl]-2', 3'-O-isopropylideneδ-D-ribofuranuronamide

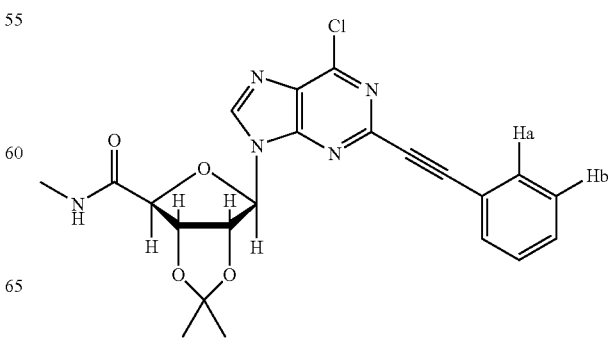

To a solution of 500 mg (1.04 mmol) of N-methyl-1'-deoxy-1'-(6-chloro-2-iodo-9H-purin-9-yl)-2',3'-O-isopropylidene-β-D-ribofuranuronamide in 10 mL of dry acetonitrile, and 4.5 mL of triethylamine under an argon atmosphere was added 14.5 mg (0.0206 mmol) of bis(triphenylphosphine) palladium dichloride and 1.0 mg (0.0054 mmol) of cuprous iodide. To the mixture was added phenylacetylene (0.17 mL, 1.56 mmol), and the reaction mixture was stirred at room temperature for 1 hour. The solvent was removed in vacuo, and the residue was chromatographed on a silica gel column (2% MeOH in $CH_2Cl_2$) to give 454 mg (96%) of the title compound. $^1$H NMR ($CDCl_3$) δ 8.29 (s, 1H, H-8), 7.73 (2H, m, $C_6H_5$), 7.47 (3H, m, $C_6H_5$), 7.13 (m, 1H, NH), 6.17 (d, 1H, J=3.5 Hz, H-1'), 5.35 (m, 2H, H-3', H-2'), 4.82 (d, 1H, J=1.8 Hz, H-4'), 2.86 (d, 3H, J=4.9 Hz, 5'-N-methyl), 1.70, 1.44 (2 s, 2 3H, 2 $CH_3$, isopropylidene). $^{13}$C NMR ($CDCl_3$) δ 169.3 (CO), 152.3, 151.3, 146.6 (C-2), 145.6 (C-8), 133.0 (C-Ha), 132.1 (C-5), 130.6 (para-C), 129.1 (C-Hb), 121.2 (ipso-C), 115.6 (Cq, isopropylidene), 92.8 (C-1'), 89.5 (β-alkynyl), 87.8 (β-alkynyl), 85.6 (C-4'), 83.7, 82.7 (C-3', C-2'), 27.7, 26.5, 25.6 (2 $CH_3$, isopropylidene, 5'-N-methyl). Mass spectrum (ES+): m/e 454 ($M^+$+1).

N-methyl-1'-deoxy-1'-(6-chloro-2-iodo-9H-purin-9-yl)-2',3'-O-isopropylidene-β-D-ribofuranuronamide

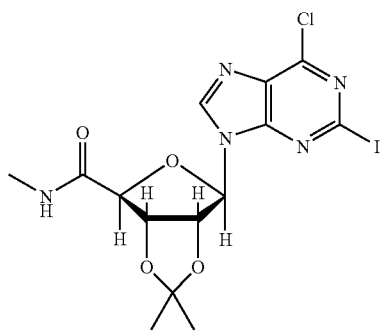

Freshly isoamyl nitrite (0.74 mL, 5.47 mmol) was added to a mixture of N-methyl-1'-deoxy-1'-(2-amino-6-chloro-9H-purin-9-yl)-2',3'-O-isopropylidene-β-D-ribofuranuronamide (618 mg, 1.68 mmol), CuI (339 mg, 1.78 mmol), $CH_2I_2$ (1.35 mL, 16.8 mmol), and $I_2$ (426 mg, 1.68 mmol) in dry THF (6.0 mL) at room temperature and under argon. The reaction mixture was refluxed for 30 min, cooled to ambient temperature, filtered to remove insolubles, and then evaporated. The product was purified by flash chromatography. Iodine was first eluted from the column with 100% of $CH_2Cl_2$ and then the title compound was eluted with 2% MeOH in $CH_2Cl_2$ in 62% yield. $^1$H NMR ($CDCl_3$) δ 8.25 (s, 1H, H-8), 6.60 (m, 1H, NH), 6.19 (d, 1H, J=2.8 Hz, H-1'), 5.37, 5.29 (m, 2H, H-3', H-2'), 4.74 (d, 1H, J=2.1 Hz, H-4'), 2.75 (d, 3H, J=4.9 Hz, 5'-N-methyl), 1.63, 1.40 (2 s, 2 3H, 2 $CH_3$, isopropylidene). $^{13}$C NMR ($CDCl_3$) δ 169.1 (CO), 152.1, 151.5, 145.2 (C-8), 132.7 (C-5), 117.4 (C-2), 115.4 (Cq, isopropylidene), 92.2 (C-1'), 86.5 (C-4'), 83.6, 83.3 (C-3', C-2'), 27.4, 26.8, 25.6 (2 $CH_3$, isopropylidene, 5'-N-methyl).

N-methyl-1'-deoxy-1'-(2-amino-6-chloro-9H-purin-9-yl)-2',3'-O-isopropylidene-β-D-ribofuranuronamide

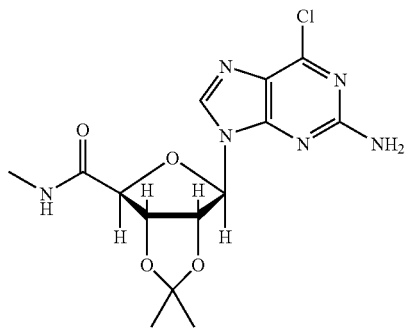

To a mixture of pre-dried 5'-N-Methyl-2,3'-O-isopropylidenecarboxamidoguanosine (950 mg, 2.71 mmol), $Et_4NCl$ (898 mg, 5.42 mmol, pre-dried in vacuo at 90° C. overnight over $P_2O_5$), N,N-dimethylaniline (0.34 mL, 2.71 mmol) in anhydrous acetonitrile (20 mL), 1.5 mL (16.26 mmol) of phosphoryl chloride were added at room temperature. The flask was placed in an oil bath pre-heated to 100° C. and the solution was heated with stirring at reflux for 10 minutes. Volatile materials were flash evaporated immediately in vacuo. The resulting yellow foam was dissolved in 15 mL of $CHCl_3$ and stirred vigorously with crushed ice for 15 minutes. The layers were separated and the aqueous phase was extracted with 5×5 mL of $CHCl_3$. The combined organic phase was kept cold by addition of crushed ice. It was washed with cold water, 5% of $NaHCO_3$ to pH~7, dried over $MgSO_4$, and filtered. The product was purified by column chromatography (3% MeOH in $CH_2Cl_2$) to give 840 mg (84%) of the title compound as a white crystalline product. $^1$H NMR ($CDCl_3$) δ 7.87 (s, 1H, H-8), 6.35 (m, 1H, NH), 6.12 (d, 1H, J=1.2 Hz, H-1'), 5.70 (s, 2H, $NH_2$), 5.66 (dd, 1H, $J_1$=6.2, $J_2$=2.0 Hz, H-3'), 5.29 (d, 1H, J=1.1 Hz, H-2'), 4.73 (d, 1H, J=1.6 Hz, H-4'), 2.52 (d, 3H, J=4.9 Hz, 5'-N-methyl), 1.59, 1.39 (2 s, 2 3H, 2 $CH_3$, isopropylidene). $^{13}$C NMR ($CDCl_3$) δ 170.3 (CO), 151.9, 159.6 (C-2), 153.0, 152.1, 142.0 (C-8), 125.5 (C-5), 114.3 (Cq, isopropylidene), 91.9 (C-1'), 88.5 (C-4'), 84.1, 84.2 (C-3', C-2'), 27.1, 25.5 (2 $CH_3$, isopropylidene), 26.1 (5'-N-methyl).

5'-N-Methyl-2',3'-O-isopropylidenecarboxamidoguanosine

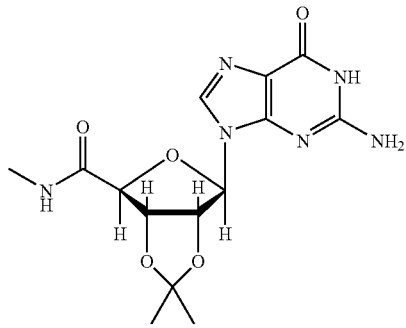

2',3'-O-Isopropylideneguanosine-5'-carboxylic acid (1.6 g, 4.6 mmol) was coevaporated with DMF (3×20 mL) and taken up in DMF (20 mL) with Et$_3$N (0.94 mL, 6.9 mmol) under N$_2$ atmosphere. After the solution was cooled to 0° C., the coupling reagent isopropenyl chloroformate (1.0 g, 8.30 mmol) and methylamine 2.0 M in THF (5.3 mL, 10.6 mmol) were added subsequently. The reaction mixture was stirred for 15 min at 0° C. The mixtures were concentrated under reduce pressure, redissolved in CH$_2$Cl$_2$ washed with NaHCO$_3$ solution (10%) and water, dried on MgSO$_4$ and concentrated. The remaining oils were purified by column chromatography (eluent CH$_2$Cl$_2$/MeOH 9:1) and 693 mg (43%) of the title compound were obtained. $^1$H NMR (CD$_3$OD) δ 7.87 (s, 1H, H-8), 6.21 (s, 1H, H-1'), 5.64 (dd, 1H, J$_{2',3'}$=6.1 Hz, J$_{2',1'}$=1.9 Hz, H-2'), 5.37 (d, 1H, J$_{3',2'}$=6.1 Hz, H-3'), 4.63 (s, 1H, H-4'), 2.47 (s, 3H, 5'-N-methyl), 1.56, 1.40 (2 s, 2 3H, 2 CH$_3$, isopropylidene).

Example 6

N$^6$-[(2-dimethylamino-7-iodo-1,3-benzoxazol-5-yl)-methyl]-adenosine-5'-N-methyluronamide

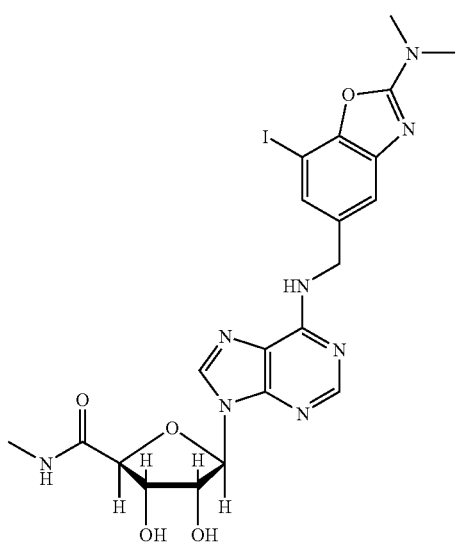

2',3'-O-Isopropylidene-6-chloropurine-5'-methyluronamide (72 mg, 0.2 mmol), N2,N2-dimethyl-5-(aminomethyl)-7-iodo-1,3-benzoxazol-2-amine (64 mg, 0.2 mmol), and triethylamine (0.084 mL, 0.6 mmol) were dissolved in absolute ethanol (1.0 mL). The solution was stirred at 65° C. for 16 h in a sealed vessel. The solvent was removed under nitrogen. HCl (1 N) (1.0 mL) was added and the solution stirred at 70° C. for 45 min. After cooling, NaHCO$_3$ was added until pH 7, and a white solid precipitated. The solid was filtered and washed with water yielding 60 mg (50% yield overall) of the title compound. M.p. 196-198° C.; $^1$H NMR (DMSO-d$_6$) δ 8.92 (bs, 1H, NHCO), 8.61 (s, 1H, NH), 8.46 (s, 1H, H-8), 8.33 (s, 1H, H-2), 7.32 (s, 1H, H$_{benzoxazol}$-6), 7.20 (s, 1H, H$_b$-4), 5.98 (d, 1H, J$_{1',2'}$=7.6 Hz, H-1'), 5.77 (d, 1H, J=2.5 Hz, OH-3'), 5.58 (d, 1H, J=5.1 Hz, OH-2'), 4.70 (s, 2H, —CH$_2$N—), 4.60 (bs, 1H, H-2'), 4.32 (s, 1H, H-4'), 4.15 (bs, 1H, H-3'), 3.11 (s, 6H, (CH$_3$)$_2$N), 2.72 (d, 3H, J=4.5 Hz, 5'-N-methyl). $^{13}$C NMR (DMSO-d$_6$) δ 168.5 (C-5'), 160.6 (C$_b$-2), 153.0 (C-6), 151.2 (C-2), 147.8 (C-4), 146.1 (C$_b$-7a), 141.6 (C$_b$-3a), 139.4 (C-8), 136.7 (C$_b$-5), 125.8 (C$_b$-6), 118.7 (C-5), 113.0 (C$_b$-4), 86.4 (C-1'), 83.3 (C-4'), 71.7, 70.7 (C-3', C-2'), 69.7 (C$_b$-7), 47.2 (CH$_2$), 35.9 ((CH$_3$)$_2$N), 24.0 (5'-N-methyl). Anal. (C$^{21}$H$_{23}$N$_8$O$_5$I) C, H, N.

Synthesis of N2,N2-dimethyl-5-(aminomethyl)-7-iodo-1,3-benzoxazol-2-amine

The N2,N2-dimethyl-5-(aminomethyl)-7-iodo-1,3-benzoxazol-2-amine used in the above synthesis was made by the following procedure.

3-Bromo-4-hydroxy-5-nitrobenzonitrile

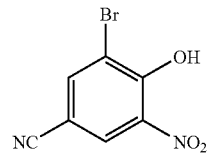

To a mixture of 5 g (30.5 mmol) of 4-hydroxy-3-nitrobenzonitrile in H$_2$SO$_4$ solution (50 mL of concentrated H$_2$SO$_4$+ 50 mL of H$_2$O) at 25° C., 7.9 g (47.3 mmol) of potassium bromate were added in small portions cooling the flask with an ice-bath and maintaining the temperature between 25 and 35° C. After the addition was completed, the reaction was stirred at room temperature for 22 h and then filtered. The pale yellow solid was washed with water and dried to give 4.2 g (57%) of the title compound. M.p.: 162-164° C.; $^1$H NMR (CD$_3$OD) δ 8.54 (d, 1H, J=2.0 Hz, H-6), 8.32 (d, 1H, J=2.0 Hz, H-2); $^{13}$C NMR (DMSO-d$_6$) δ 153.9 (C-4), 140.8 (C-2), 138.2 (C-5), 130.1 (C-6), 117.0 (CN), 115.9 (C-3), 101.6 (C-1).

2-amino-4-(aminomethyl)-6-bromophenol

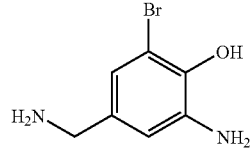

A solution of 3-bromo-4-hydroxy-5-nitrobenzonitrile (1.0 g, 4.11 mmol) in 20.0 mL of dry THF was added dropwise to a solution of BH$_3$/THF 1.0 M in THF (12.3 mL) at 0° C. under N$_2$. The reaction mixture was stirred at room temperature for 24 hours. Excess borane was decomposed by the cautious dropwise addition of 1 N HCl at 0° C. It was extracted with EtOAc, washed with NaHCO$_3$, NaCl saturated solution and dried (Na$_2$SO$_4$ anh.) to give a crude. After purification by column chromatography (CH$_2$Cl$_2$/MeOH 8:2+1% NH$_4$OH), 170 mg (19%) of 2-amino-4-(aminomethyl)-6-bromophenol were obtained. $^1$H NMR (DMSO-d$_6$) δ 6.67 (s, 1H, H-5); 6.53 (s, 1H, H-3); 3.52 (s, 2H, CH$_2$). $^{13}$C NMR (DMSO-d$_6$) δ 139.7, 139.4 (C-1, C-4), 136.0 (C-2), 118.5 (C-5), 113.0 (C-3), 111.5 (C-6), 44.9 (CH$_2$).

Tert-butylN—(3-amino-5-bromo-4-hydroxybenzyl)carbamate

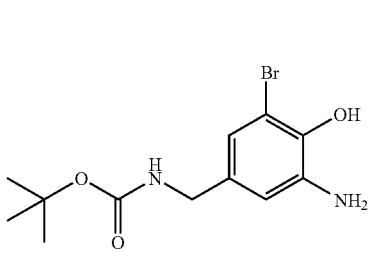

To a solution of 2-amino-4-(aminomethyl)-6-bromophenol (560 mg, 2.59 mmol) in 15 mL of DMF, triethylamine (0.37 mL, 2.63 mmol) and di-tert-butyldicarbonate (0.59 mL, 2.59 mmol) were added. The mixture was stirred at room temperature for 1 hour and 15 minutes. The solvent was evaporated and the residue was suspended in EtOAc and filtered. The solution was extracted with 0.5 M NaH$_2$PO$_4$ (3×) and dried. The product was purified by column chromatography (2% MeOH in CH$_2$Cl$_2$) yielding 304 mg (37%) of tert-butylN—(3-amino-5-bromo-4-hydroxybenzyl)carbamate. $^1$H NMR (CDCl$_3$) δ 6.76 (d, 1H, J=1.8 Hz, H-6); 6.57 (d, 1H, J=1.2 Hz, H-2); 4.13 (d, 2H, J=5.8 Hz, CH$_2$); 1.49 (s, 9H, (CH$_3$)$_3$C); $^{13}$C NMR (CDCl$_3$) δ 156.5 (CO), 140.1 (C-4), 136.9 (C-1), 133.0 (C-3), 120.3 (C-6), 114.3 (C-2), 110.7 (C-5), 79.8 ((CH$_3$)$_3$C), 44.2 (CH$_2$), 28.8 ((CH$_3$)$_3$C).

Tert-butylN-{[7-bromo-2-(dimethylamino)-1,3-benzoxazol-5-yl]methyl}carbamate

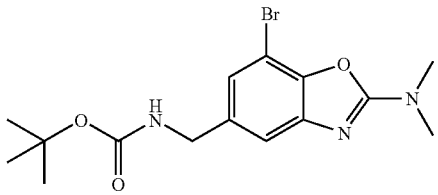

A mixture of tert-butylN—(3-amino-5-bromo-4-hydroxybenzyl)carbamate (300 mg, 0.95 mmol) and dichloromethylenedimethylammonium chloride (phosgene iminium chloride, 240 mg, 1.48 mmol) in 10 mL of dry CH$_2$Cl$_2$ was refluxed for 6 h. After cooling the solution was extracted with EtOAc, washed with NaHCO$_3$, brine and dried (MgSO$_4$). After purification by column chromatography (1% MeOH in CH$_2$Cl$_2$) 192 mg (55%) of tert-butylN-{[7-bromo-2-(dimethylamino)-1,3-benzoxazol-5-yl]methyl}carbamate were obtained. $^1$H NMR (CDCl$_3$) δ 7.14 (s, 1H, H-6); 7.04 (s, 1H, H-4); 5.11 (bs, 1H, NH); 4.31 (d, 2H, J=5.6 Hz, CH$_2$); 3.23, 3.22 (s, 6H, NCH$_3$ 2×); 1.48 (s, 9H, (CH$_3$)$_3$C); $^{13}$C NMR (CDCl$_3$) δ 163.3 (C-2), 156.2 (CO), 146.6 (C-7a), 145.1 (C-3a), 137.0 (C-5), 122.8 (C-6), 114.3 (C-4), 100.6 (C-7), 79.9 ((CH$_3$)$_3$C), 44.7 (CH$_2$), 38.1 (NCH$_3$×2), 28.8 ((CH$_3$)$_3$C).

Tert-butylN-{[2-(dimethylamino)-7-iodo-1,3-benzoxazol-5-yl]methyl}carbamate

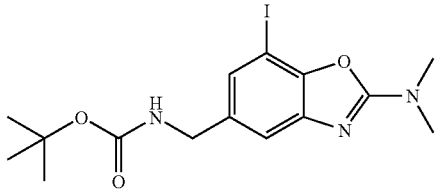

A mixture of tert-butyl-{[7-bromo-2-(dimethylamino)-1,3-benzoxazol-5-yl]methyl}carbamate (192 mg, 0.52 mmol), KI (1.3 g, 7.8 mmol), CuI (495 mg, 2.6 mmol) in 1.6 mL of HMPA was stirred overnight (16 h) at 135° C. After cooling, the mixture was extracted with EtOAc, washed with Na$_2$S$_2$O$_3$ 0.5 M solution, and brine (×3). After purification by column chromatography (hexane/EtOAc 6:4), 120 mg (55%) of tert-butylN-{[2-(dimethylamino)-7-iodo-1,3-benzoxazol-5-yl]methyl}carbamate were obtained. $^1$H NMR (CDCl$_3$) δ 7.32 (s, 1H, H-6); 7.27 (s, 1H, H-4); 5.02 (bs, 1H, NH); 4.40 (d, 2H, J=5.4 Hz, CH$_2$); 3.32 (s, 6H, NCH$_3$ 2×); 1.57 (s, 9H, (CH$_3$)$_3$C); $^{13}$C NMR (CDCl$_3$) δ 162.7 (C-2), 156.2 (CO), 150.4 (C-7a), 143.8 (C-3a), 137.4 (C-5), 128.4 (C-6), 115.3 (C-4), 80.0 ((CH$_3$)$_3$C), 70.5 (C-7), 44.6 (CH$_2$), 38.1 (NCH$_3$×2), 28.8 ((CH$_3$)$_3$C).

N2,N2-dimethyl-5-(aminomethyl)-7-iodo-1,3-benzoxazol-2-amine

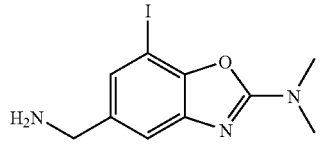

To a solution of tert-butylN-{[2-(dimethylamino)-7-iodo-1,3-benzoxazol-5-yl]methyl}carbamate (120 mg, 0.29 mmol) in 4 ml of CH$_2$Cl$_2$ was added slowly 0.5 mL of trifluoroacetic acid and it was stirred at room temperature for 30 min. The excess of TFA was removed under vacuum. The product was purified by column chromatography (CH$_2$Cl$_2$/MeOH 9:1) yielding 64 mg (70%) of N2,N2-dimethyl-5-(aminomethyl)-7-iodo-1,3-benzoxazol-2-amine as a white solid. $^1$H NMR (CD$_3$OD) δ 7.46 (d, 1H, J=1.5 Hz, H-6); 7.30 (d, 1H, J=1.5 Hz, H-4); 4.12 (s, 2H, CH$_2$); 3.23, 3.24 (s, 6H, CH$_3$×2); $^{13}$C NMR (CD$_3$OD) δ 164.5 (C-2), 152.7 (C-7a), 144.6 (C-3a), 132.9 (C-5), 131.6 (C-6), 117.3 (C-4), 72.0 (C-7), 44.2 (CH$_2$), 38.3 (CH$_3$).

Example 7

N$^6$-[(2-Dimethylamino-1,3-benzoxazol-5-yl)-methyl]-adenosine-5'-N-methyluronamide

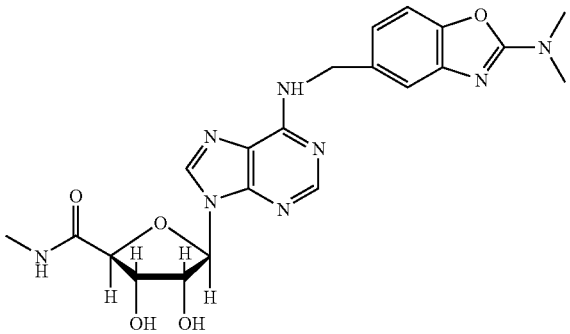

2',3'-O-isopropylidene-6-chloropurine-5'-methyluronamide (100 mg, 0.28 mmol), N2,N2-dimethyl-5-(aminomethyl)-1,3-benzoxazol-2-amine (80.3 mg, 0.42 mmol), and triethylamine (0.117 mL, 0.84 mmol) were dissolved in absolute ethanol (1.5 mL). The solution was stirred at 65° C. for 16 h in a sealed vessel. The solvent was removed under nitrogen. The 2',3'-O-isopropylidene derivative was purified by column chromatography (3% MeOH in CH$_2$Cl$_2$). HCl (1 N) (1.2 mL) was added and the solution stirred at 70° C. for 45 min. After cooling, NaHCO$_3$ was added until pH 7, and the solution was left overnight crystallizing. The white solid was filtered and washed with water yielding 68 mg (52%) of the title compound. M.p.: 239-241° C.; $^1$H NMR (DMSO-d$_6$) δ 8.94 (bs, 1H, NHCO), 8.57 (s, 1H, NH), 8.44 (s, 1H, H-8), 8.33 (s, 1H, H-2), 7.29 (d, 1H, J=8.2 Hz, H$_{benzoxazol}$-7), 7.24 (s, 1H, H$_b$-4), 6.99 (d, 1H, J=8.2 Hz, H$_b$-6), 5.98 (d, 1H, J$_{1',2'}$=7.5 Hz, H-1'), 5.75 (s, 2H, OH-2',3'), 4.73 (s, 2H, —CH$_2$N—), 4.61 (dd, 1H, J$_{2',1'}$=7.5 Hz, J$_{2',3'}$=4.6 Hz, H-2'), 4.33 (s, 1H, H-4'), 4.15 (d, 1H, J$_{3',2'}$=4.6 Hz, H-3'), 3.1 (s, 6H, (CH$_3$)$_2$N), 2.73 (d, 3H, J=3.9 Hz, 5'-N-methyl); $^{13}$C NMR (DMSO-d$_6$) δ 168.4 (C-5'), 161.4 (C$_b$-2), 153.0 (C-4), 151.0 (C-2), 146.7 (C-6), 146.1 (C$_b$-7a), 142.0 (C$_b$-3a), 139.2 (C-8), 134.2 (C$_b$-5), 118.5 (C-5), 117.6 (C$_b$-6), 112.9 (C$_b$-4), 106.7 (C$_b$-7), 86.3 (C-1'), 83.2 (C-4'), 71.6, 70.5 (C-3', C-2'), 41.5 (CH$_2$), 35.7 ((CH$_3$)$_2$N), 23.9 (5'-N-methyl). High-resolution MS calcd for (C$^{21}$H$_{24}$N$_8$O$_5$Na) 491.1767, found 491.1749. Anal. (C$^{21}$H$_{24}$N$_8$O$_5$) C, H, N.

N2,N2-Dimethyl-5-(aminomethyl)-1,3-benzoxazol-2-amine

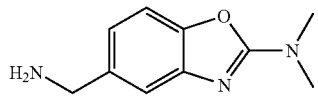

To a mixture of 2-(Dimethylamino)-1,3-benzoxazole-5-carbonitrile (1.5 g, 8.0 mmol) in 150 mL of dry ether, 640 mg (16.0 mmol) of LiAlH$_4$ were slowly added. The mixture was stirred at room temperature for 1.5 h and the excess of reagent was decomposed by careful addition of the minimum amount of water and filtered. The solids were washed with hot EtOAc (3×100 mL) giving a residue after evaporation. The purification by column chromatography yield 622 mg (41%) of the title compound as a white solid. Rf (CH$_2$Cl$_2$/MeOH 9:1+ 0.25% NH$_3$) 0.2; $^1$H NMR (CD$_3$OD) δ 7.23 (s, 1H, H-4), 7.15 (d, 1H, J=8.1 Hz, H-7), 6.89 (d, 1H, J=8.1 Hz, H-6), 3.83 (s, 2H, CH$_2$), 3.14 (s, 6H, CH$_3$×2); $^{13}$C NMR (CD$_3$OD) δ 163.7 (C-2), 148.4 (C-7a), 144.2 (C-3a), 139.5 (C-5), 119.6 (C-6), 114.9 (C-4), 108.7 (C-7), 47.1 (CH$_2$), 38.0 (CH$_3$); mass spectrum (ES+): m/e 192.0 (M$^+$+1).

2-(Dimethylamino)-1,3-benzoxazole-5-carbonitrile

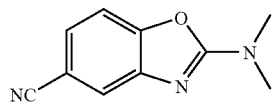

A mixture of 3-Amino-4-hydroxybenzonitrile (2 g, 14.9 mmol) and dichloromethylenedimethylammonium chloride (phosgene iminium chloride, 2.42 g, 14.9 mmol) in 50 mL of dry CH$_2$Cl$_2$ was refluxed for 6 h. After cooling the solution was extracted with EtOAc, washed with NaHCO$_3$, brine and dried (MgSO$_4$). The residue was crystallized in MeOH yielding 2.51 g (90%) of the title compound as a white solid. M.p.: 198-200° C., $^1$H NMR (CD$_3$OD) δ 7.61 (d, 1H, J=2.8 Hz, H-4), 7.36-7.32 (m, 2H, H-6, H-7), 3.28 (s, 6H, CH$_3$×2); $^{13}$C NMR (CD$_3$OD) δ 164.4 (C-2), 152.2 (C-7a), 145.0 (C-3a), 125.4 (C-6), 120.0 (CN), 119.9 (C-4), 109.8 (C-7), 108.0 (C-5), 38.2 (CH$_3$).

3-Amino-4-hydroxybenzonitrile

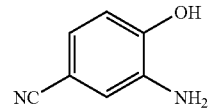

To a mixture of 5 g (30.5 mmol) of 4-hydroxy-3-nitrobenzonitrile, 18.1 g of powder tin metal (152.5 mmol, 325 mesh), and 45 mL of ethanol was added with stirring a solution of 10 mL of concentrated HCl in 30 mL of H$_2$O. The suspension was heated at reflux for 45 min and the resulting hot solution was poured into 100 mL of H$_2$O. Saturated aqueous NaHCO$_3$ solution was slowly added to bring the pH to ca. 7. The suspension was filtered, and the residue was washed with MeOH giving the title compound (3.15 g, 77%) as a white powder. Rf (CH$_2$Cl$_2$/MeOH 9:1) 0.47; $^1$H NMR (CD$_3$OD) δ 6.96 (d, 1H, J=1.3 Hz, H-2), 6.92 (d, 1H, J=8.1 Hz, H-6), 6.75 (d, 1H, J=8.1 Hz, H-5); $^{13}$C NMR (CD$_3$OD) δ 151.1 (C-4), 138.6 (C-3), 124.7 (C-6), 121.6 (CN), 119.1 (C-2), 115.9 (C-5), 103.6 (C-1).

Example 8

N$^6$-[(2-dimethylamino-7-iodo-1,3-benzoxazol-5-yl)-methyl]-2-(2-phenyl-1-ethynyl)-adenosine-5'-N-methyluronamide

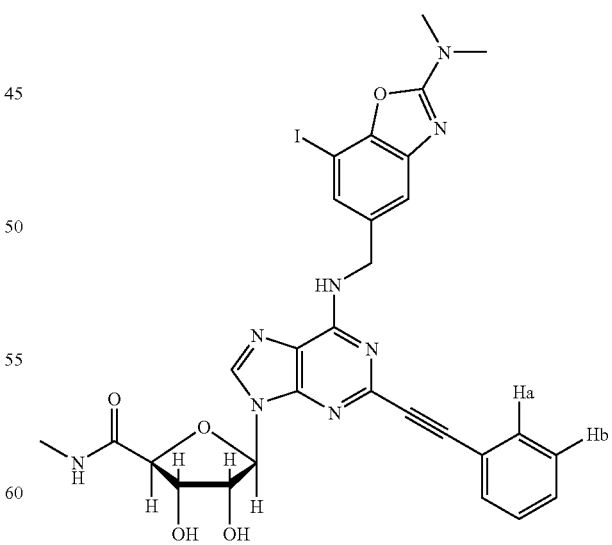

N-Methyl-1'-deoxy-1'-[6-chloro-2-(2-phenyl-1-ethynyl)-9H-purin-9-yl]-2', 3'-O-isopropylidene-δ-D-ribofuranuronamide (170 mg, 0.37 mmol), N2,N2-dimethyl-5-(aminomethyl)-7-iodo-1,3-benzoxazol-2-amine (120 mg, 0.38 mmol), and triethylamine (0.16 mL, 1.11 mmol) were dissolved in absolute ethanol (2.5 mL). The solution was stirred at 65° C. for 16 h in a sealed vessel. The solvent was removed under nitrogen and the 2',3'-O-isopropylidene derivative was purified by column chromatography (2% MeOH in $CH_2Cl_2$) yielding 170 mg. HCl (1 N) (3.0 mL) were added and the solution stirred at 70° C. for 45 min. A white precipitate appeared immediately. After cooling, $NaHCO_3$ was added until pH 7, and a white solid precipitated. The solid was filtered and washed with water yielding 90 mg (35% yield overall) of the title compound. $^1$H NMR (DMSO-$d_6$) δ 8.74 (s, 1H, NH), 8.61 (s, 1H, NHCO), 8.55 (s, 1H, H-8), 7.64 (2H, m, $C_6H_5$), 7.47 (3H, m, $C_6H_5$), 7.37 (s, 1H, $H_{benzoxazol}$-6), 7.22 (s, 1H, $H_b$-4), 6.00 (d, 1H, J=7.6 Hz, H-1'), 5.79 (d, 1H, J=4.3 Hz, OH-3'), 5.61 (d, 1H, J=6.3 Hz, OH-2'), 4.72 (d, 2H, J=4.5 Hz, $CH_2$—N), 4.63 (m, 1H, H-2'), 4.34 (s, 1H, H-4'), 4.18 (m, 1H, H-3'), 3.11 (s, 6H, $(CH_3)_2$N), 2.78 (d, 3H, J=4.5 Hz, 5'-N-methyl). $^{13}$C NMR (DMSO-$d_6$) δ 168.9 (CO), 161.0 ($C_b$-2), 153.2 (C-6), 148.3, 147.5, 144.3 (C-2), 142.0 ($C_b$-3a), 141.0 (C-8), 136.7 ($C_b$-5), 131.0 (C-Ha), 128.8 (para-C), 128.1 (C-Hb), 126.5 ($C_b$-6), 120.0 (ipso-C), 118.8 (C-5), 113.5 ($C_b$-4), 88.9 (β-alkynyl), 86.8 (C-1'), 83.8 (C-4'), 82.7 (β-alkynyl), 72.1 (C-3'), 72.1 (C-2'), 70.2 ($C_b$-7), 41.6 ($CH_2$), 36.4, 36.3 ($(CH_3)_2$N), 24.8 (5'-N-methyl). Anal. ($C_{29}H_{27}N_8O_5I$) C, H, N. High-resolution MS calcd for ($C_{29}H_{27}N_8O_5NaI$) 717.1047, found 717.1060.

N-methyl-1'-deoxy-1'-[6-chloro-2-(2-phenyl-1-ethynyl)-9H-purin-9-yl]-2',3-O-isopropylidene-δ-D-ribofuranuronamide The above compound was prepared as described in example 5.

N2,N2-dimethyl-5-(aminomethyl)-7-iodo-1,3-benzoxazol-2-amine

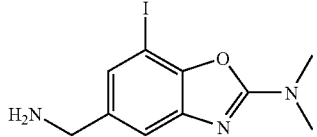

To a solution of Tert-butylN-{[2-(dimethylamino)-7-iodo-1,3-benzoxazol-5-yl]methyl}carbamate (120 mg, 0.29 mmol) in 4 ml of $CH_2Cl_2$ was added slowly 0.5 mL of trifluoroacetic acid and it was stirred at room temperature for 30 min. The excess of TFA was removed under vacuum. The product was purified by column chromatography ($CH_2Cl_2$/MeOH 9:1) yielding 64 mg (70%) of the title compound as a white solid. $^1$H NMR ($CD_3OD$) δ 7.46 (d, 1H, J=1.5 Hz, H-6); 7.30 (d, 1H, J=1.5 Hz, H-4); 4.12 (s, 2H, $CH_2$); 3.23, 3.24 (s, 6H, $CH_3$×2); $^{13}$C NMR ($CD_3OD$) δ 164.5 (C-2), 152.7 (C-7a), 144.6 (C-3a), 132.9 (C-5), 131.6 (C-6), 117.3 (C-4), 72.0 (C-7), 44.2 ($CH_2$), 38.3 ($CH_3$).

Tert-butylN-{[2-(dimethylamino)-7-iodo-1,3-benzoxazol-5-yl]methyl}carbamate

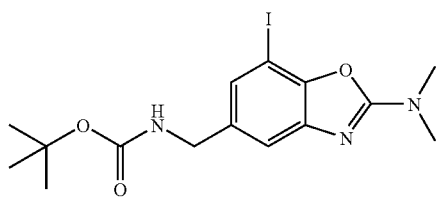

A mixture of tert-butylN-{[7-bromo-2-(dimethylamino)-1,3-benzoxazol-5-yl]methyl}carbamate Tert-butylN-{[7-bromo-2-(dimethylamino)-1,3-benzoxazol-5-yl]methyl}carbamate (192 mg, 0.52 mmol), KI (1.3 g, 7.8 mmol), CuI (495 mg, 2.6 mmol) in 1.6 mL of HMPA was stirred overnight (16 h) at 135° C. After cooling, the mixture was extracted with EtOAc, washed with $Na_2S_2O_3$ 0.5 M solution, and brine (×3). After purification by column chromatography (hexane/EtOAc 6:4), 120 mg (55%) of the title compound were obtained. $^1$H NMR ($CDCl_3$) δ 7.32 (s, 1H, H-6); 7.27 (s, 1H, H-4); 5.02 (bs, 1H, NH); 4.40 (d, 2H, J=5.4 Hz, $CH_2$); 3.32 (s, 6H, $NCH_3$2×); 1.57 (s, 9H, $(CH_3)_3C$); $^{13}$C NMR ($CDCl_3$) δ 162.7 (C-2), 156.2 (CO), 150.4 (C-7a), 143.8 (C-3a), 137.4 (C-5), 128.4 (C-6), 115.3 (C-4), 80.0 (($CH_3)_3\underline{C}$), 70.5 (C-7), 44.6 ($CH_2$), 38.1 ($NCH_3$×2), 28.8 (($\underline{CH_3})_3C$).

Tert-butylN-{[7-bromo-2-(dimethylamino)-1,3-benzoxazol-5-yl]methyl}carbamate

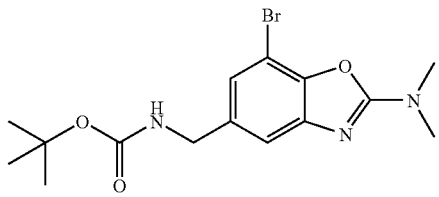

A mixture of Tert-butylN—(3-amino-5-bromo-4-hydroxybenzyl)carbamate (300 mg, 0.95 mmol) and dichloromethylenedimethylammonium chloride (phosgene iminium chloride, 240 mg, 1.48 mmol) in 10 mL of dry $CH_2Cl_2$ was refluxed for 6 h. After cooling the solution was extracted with EtOAc, washed with $NaHCO_3$, brine and dried ($MgSO_4$). After purification by column chromatography (1% MeOH in $CH_2Cl_2$) 192 mg (55%) of the title compound were obtained. $^1$H NMR ($CDCl_3$) δ 7.14 (s, 1H, H-6); 7.04 (s, 1H, H-4); 5.11 (bs, 1H, NH); 4.31 (d, 2H, J=5.6 Hz, $CH_2$); 3.23, 3.22 (s, 6H, $NCH_3$ 2×); 1.48 (s, 9H, $(CH_3)_3C$); $^{13}$C NMR ($CDCl_3$) δ 163.3 (C-2), 156.2 (CO), 146.6 (C-7a), 145.1 (C-3a), 137.0 (C-5), 122.8 (C-6), 114.3 (C-4), 100.6 (C-7), 79.9 (($CH_3)_3\underline{C}$), 44.7 ($CH_2$), 38.1 ($NCH_3$×2), 28.8 (($\underline{CH_3}$)$_3$C).

Tert-butylN—(3-amino-5-bromo-4-hydroxybenzyl)carbamate

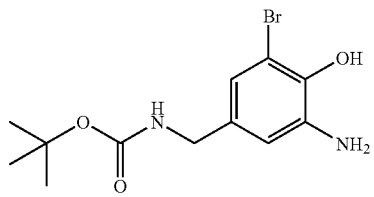

To a solution of 2-amino-4-(aminomethyl)-6-bromophenol (560 mg, 2.59 mmol) in 15 mL of DMF, triethylamine (0.37 mL, 2.63 mmol) and di-tert-butyldicarbonate (0.59 mL, 2.59 mmol) were added. The mixture was stirred at room temperature for 1 hour and 15 minutes. The solvent was evaporated and the residue was suspended in EtOAc and filtered. The solution was extracted with 0.5 M $NaH_2PO_4$ (3×) and dried. The product was purified by column chromatography (2% MeOH in $CH_2Cl_2$) yielding 304 mg (37%) of the title compound. $^1$H NMR ($CDCl_3$) δ 6.76 (d, 1H, J=1.8 Hz, H-6); 6.57 (d, 1H, J=1.2 Hz, H-2); 4.13 (d, 2H, J=5.8 Hz, $CH_2$); 1.49 (s, 9H, $(CH_3)_3C$); $^{13}$C NMR ($CDCl_3$) δ 156.5 (CO), 140.1 (C-4), 136.9 (C-1), 133.0 (C-3), 120.3 (C-6), 114.3 (C-2), 110.7 (C-5), 79.8 (($(CH_3)_3\underline{C}$), 44.2 ($CH_2$), 28.8 (($\underline{CH_3}$)$_3$C).

2-amino-4-(aminomethyl)-6-bromophenol

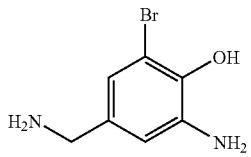

A solution of 3-Bromo-4-hydroxy-5-nitrobenzonitrile (1.0 g, 4.11 mmol) in 20.0 mL of dry THF was added dropwise to a solution of $BH_3$/THF 1.0 M in THF (12.3 mL) at 0° C. under $N_2$. The reaction mixture was stirred at room temperature for 24 hours. Excess borane was decomposed by the cautious dropwise addition of 1 N HCl at 0° C. It was extracted with EtOAc, washed with $NaHCO_3$, NaCl saturated solution and dried ($Na_2SO_4$ anh.) to give a crude. After purification by column chromatography ($CH_2Cl_2$/MeOH 8:2+1% $NH_4OH$), 170 mg (19%) of the title compound were obtained. $^1$H NMR (DMSO-$d_6$) δ 6.67 (s, 1H, H-5); 6.53 (s, 1H, H-3); 3.52 (s, 2H, $CH_2$). $^{13}$C NMR (DMSO-$d_6$) δ 139.7, 139.4 (C-1, C-4), 136.0 (C-2), 118.5 (C-5), 113.0 (C-3), 111.5 (C-6), 44.9 ($CH_2$).

3-Bromo-4-hydroxy-5-nitrobenzonitrile

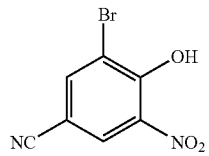

To a mixture of 5 g (30.5 mmol) of 4-hydroxy-3-nitrobenzonitrile in $H_2SO_4$ solution (50 mL of concentrated $H_2SO_4$+ 50 mL of $H_2O$) at 25° C., 7.9 g (47.3 mmol) of potassium bromate were added in small portions cooling the flask with an ice-bath and maintaining the temperature between 25 and 35° C. After the addition was completed, the reaction was stirred at room temperature for 22 h and then filtered. The pale yellow solid was washed with water and dried to give 4.2 g (57%) of the title compound. M.p.: 162-164° C.; $^1$H NMR ($CD_3OD$) δ 8.54 (d, 1H, J=2.0 Hz, H-6), 8.32 (d, 1H, J=2.0 Hz, H-2); $^{13}$C NMR (DMSO-$d_6$) δ 153.9 (C-4), 140.8 (C-2), 138.2 (C-5), 130.1 (C-6), 117.0 (CN), 115.9 (C-3), 101.6 (C-1).

Pharmacological Data

Binding to $A_1$, $A_2$ and $A_3$ Receptors

The compounds of Examples 1 to 8 were evaluated for their pharmacological effect.

These compounds were firstly evaluated for binding to human $A_3$ receptors expressed in Chinese Hamster Ovary cells (CHO cells). [$^{125}$I]-AB-MECA (0.3 nM) binding to membrane preparations was examined using 60 min incubation at room temperature. The displacement of binding by the adenosine analogues was determined, non-specific binding being measured from the displacement by IB-MECA ($10^{-7}$M).

Compounds are identified in the following Tables by their Example number. Values for $A_3$ receptor binding are the $IC_{50}$ values (nM) for displacement of [$^{125}$I]-AB-MECA binding, the concentration for 50% inhibition. These are compared with IB-MECA which has an approximate $IC_{50}$ value of 0.31 nM. Thus, it can be seen from table 1 that compounds 2-4 are approximately equipotent with IB-MECA and that compound 6 is approximately two orders of magnitude more potent.

The selectivity of compounds 2 and 6 for $A_3$ receptors has been evaluated by determining their functional activity at $A_1$ and $A_2$ receptors in preliminary experiments.

For compound 2, $A_1$ receptor functional activity was determined from the negative inotropic response of guinea-pig isolated paced left atria set up in tissue baths containing Krebs-bicarbonate solution gassed with 5% $CO_2$ in oxygen at 37° C. Dose-related inhibition of atrial developed tension (negative inotropy) was observed commencing at 300 nM. The $IC_{50}$ value (concentration for 50% inhibition of contractions) was 7500 nM.

Compound 2's $A_2$ receptor functional activity was determined from the relaxation response of guinea-pig isolated tracheal spirals set up in tissue baths containing Krebs-bicarbonate solution gassed with 5% $CO_2$ in oxygen at 37° C. The tissue was pre-contracted with carbachol (100 nM) and when the tension had reached a plateau, increasing concentrations of compound 9 were introduced cumulatively. There were dose-related relaxations indicative of $A_2$ receptor activity commencing at 1 μM. The $IC_{50}$ (concentration for 50% inhibition of the carbachol-induced contraction) was 20,000 nM. These values compare with $IC_{50}$ values for the non-selective $A_1/A_2$ receptor agonist of 100 nM in the atria and 500 nM in the trachea.

Thus, the selectivity of compound 2 for $A_3$ receptors (radioligand binding) against $A_1$ receptors (negative inotropy) is 16,600 and against $A_2$ receptors (tracheal relaxation) is 44,000.

The results obtained are set out in Table 1, with the $IC_{50}$ for IB-MECA included for comparison.

TABLE 1

| Compound | N6 substituent | R² substituent | A₃ receptor radioligand binding IC$_{50}$/nM | A₂ receptor Isolated Trachea IC$_{50}$/nM | A₁ receptor Isolated atria IC$_{50}$/nM |
|---|---|---|---|---|---|
| 1 | 4-Me-pyridin-2-yl-CH₂ | H | 2.2 | | |
| 2 | 4-I-pyridin-2-yl-CH₂ | H | 0.45 | 20,000 | 7,500 |
| 3 | pyridin-2-yl-CH₂ | H | 6.0 | | |
| 4 | 6-acetyl-pyridin-2-yl-CH₂ | H | 0.4 | | |
| 5 | 4-I-pyridin-2-yl-CH₂ | ·C≡C-Ph | 31-45 | | |
| 6 | 7-I-5-(CH₂-)-2-(NMe₂)-benzoxazole | H | 0.0016 | | |
| 7 | 5-(CH₂-)-2-(NMe₂)-benzoxazole | H | 450 | | |
| 8 | 7-I-5-(CH₂-)-2-(N(Me)-)-benzoxazole | ·C≡C-Ph | 21-80 | | |
| IB-MECA | 3-I-phenyl-CH₂ | H | 0.31 | | |

The lowest $IC_{50}$ value for $A_3$ receptor binding exhibited by the test compounds was found to be that of compound 6.

Table 2 below shows displacement of $[^{125}I]$-AB-MECA (0.3 nM) from human $A_3$ receptors transfected into Chinese Hamster Ovary (CHO) cells by IB-MECA and compound 6.

TABLE 2

| Concentration (Log M) | % Displacement | |
|---|---|---|
| | IB-MECA | Compound 6 |
| −5 | 99 | |
| −7 | 97 | 94 |
| −9 | 73 | 79 |
| −10 | 31 | 73 |
| −11 | | 68 |
| −12 | | 47 |

Total binding in the presence of each concentration of IB-MECA or compound 6 is expressed as a percentage of the total binding in their absence.

Table 3 shows the activity of compound 6 at $A_1$ receptors of guinea-pig atria compared with the standard non-selective agonist, NECA (N-ethylcarboxamidoadenosine).

TABLE 3

| Compound | IC50 (μM) | IC25 (μM) |
|---|---|---|
| NECA | 0.3 | 0.052 |
| Example 6 | 10 | 1 |

Figure 6:
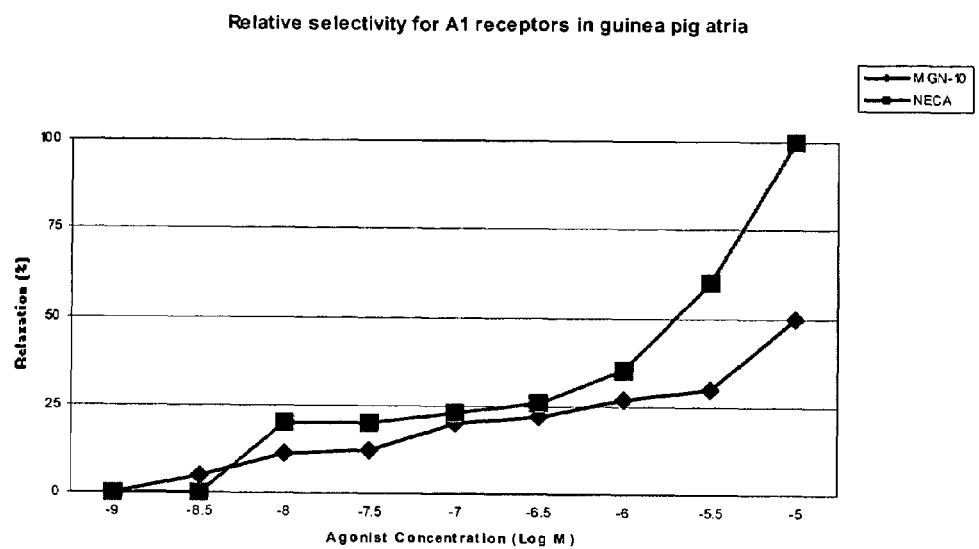
FIG. 6 is a graph of percentage relaxation of guinea pig atria (precontracted with carbachol) against $\log_{10}$ of concentration (M) of compound 6 (diamond) and IB-NECA (square) agonists.

Activity is expressed as the negative inotropic action (reduction in the tension development of paced isolated atria) obtained in cumulative concentration-response curves. At the maximum concentration of compound 6, a maximum effective concentration of NECA was added and the responses to compound 6 were expressed as a percentage of this maximum response. The IC50 and IC25 concentrations (concentrations for 50 and 25% of the maximum response to NECA) were then calculated. After washout of the tissues, a full concentration-response curve for NECA was obtained and the IC25 and IC50 values for NECA calculated. This data is displayed graphically in FIG. 6.

Table 4 shows the activity of compound 6 at $A_2$ receptors of guinea-pig trachea compared with the standard non-selective agonist, NECA (N-ethylcarboxamidoadenosine).

TABLE 4

| Compound | IC25 (μM) |
|---|---|
| NECA | 0.94 |
| Example 6 | 9.07 |

Figure 7:
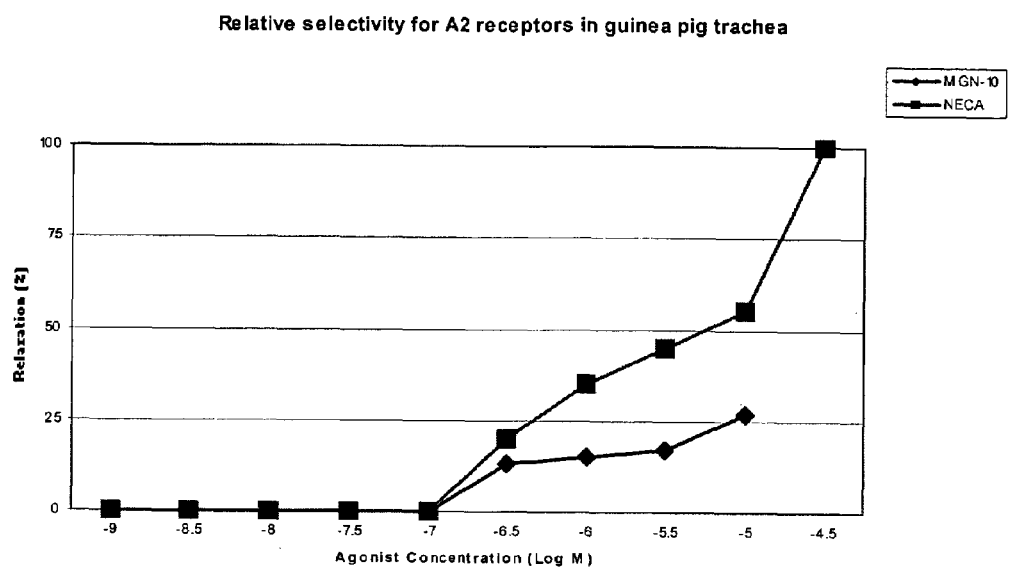
FIG. 7 is a graph of percentage relaxation of guinea pig trachea (preconstructed with carbachol) against $\log_{10}$ of concentration (M) of compound 6 (diamond) and IB-NECA (square) agonists.

The activity is expressed as the relaxation of the trachea precontracted with carbachol (100 nM) obtained in cumulative concentration-response curves. At the maximum concentration of compound 6, a maximum effective concentration of NECA was added and the responses to compound 6 were expressed as a percentage of this maximum response. The IC25 concentration (concentration for 25% of the maximum response to NECA) was then calculated. After washout of the tissues and contraction again with carbachol, a full concentration-response curve for NECA was obtained and the IC25 value for NECA calculated. This data is represented graphically in FIG. 7.

Compound 6 has picomolar potency for binding to the human $A_3$ receptor. Based on functional tests in atrial and tracheal tissues, the selectivity over $A_1$ and $A_2$ receptors is $6.25 \times 10^6$ and $5.6 \times 10^6$, respectively.

Further tests were carried out on compound 6 to evaluate its usefulness as a therapeutic compound.

Efficacy of Compound 6 in Protecting Against Myocardial Contractile Dysfunction of Isolated Atria The following experiment was carried out to evaluate the efficacy of compound 6 in protecting against myocardial contractile dysfunction (stunning) after simulated ischaemia of isolated atria.

Guinea-pig isolated left atria were set up in tissue baths containing Krebs-bicarbonate solution gassed with 5% $CO_2$ in oxygen at 37° C. and electrically paced at 2 Hz with pulses of threshold voltage +50% and 5 ms pulse width. Developed tension was recorded. After equilibrium, they were exposed to 30 min of simulated ischaemia by gassing with 5% $CO_2$ in nitrogen and removing the glucose substrate which was replaced with choline chloride (7 mM) to maintain isotonicity. Pacing was continued throughout. After 30 min, the tissues were reoxygenated and glucose was returned. Contractions were virtually abolished during ischaemia but on reoxygenation contractile function was partially restored and reached 38.0±2% of the pre-ischaemic developed tension after 10 min of reoxygenation. This partial recovery was the index of myocardial stunning. The test compound (compound 6 ($5 \times 10^{-9}$M)) or the reference $A_3$ receptor ligand, IB-MECA ($3 \times 10^{-7}$ M) was introduced at reoxygenation. This timing was to simulate administration at the time of reperfusion induced by thrombolyic therapy following myocardial infarction.

Figure 8:
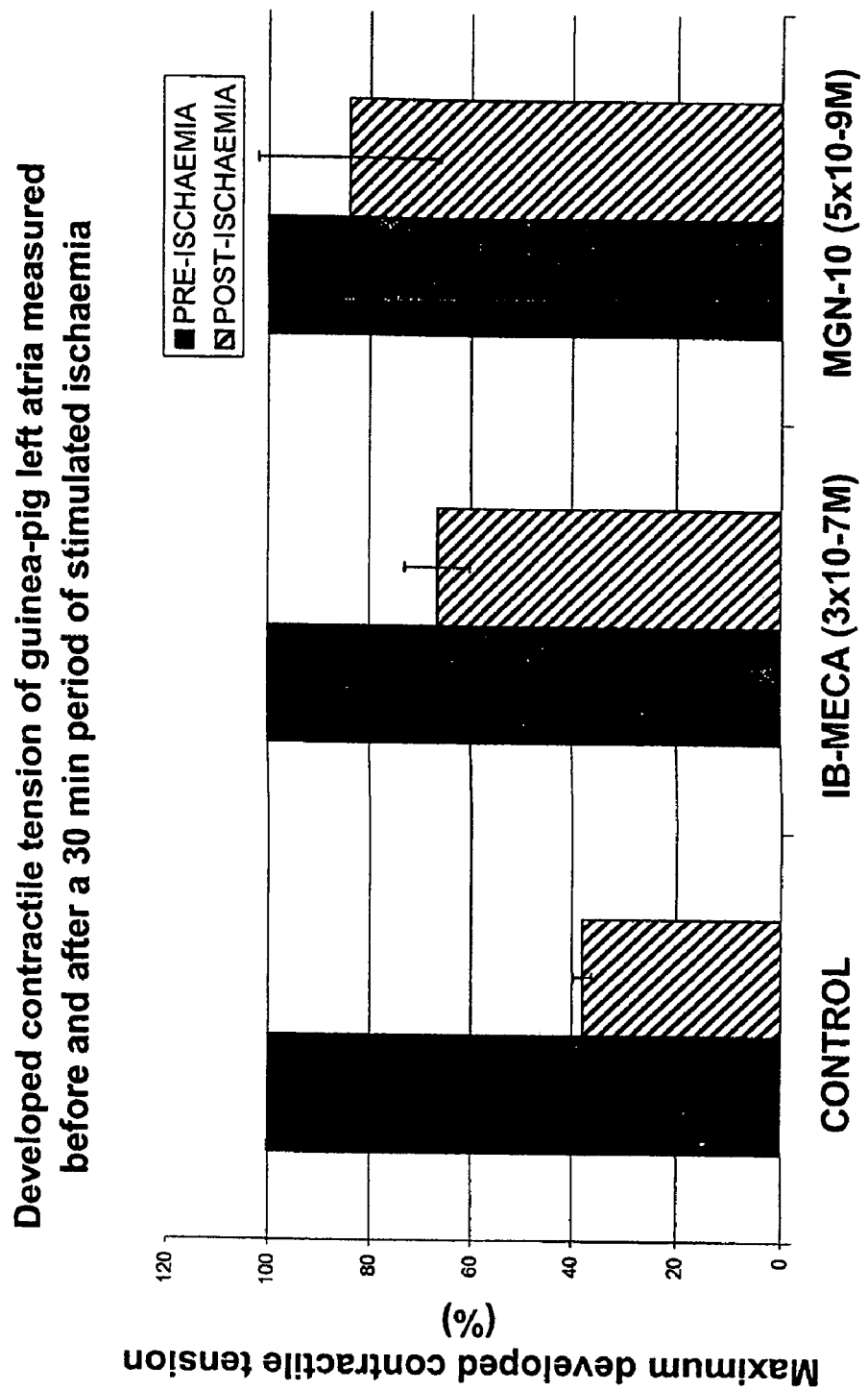
FIG. 8 is a graph showing the developed contractile tension of guinea pig left atria measured before and after a 30 minute period of simulated ischaemia, with IB-MECA ($3\times10^{-7}$M) and compound 6 ($10^{-9}$M) introduced at the onset of regassing.

Table 5 below shows a comparison of the effects of IB-MECA and compound 6 on atrial contractile function after 30 min simulated ischaemia. This data is also represented graphically in FIG. 8.

TABLE 5

| | | Compound 6 ($5 \times 10^{-9}$ M) Maximum developed contractile tension (%) | | CONTROL Simulated ischaemic control | | IB-MECA ($3 \times 10^{-7}$ M) Maximum developed contractile tension (%) | |
|---|---|---|---|---|---|---|---|
| Exp. No. | | Pre-ischaemic | Post-ischaemic | Pre-ischaemic | Post-ischaemic | Pre-ischaemic | Post-ischaemic |
| 1 | | 0.6 g (100%) | 0.40 g (66.7%)* | 100% | 41.7% | 100% | 87.5% |
| 2 | | 0.6 g (100%) | 0.72 g (120%) | 100% | 40% | 100% | 83.3% |

TABLE 5-continued

| | Compound 6 (5 × 10⁻⁹ M) Maximum developed contractile tension (%) | | CONTROL Simulated ischaemic control | | IB-MECA (3 × 10⁻⁷ M) Maximum developed contractile tension (%) | |
|---|---|---|---|---|---|---|
| Exp. No. | Pre-ischaemic | Post-ischaemic | Pre-ischaemic | Post-ischaemic | Pre-ischaemic | Post-ischaemic |
| 3 | 0.6 g (100%) | 0.42 g (65.4%) | 100% | 40% | 100% | 45.5% |
| 4 | | | 100% | 41.7% | 100% | 60% |
| 5 | | | 100% | 30% | 100% | 60% |
| 6 | | | 100% | 41.7% | 100% | 63% |
| 7 | | | 100% | 30.8% | | |
| 8 | | | 100% | 37.8% | | |
| Mean | 100% | 84.0% | 100% | 38.% | 100% | 66.5% |
| SEM | 0 | 18.0% | 0% | 1.7% | 0% | 6.5% |

*< an average of 0.36 and 0.54 g

As can be seen from the above table, when IB-MECA at a concentration of $3 \times 10^{-7}$ M was introduced at regassing, the contractile tension recovered to 66.5±6.5% of its pre-ischaemic value. This value is significantly greater than in the control tissues and indicates a reversal of the myocardial stunning. A concentration of $5 \times 10^{-9}$ M of compound 6 was selected for these experiments based on its potency in the radioligand binding experiments. When this concentration was introduced at the onset of regassing, the recovery of developed tension was to 84.0±18.0% (n=3). Thus at a concentration 60 times less than that of IB-MECA, compound 6 produced a greater degree of recovery of contractile tension following simulated ischaemia.

Efficacy of Compound 6 in Protecting Against Myocardial Contractile Dysfunction of Perfused Hearts The following experiment was carried out to evaluate the efficacy of compound 6 in protecting against myocardial contractile dysfunction (stunning) after no-flow global ischaemia of guinea-pig perfused hearts.

Guinea pig hearts were perfused by the Langendorff method. The cut aortic stump was perfused reterogradely with Krebs solution gassed with 5% $CO_2$ in oxygen at 37° C. at a constant flow rate of 7 ml/min to perfuse the coronary circulation. The heart was jacketed at 37° C. and the spontaneous force of contraction was measured by attaching a clip to the apex of the heart which was connected to a tension transducer. Coronary perfusion pressure was also monitored.

After equilibration, global ischaemia was produced by stopping perfusion and clamping the infusion line. Spontaneous contractions ceased. After 22 minutes, flow was restored to 30% of the pre-ischaemic level. After a further 10 minutes, flow was restored to the pre-ischaemic level (7 ml/min). Spontaneous contractions resumed after about 10 minutes. These contractions reached a maximum recovery of 18.8±7.4% of the pre-ischaemic level. The adenosine receptor ligand infusion was commenced just prior to resumption of 30% coronary perfusion, to mimic administration at reperfusion after thrombolytic therapy, and was continued until restoration of flow to the pre-ischaemic level. The results are presented graphically in FIG. 9.

Significantly improved results were obtained by standardisation of pre-conditioning. Male Dunkin-Harley guinea-pigs (360-390 g) were killed by cervical dislocation and their hearts removed and perfused with krebs-bicarbonate solution via a constant flow Langendorff heart preparation. Between cervical dislocation and perfusion of the isolated heart a period of 2.5 minutes elapsed where the heart was not perfused. During this period the isolated heart was mounted onto the cannula in readiness for perfusion. The experiment not was performed on any preparation that could not be mounted and perfused within 2.5 minutes. In addition the pulmonary artery was cut to assist out flow of perfusate from the heart. Data shown is the developed tension measured as a percentage of the pre-ischaemic level. Error bars represent S.E.M. * denotes a significant difference from control (p>0.05) using a unpaired t-test. For the control n=6 and for the drug treated group n=4.

The results are presented graphically in FIG. 10.

Pharmacodynamic Considerations

The $pK_a$ values for compounds 6 and 7 are given in Table 6 below. The partition coefficient profile for compound 6 is given in Table 7 below. The partition measurements were based on a long chain ester (propylene glycol dipelargonate-PGDP)/water model.

Table 6 shows $pK_a$ values of compounds 6 and 7 calculated using methanol and dimethylformamide co-solvents respectively. All experiments carried out in ionic strength water (0.15 KCl).

TABLE 6

| Compound | n | $pK_a$ (s) | Acidic or basic | Error | GOF* | R²** | Average Temp/° C. | Co-solvent | Comments |
|---|---|---|---|---|---|---|---|---|---|
| 6 | 4 | 3.66 | B | 0.025 | 0.18 | 0.9851 | 19.5 | Methanol | |
| 7 | 3 | 3.61 | B | 0.09 | 1.72 | 0.9517 | 20.2 | Dimethylformamide | Methanol found to be poor solvent |

*"goodness of fit" of data to chosen ionisation model. A high GOF indicates poor fit; values close to unity (<2) are considered to provide a highly reliable result
**Linear regression coefficient for Yasuda-Shediovsky Plot for multiple titrations in presence of different % co-solvent (aqueous $pK_a$ obtained by extrapolation).

Table 7 shows Log P value of compound 6 (partition solvent: propylene glycol dipelargonate (PGDP).

TABLE 7

| n | Log P(s) | Log D | Partitioning species | Error | GOF* | Average Temp/° C. |
|---|---|---|---|---|---|---|
| 2 | 1.484 | 1.483 | neutral | 0.031 | 1.24 | 21.2 |

*"goodness of fit" of data to chosen ionisation model. A high GOF indicates poor fit; values close to unity (<2) are considered to provide a highly reliable result No $2^{nd}$ $pK_a$ was reported. A $pK_a$ of 3.7 would be expected for the benzoxazole part and a $pK_a$ of 3.2 for the adenine moiety (protonation expected at N1). The reported $pK_a$ value of 3.66±0.03 therefore, very probably refers to the benzoxazole moiety. The partition coefficient of 1.48±0.03 on the $log_{10}$ scale indicates that the compound is not too lipophilic. The precise model for optimal pharmacodynamic properties is believed to be a value of unity (i.e. a value of zero on the $log_{10}$ scale) or a little over for a hydrocarbon/water model. Empiric evidence shows that propranolol has an effective partition after allowing for protonation of some 0.8 on the $log_{10}$ PGDP/$H_2$O scale. The presence of a sugar moiety in the adenosine system may increase the relative value of compound 10 on this particular scale. Even so, the difference from this chosen optimum of a little over 0.6 $log_{10}$ units is equivalent to the presence of only one methyl group. Intravenous injection is likely to reduce any significance in the optimal properties.

What is claimed is:

1. A compound having a formula:

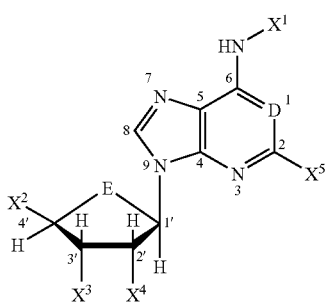

wherein
D is N or CH;
E is O, S or $CH_2$;
$X^1$ is a group of the formula —$CR^{20}R^{21}$-CYCLE, where $R^{20}$ and $R^{21}$ are the same or different and are H, F or $CH_3$;
CYCLE is
a bicyclic ring of the formula V:

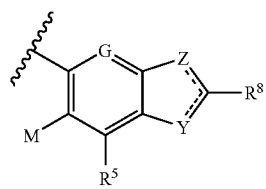

where G is N, CH, CF, $CCH_3$ or $CCF_3$,
M is H,
Y is —O— or —N=, and
Z is —N= when Y is O, or is O when Y is —N=;
$R^5$ is H, $CH_3$, I, Br, Cl, $CF_3$, OH or $NH_2$; and
$R^8$ is H, —$NR^9R^{10}$—$CHR^9R^{10}$ or —N=$CR^9R^{10}$, where $R^9$ and $R^{10}$ are the same or different and are hydrogen, $C_1$-$C_4$ alkyl, $C_1$-$C_4$ alkenyl or $C_1$-$C_4$ alkoxyalkyl
$X^2$ is mono-N— or di-N,N-($C_1$-$C_4$)alkylaminocarbonyl, mono-N— or di-N,N-($C_3$-$C_5$)cycloalkyl-aminocarbonyl or N—($C_1$-$C_4$)alkyl-N—($C_3$-$C_5$)cycloalkylaminocarbonyl;
$X^3$ is OH or NH2;
$X^4$ is OH;
$X^5$ is H, halogen, ($C_1$-$C_{10}$)alkyl, trifluoromethyl ($C_2$-$C_{10}$) alkenyl, ($C_2$-$C_{10}$)alkynyl, or either of the latter two groups optionally being terminally substituted by an aryl or heteroaryl group and, when having a terminal methyl group, optionally further terminally substituted by hydroxy,
or a pharmaceutically acceptable salt or prodrug thereof or a pharmaceutically acceptable salt of such a prodrug.

2. The compound of claim 1 wherein
$R^5$ is —$CH_3$, —I, —Br, —Cl or —$CF_3$; and
$R^8$ is —$NR^9R^{10}$,
where $R^9$ and $R^{10}$ are the same and are $C_1$-$C_4$ alkyl, $C_1$-$C_4$ alkenyl or $C_1$-$C_4$ alkoxyalkyl.

3. The compound of claim 1 wherein the compound is of the formula IV:

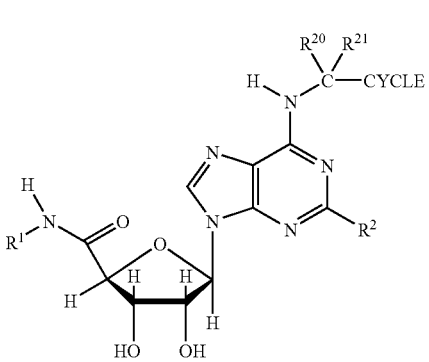

where:
CYCLE, $R^{21}$, and $R^{22}$ are as defined in claim 1;
$R^1$ is $C_1$-$C_4$ alkyl; and
$R^2$ is hydrogen, halo, methyl or trifluoromethyl, or is an alkynyl radical of the formula

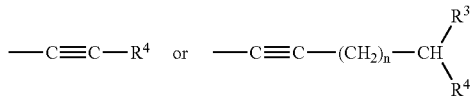

or an alkenyl radical of the formula

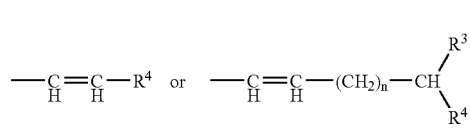

where n is 0 or an integer of from 1 to 4, $R^3$ is hydrogen or hydroxy, and $R^4$ is methyl, a substituted or unsubstituted phenyl, a substituted or unsubstituted naphthyl or Het where Het is a 5 or 6 membered heterocyclic aromatic or non-aromatic ring, optionally benzocondensed, containing 1 to 3 heteroatoms of oxygen, sulfur or nitrogen linked to $R^2$ through a carbon atom or through a nitrogen atom.

4. The compound of claim 3 wherein the compound is of the formula I or II:

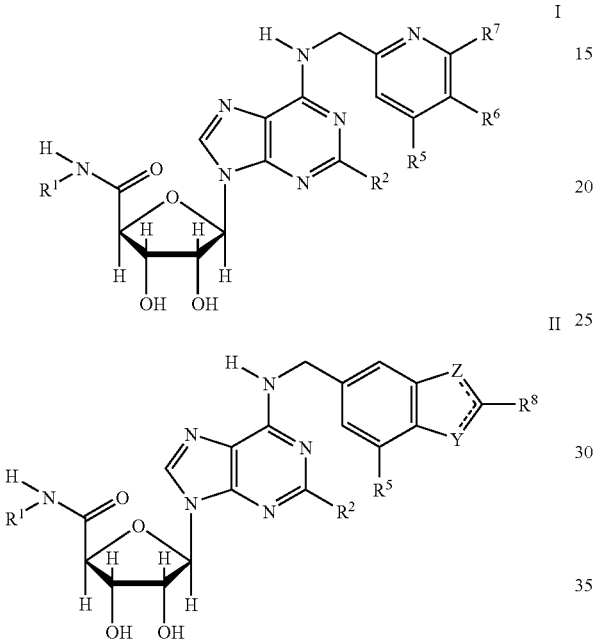

wherein:

$R^1$ is $C_1$-$C_4$ alkyl;

$R^2$ is hydrogen, halo, methyl, trifluoromethyl, an alkynyl radical of the formula

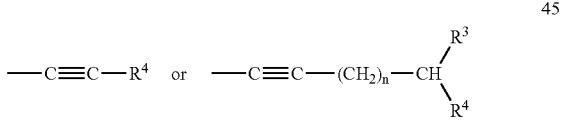

or an alkenyl radical of the formula

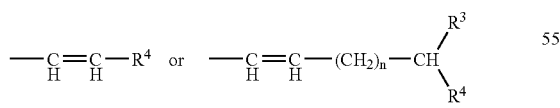

where n is 0 or an integer of from 1 to 4, $R^3$ is hydrogen or hydroxy, and $R^4$ is methyl, a substituted or unsubstituted phenyl, a substituted or unsubstituted naphthyl or Het where Het is a 5 or 6 membered heterocyclic aromatic or non-aromatic ring, optionally benzocondensed, containing 1 to 3 heteroatoms of oxygen, sulfur or nitrogen linked to $R^2$ through a carbon atom or through a nitrogen atom;

$R^5$ is hydrogen, halo, methyl or trifluoromethyl; and $R^6$ and $R^7$, when taken together with the carbon atoms to which they are attached, form an oxazole ring in which the carbon between the oxygen and the nitrogen of the oxazole may optionally be substituted by an amine group having the formula —$NR^9R^{10}$ where each of $R^9$ and $R^{10}$, which may be the same or different is hydrogen, a $C_1$-$C_4$ alkyl radical or a $C_1$-$C_4$ alkenyl;

$R^8$ is H or —$NR^9R^{10}$ in which $R^9$ and $R^{10}$, which may be the same or different, are hydrogen, a $C_1$-$C_4$ alkyl radical, a $C_1$-$C_4$ alkenyl radical or a $C_1$-$C_4$ alkoxyalkyl radical, or $R^8$ is —$CHR^9R^{10}$ or —$N=CR^9R^{10}$ (wherein $R^9$ and $R^{10}$ are as already defined), —$OR^{11}$ or $SR^{11}$ one of Y and Z is nitrogen and the other of Y and Z is oxygen; and

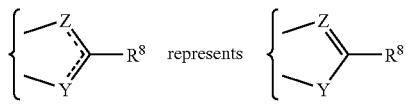

where Z is nitrogen and Y is oxygen and

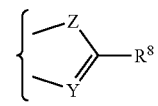

where Y is nitrogen and Z is oxygen.

5. The compound of claim 4 which is a compound of the formula I:

or a pharmaceutically acceptable salt or prodrug thereof or a pharmaceutically acceptable salt of such a prodrug, wherein:

$R^1$, $R^6$ and $R^7$ are as defined in claim 4 and $R^2$ is hydrogen, halo, an alkynyl radical of the formula

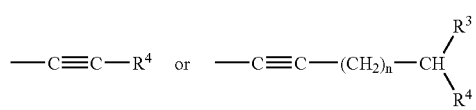

or an alkenyl radical of the formula

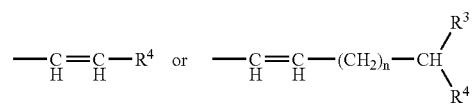

where n is 0 or an integer of from 1 to 4, $R^3$ is hydrogen or hydroxy, and $R^4$ is methyl, a substituted or unsubstituted phenyl, a substituted or unsubstituted naphthyl or Het where Het is a 5 or 6 membered heterocyclic aromatic or non-aromatic ring, optionally benzocondensed, containing 1 to 3 heteroatoms selected from oxygen, sulfur or nitrogen linked to $R^2$ through a carbon atom or through a nitrogen atom and $R^5$ is hydrogen, halo or methyl;

and $R^8$ is H or —$NR^9R^{10}$ in which $R^9$ and $R^{10}$, which may be the same or different, are hydrogen, a $C_1$-$C_4$ alkyl radical or a $C_1$-$C_4$ alkenyl.

6. The compound of claim 5, wherein the compound has the formula:

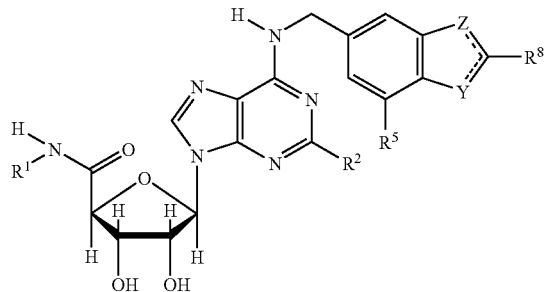

where one of Y and Z is nitrogen and the other is oxygen, and

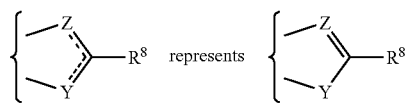 represents where Z is nitrogen and Y is oxygen and

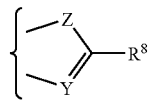

where Y is nitrogen and Z is oxygen.

7. The compound of claim 4, wherein $R^5$ is bromo, iodo or methyl.

8. The compound of claim 4, wherein $R^6$ and $R^7$, when taken together with the carbon atoms to which they are attached, form an oxazole ring optionally substituted by $-NR^9R^{10}$ where $R^9$ and $R^{10}$ may be the same or different, and are hydrogen, a $C_1$-$C_4$ alkyl radical or a $C_1$-$C_4$ alkenyl.

9. The compound of claim 4, wherein Y is oxygen and Z is nitrogen.

10. The compound of claim 9 wherein $R^2$ is H, Y is oxygen, Z is nitrogen, and $R^9$ and $R^{10}$ are both the same and are methyl, ethyl or $-CH_2-CH=CH_2$.

11. The compound of claim 4 wherein the compound is of the formula II:

or a prodrug or pharmaceutically acceptable salt of such a compound or a pharmaceutically acceptable salt of such a prodrug.

12. The compound of claim 11, wherein the compound is $N^6$-[(2-dimethylamino-7-iodo-1,3-benzoxazol-5-yl)-methyl]-adenosine-5'-N-methyl uronamide;

$N^6$-[(2-Dimethylamino-1,3-benzoxazol-5-yl)-methyl]-adenosine-5'-N-methyluronamide; or $N^6$-[(2-dimethylamino-7-iodo-1,3-benzoxazol-5-yl)-methyl]-2-(2-phenyl-1-ethynyl)-adenosine-5'-N-methyluronamide.

13. The compound of claim 3, wherein $R^1$ is methyl or ethyl.

14. The compound of claim 3, wherein $R^2$ is hydrogen, chloro, bromo, iodo, methyl or trifluoromethyl.

15. The compound of claim 3, wherein $R^8$ is $-NR^9R^{10}$, and $R^9$ and $R^{10}$ are both the same and are methyl, ethyl or $-CH_2-CH=CH_2$.

16. A process for making compound I as defined in claim 4, which comprises the step of reacting a compound of the formula:

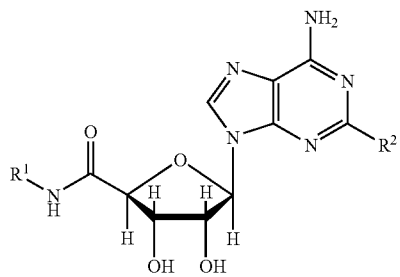

optionally protected in dimethylformamide, with a compound of the following formula:

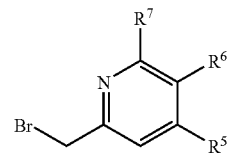

wherein $R^1$, $R^2$, $R^5$, $R^6$, and $R^7$ are as defined in claim 4.

17. A process for making a compound as defined in claim 11, which comprises reacting in a sealed vessel a compound of the formula:

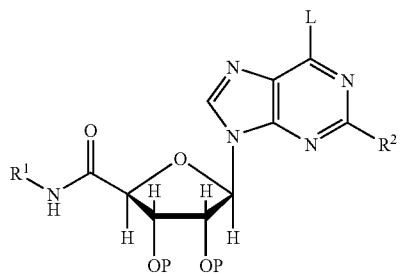

where $R^1$ and $R^2$ are as defined in claim 4, L is a leaving group, and each P is a protecting group or, together, represent a bridging protecting group, with a compound of the following formula in anhydrous ethanol/triethylamine:

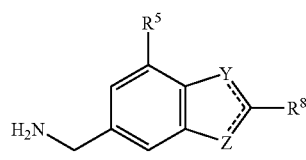

where $R^5$, $R^8$, Y and Z are as defined in claim 1 to form a compound of the following formula:

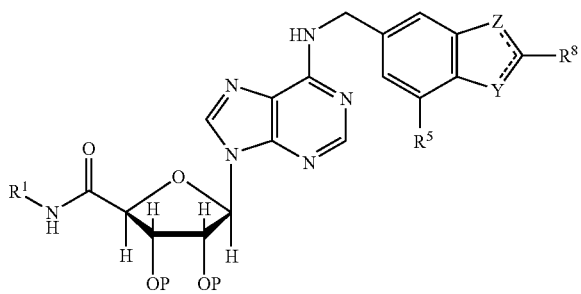

deprotecting the resulting compound;
and optionally forming a pharmaceutically acceptable salt thereof.

18. The compound of claim 1 wherein D is N and E is O.
19. The compound of claim 18 wherein $R^5$ is $CH_3$.
20. The compound of claim 18 wherein G is N.
21. The compound of claim 18 wherein $X^5$ is H.
22. The compound of claim 18 wherein Z is N and Y is O.
23. The compound of claim 18 wherein Z is N, Y is O, G is N and $R^5$ is $CH_3$.
24. The compound of claim 23 wherein $X^2$ is mono-N— or di-N,N-($C_1$-$C_4$)alkylaminocarbonyl; $X^3$ is —OH; $X^4$ is —OH; and $X^5$ is H.
25. A pharmaceutical composition comprising a compound of claim 1 and a pharmaceutically acceptable carrier or diluent.
26. A method of stimulating adenosine $A_3$ receptors, comprising administering to a mammal in need of such treatment a therapeutically effective amount of a compound of claim 1.
27. A method of reducing tissue or organ damage resulting from ischaemia or hypoxia, comprising administering to a mammal in need of such treatment a therapeutically effective amount of a compound of claim 1.

* * * * *